(12) United States Patent
Parker et al.

(10) Patent No.: US 10,441,636 B2
(45) Date of Patent: Oct. 15, 2019

(54) METHOD OF DIAGNOSIS AND TREATMENT

(71) Applicant: LA TROBE UNIVERSITY, Bundoora, Victoria (AU)

(72) Inventors: Belinda Sheree Parker, Victoria (AU); Paul John Hertzog, Victoria (AU)

(73) Assignee: LA TROBE UNIVERSITY, Victoria (AU)

( * ) Notice: Subject to any disclaimer, the term of this patent is extended or adjusted under 35 U.S.C. 154(b) by 0 days.

(21) Appl. No.: 14/415,832

(22) PCT Filed: Jul. 19, 2013

(86) PCT No.: PCT/AU2013/000801
§ 371 (c)(1),
(2) Date: Jan. 20, 2015

(87) PCT Pub. No.: WO2014/012147
PCT Pub. Date: Jan. 23, 2014

(65) Prior Publication Data
US 2015/0174205 A1    Jun. 25, 2015

(30) Foreign Application Priority Data

Jul. 20, 2012 (AU) ................. 2012903104

(51) Int. Cl.
*C12Q 1/6886* (2018.01)
*A61K 38/21* (2006.01)
*G01N 33/53* (2006.01)
*G01N 33/574* (2006.01)
*A61K 31/4745* (2006.01)

(52) U.S. Cl.
CPC .......... *A61K 38/21* (2013.01); *A61K 31/4745* (2013.01); *C12Q 1/6886* (2013.01); *G01N 33/57484* (2013.01); *C12Q 2600/112* (2013.01); *C12Q 2600/158* (2013.01); *C12Q 2600/16* (2013.01); *G01N 2333/4706* (2013.01); *G01N 2333/56* (2013.01); *G01N 2333/7156* (2013.01)

(58) Field of Classification Search
None
See application file for complete search history.

(56) References Cited

U.S. PATENT DOCUMENTS

2008/0014579 A1    1/2008   Liu et al.

FOREIGN PATENT DOCUMENTS

| WO | 0118039 | 3/2001 |
| WO | 2007110231 A2 | 10/2007 |
| WO | 2007139598 A2 | 12/2007 |

OTHER PUBLICATIONS

Takaoka et al. (2008), Cancer Sci. 99: p. 467-478.*
Kaczanowska et al. J.Leukoc. biol. 93:847-863; 2013. (Year: 2013).*
Tsuno et al., J. Immunother., vol. 32(8): 803-816) (Year: 2009).*
Critchley-Thorne et al., PNAS, vol. 106 No. 22, pp. 9010-9015) (Year: 2009).*
Luker et al., Cancer Research, vol. 61, pp. 6540-6547 (Year: 2001).*
Li et al., "Epigenetic Silencing of IRF7 and/or IRF5 in Lung Cancer Cells Leads to Increased Sensitivity to Oncolytic Viruses", PLOS One, vol. 6, No. 12, Dec. 14, 2011, 10 pages.
Extended European Search Report, dated Mar. 14, 2016, 17 pages.
Adeegbe et al., "In vivo induction of myeloid suppressor cells and CD4+ Foxp3+ T regulatory cells prolongs skin allograft survival in mice", Cell transplantation 20.6 (2011): 941-954.
Alon et al., "Broad patterns of gene expression revealed by clustering analysis of tumor and normal colon tissues probed by oligonucleotide arrays", Proceedings of the National Academy of Sciences 96.12 (1999): 6745-6750.
Bunin et al., "The combinatorial synthesis and chemical and biological evaluation of a 1, 4-benzodiazepine library", Proceedings of the National Academy of Sciences 91.11 (1994): 4708-4712.
Cimino et al., "Epithelial Cell Adhesion Molecule (EpCAM) is Overexpressed in Breast Cancer Metastases", Breast Cancer Res Treat 123:701-708 (2010).
Culhane et al., "GeneSigDB—a curated database of gene expression signatures", Nucleic Acids Research 38:D716-D725 (2010).
Derisi et al., "Use of a cDNA microarray to analyse gene expression patterns in human cancer", Nature Genetics 14:457-460 (1996).
Dewitt et al., ""Diversomers": An approach to nonpeptide, nonoligomeric chemical diversity", Proc. Natl. Acad. Sci. USA, 90:6909-6913, (1993).
Dunn et al., "A critical function for type I interferons in cancer immunoediting", Nature immunology 6.7 (2005): 722-729.
Dupre et al., "Murine mammary carcinoma 4T1 induces a leukemoid reaction with splenomegaly: association with tumor-derived growth factors", Experimental and molecular pathology 82.1 (2007): 12-24.
Eckhardt et al., "Genomic Analysis of a Spontaneous Model of Breast Cancer Metastasis to Bone Reveals a Role for the Extracellular Matrix", Molecular Cancer Research 3.1 (2005): 1-13.
Fix, "Oral controlled release technology for peptides: status and future prospects", Pharmaceutical research 13.12 (1996): 1760-1764.
Frith et al., "Detection of functional DNA motifs via statistical over-representation" Nucleic acids research 32.4 (2004): 1372-1381.

(Continued)

*Primary Examiner* — Daniel E Kolker
*Assistant Examiner* — Jegatheesan Seharaseyon
(74) *Attorney, Agent, or Firm* — Kilpatrick Townsend & Stockton LLP

(57) ABSTRACT

The present invention relates generally to a method of diagnosing, prognosing or monitoring the development or progress of metastatic cancer, more particularly bone metastatic cancer. The method of the present invention more particularly provides a method for detecting metastatic cancer, or a predisposition thereto, by screening for the differential expression of a panel of genes which comprise an IRF7 binding site. In a related aspect, the present invention provides a method of therapeutically or prophylactically treating metastatic cancer, in particular bone metastatic cancer. More particularly, the present invention provides a means of therapeutically or prophylactically treating metastatic cancer by upregulating type I IFN levels.

9 Claims, 22 Drawing Sheets

Specification includes a Sequence Listing.

(56) References Cited

OTHER PUBLICATIONS

Germer et al., "High-throughput SNP allele-frequency determination in pooled DNA samples by kinetic PCR", Genome research 10.2 (2000): 258-266.
Guo et al., "Direct fluorescence analysis of genetic polymorphisms by hybridization with oligonucleotide arrays on glass supports", Nucleic acids research 22.24 (1994): 5456-5465.
Haibe-Kains et al., "A three-gene model to robustly identify breast cancer molecular subtypes", Journal of the National Cancer Institute 104.4 (2012): 311-325.
Harrell et al., "Genomic analysis identifies unique signatures predictive of brain, lung, and liver relapse", Breast cancer research and treatment 132.2 (2012): 523-535.
Hayakawa et al., "CD27 dissects mature NK cells into two subsets with distinct responsiveness and migratory capacity", The Journal of Immunology 176.3 (2006): 1517-1524.
Heid et al., "Real time quantitative PCR", Genome research 6.10 (1996): 986-994.
Hervas-Stubbs et al., "Direct effects of type I interferons on cells of the immune systems", Clinical Cancer Research 17.9 (2011): 2619-2627.
Honda et al., "IRF-7 is the master regulator of type-I interferon-dependent immune responses", Nature 434.7034 (2005): 772-777.
Hwang et al., "A null mutation in the gene encoding a type I interferon receptor component eliminates antiproliferative and antiviral responses to interferons alpha and beta and alters macrophage responses", Proceedings of the National Academy of Sciences 92.24 (1995): 11284-11288.
Lelekakis et al., "A novel orthotopic model of breast cancer metastasis to bone". Clinical & experimental metastasis 17.2 (1999): 163-170.
Lu et al., "Regulation of the Promoter Activity of Interferon Regulatory Factor-7 Gene Activation by Interferon and Silencing by Hypermethylation", Journal of Biological Chemistry 275.41 (2000): 31805-31812.
Maskos et al., "Oligonucleotide hybridisations on glass supports: a novel linker for oligonucleotide synthesis and hybridisation properties of oligonucleotides sythenised in situ", Nucleic acids research 20.7 (1992): 1679-1684.
Matys et al., "TRANSFAC® and its module TRANSCompel® transcriptional gene regulation in eukaryotes", Nucleic acids research 34.suppl 1 (2006): D108-D110.
Mikeska et al., "Analysing DNA methylation using bisulphite pyrosequencing", Epigenentics Protocols. Humana Press, 2011, 33-53.
Minn, "Genes that mediate breast cancer metastasis to lung", Nature 436.7050 (2005): 518-524.
Nielsen, "Applications of peptide nucleic acids", Current Opinion in Biotechnology 10.1 (1999): 71-75.
Nielsen et al., "Sequence-selective recognition of DNA by strand displacement with a thymine-substituted polyamide", Science 254. 5037 (1991): 1497-1500.
Parker et al., "Primary tumour expression of the cysteine cathepsin inhibitor Stefin A inhibits distant metastasis in breast cancer", The Journal of pathology 214.3 (2008): 337-346.
Parker et al., "Alterations in vascular gene expression in invasive breast carcinoma", Cancer research 64.21 (2004): 7857-7866.
Patton, "Breathing life into protein drugs", Nature biotechnology 16.2 (1998): 141-143.
Pease et al., "Light-generated oligonucleotide arrays for rapid DNA sequence analysis", Proceedings of the National Academy of Sciences 91.11 (1994): 5022-5026.
Pevzner et al., "Improved chips for sequencing by hybridization", Journal of Biomolecular Structure and Dynamics 9.2 (1991): 399-410.
Putney et al., "Improving protein therapeutics with sustained-released formulations", Nature biotechnology 16.2 (1998): 153-157.
Ribechini et al., "Subsets, expansion and activiation of myeloid-derived suppressor cells", Medical microbiology and immunology 199.3 (2010): 273-281.
Samanen et al., "Chemical approaches to improve the oral bioavailability of peptidergic molecules", Journal of pharmacy and pharmacology 48.2 (1996): 119-135.
Sano et al., "A Streptavidin—Protein a Chimera that allows one-step production of a variety of Specific Antibody Conjugates", Nature Biotechnology 9.12 (1991): 1378-1381.
Savitsky et al., "Regulation of immunity and oncogenesis by the IRF transcription factor family", Cancer immunology, immunotherapy 59.4 (2010): 489-510.
Schena et al., "Quantitative monitoring of gene expression patterns with a complementary DNA microarray", Science 270.5235 (1995): 467-470.
Sheehan et al., "Blocking monoclonal antibodies specific for mouse IFN-α/β receptor subunit 1 (IFNAR-1) from mice immunized by in vivo hydrodynamic transfection", Journal of interferon & cytokine research 26.11 (2006): 804-819.
Smith et al., "Direct mechanical measurements of the elasticity of single DNA molecules by using magnetic beads", Science 258.5085 (1992): 1122-1126.
St. Croix et al., "Genes expressed in human tumor endothelium", Science 289.5482 (2000): 1197-1202.
Urdea et al., "Branched DNA amplification multimers for the sensitive, direct detection of human hepatitis viruses", Nucleic acids symposium series. No. 24, 1990.
Waight et al., "Tumor-derived G-CSF facilitates neoplastic growth through a granulocytic myeloid-derived suppressor cell-dependent mechanism", PLoS one 6.11 (2011): e27690.
Wojdacz, "Methylation-sensitive high-resolution melting (MS-HRM): a new approach for sensitive and high-throughput assessment of methylation", Nucleic Acids Res 35:e41 (2007).
Wu et al., "Heterogeneity of breast cancer metastases: comparison of therapeutic target expression and promoter methylation between primary tumors and their multifocal metastases", Clinical Cancer Research 14.7 (2008): 1938-1946.
Wu et al., "Extraction and Amplification of DNA From Formalin-Fixed, Paraffin-Embedded Tissues", Applied Immunohistochemistry & Molecular Morphology 10(3): 269-271, 2002.
Yang et al., "Abrogation of TGFβ signaling in mammary carcinomas recruits Gr-1+ CD11b+ myeloid cells that promote metastasis", Cancer cell 13.1 (2008): 23-35.
Youn et al., "Subsets of myeloid-derived suppressor cells in tumor-bearing mice", The Journal of Immunology 181.8 (2008): 5791-5802.
Urdea et al., "Branched DNA amplification multimers for the sensitive, direct detection of human hepatitis viruses", Nucleic acids symposium series. No. 24, 1991.
Bidwell, et al., "Silencing of Irf7 pathways in breast cancer cells promotes bone metastasis through immune escape", Nature Medicine vol. 18(8), 2012, pp. 1224-1231.
Bidwell, et al., "Stimulation of Type I interferon defence pathways as a therapy to block the spread of breast cancer to bone", Cancer Research, vol. 49, 2008, p. 102.
Hertzog, et al., "Novel Theraputic Targets in Malignancies", Cytokine, vol. 52(1-2), 2010, p. 68.
Parker, et al., "Tumor cell induced immune evasion via loss of Type I IFN signalling promoted breast cancer matastasis", Cytokine vol. 56(1), 2011, p. 102.
Slaney, et al., "The role of Type I interferons in immunoregulation of breast cancer metastasis to the bone", Oncoimmunology, vol. 2(1), Jan. 2013, pp. e22339-1-e22339-3.
International Application No. PCT/AU2013/000801, International Search Report dated Nov. 13, 2013.
Adams, Sylvia, et al. "Topical TLR7 agonist imiquimod can induce immune-mediated rejection of skin metastases in patients with breast cancer," *Clinical Cancer Research* 18.24 (2012): 6746-6757.
Smits, Evelien LJM, et al. "The Use of TLR7 and TLR8 Ligands for the Enhancement of Cancer Immunotherapy," *The Oncologist 2008* 13 (2008): 859-875.
Koga-Yamakawa, Erina, et al. "Intratracheal and oral administration of SM-276001. A selective TLR7 agonist, leads to antitumor effi-

(56) References Cited

OTHER PUBLICATIONS cacy in primary and metastatic models of cancer," *International Journal of Cancer* 132.3 (2013): 580-590.

Yau, Christina, et al. "A multigene predictor of metastatic outcome in early stage hormone receptor-negative and triple-negative breast cancer." *Breast Cancer Research* 12.5 (2010): R85.

Alldridge, Louise, et al. "Proteome profiling of breast tumors by gel electrophoresis and nanoscale electrospray ionization mass spectrometry" *Journal of proteome research* 7.4 (2008): 1458-1469.

Tatsugami, Katsunori, Masatoshi Eto, and Seiji Naito, "Influence of immunotherapy with interferon-α on regulatory T cells in renal cell carcinoma patients," *Journal of Interferon & Cytokine Research* 30.1 (2010): 43-48.

Honda et al., "Type I interferon gene induction by the interferon regulatory factor family of transcription factors", Immunity 25(5):349-360 (2006).

Kawai et al., "TLR signaling", Cell Death & Differentiation 13(5): 816-825 (2006).

Kawai et al., "The roles of TLRs, RLRs and NLRs in pathogen recognition", International immunology 21(4): 317-337 (2009).

Kawai et al., "The role of pattern-recognition receptors in innate immunity: update on Toll-like receptors," Nature Immunology 11(5): 373-384 (2010).

Ning et al., "IRF7: activation, regulation, modification and function", Genes and immunity 12(6): 399-414 (2011).

Roach et al., "The evolution of vertebrate Toll-like receptors", Proceedings of the National Academy of Sciences of the United States of America 102(27): 9577-9582 (2005).

Tamura et al., "The IRF family transcription factors in immunity and oncogenesis", Annu. Rev. Immunol. 26: 535-584 (2008).

Chin et al., "Toll-like receptor 3—mediated suppression of TRAMP prostate cancer shows the critical role of type I interferons in tumor immune surveillance", Cancer Research vol. 70, No. 7, 2010, 2595-2603.

Démoulins et al., "Poly (I: C) induced immune response in lymphoid tissues involves three sequential waves of type I IFN expression", Virology vol. 386, No. 2, 2009, 225-236.

European Application No. 13819559.9 , "Notice of Opposition", Jul. 30, 2019.

Hertzog , Program of emPower eResearch Conference 2012, showing date of the Hertzog Presentation.

Hertzog , Slideshow shown at the empower eResearch Conference in Sydney, Oct. 29, 2012, 22 pages.

Rautela et al., "Stimulating the innate type-1 interferon pathway reduces breast cancer metastasis to bone", Abstract of poster presented at 25th Lorne Cancer Conference in Feb. 2013.

Salaun et al., "TLR3 as a biomarker for the therapeutic efficacy of double-stranded RNA in breast cancer", Cancer research vol. 71, No. 5, 2011, 1607-1614.

Schön et al., "TLR7 and TLR8 as targets in cancer therapy", Oncogene vol. 27, No. 2, 2008, 190-199.

\* cited by examiner

METHOD OF DIAGNOSIS AND TREATMENT

PRIOR RELATED APPLICATIONS

This application is a U.S. national phase patent application under 35 U.S.C. 371 of International Patent Application No. PCT/AU2013/000801, filed Jul. 19, 2013, which claims the benefit of priority to the Australian Application number 2012903104, filed Jul. 20, 2012, each of which is incorporated herein by reference in its entirety.

FIELD OF THE INVENTION

The present invention relates generally to a method of diagnosing, prognosing or monitoring the development or progress of metastatic cancer, more particularly bone metastatic cancer. The method of the present invention more particularly provides a method for detecting metastatic cancer, or a predisposition thereto, by screening for the differential expression of a panel of genes which comprise an IRF7 binding site. In a related aspect, the present invention provides a method of therapeutically or prophylactically treating metastatic cancer, in particular bone metastatic cancer. More particularly, the present invention provides a means of therapeutically or prophylactically treating metastatic cancer by upregulating type I IFN levels.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

A neoplasm is an abnormal mass or colony of cells produced by a relatively autonomous new growth of tissue. Most neoplasms arise from the clonal expansion of a single cell that has undergone neoplastic transformation. The transformation of a normal cell to a neoplastic cell can be caused by a chemical, physical, or biological agent (or event) that alters the cell genome. Neoplastic cells are characterized by the loss of some specialized functions and the acquisition of new biological properties, foremost, the property of relatively autonomous growth. They pass on their heritable biological characteristics to progeny cells. Neoplasms may originate in almost any tissue containing cells capable of mitotic division.

The past, present, and future predicted biological behaviour, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm, however, exhibits a lesser degree of autonomy, is usually not invasive and does not metastasize. Cancer is second only to heart disease as the most common cause of death in western countries. The estimated incidence of cancer in the US, for example, is about $1 \times 10^6$ new cases annually. Nearly 80% of all malignant neoplasms arise in 10 anatomical sites, namely lung, breast, colon and rectum, prostate, lymph nodes, uterus, bladder, pancreas, blood and stomach.

Metastatic tumours are very common in the late stages of cancer. The spread of metastases may occur via the blood, the lymphatics or through both routes, with the most common places for metastases to arise being the lymph nodes, lungs, liver, brain and the bones.

There is a propensity for certain tumours to seed in particular organs. This was first discussed as the "seed and soil" theory by Stephen Paget over a century ago in 1889. For example, prostate cancer usually metastasises to the bones. In a similar manner, colon cancer has a tendency to metastasise to the liver while, in women, stomach cancer often metastasises to the ovary. According to the "seed and soil" theory, it is difficult for cancer cells to survive outside their region of origin, so in order to metastasise they must find a location with similar characteristics. For example, breast tumour cells, which gather calcium ions from breast milk, metastasise to bone tissue, where they can gather calcium ions from bone. Malignant melanoma spreads to the brain, presumably because neural tissue and melanocytes arise from the same cell line in the embryo.

Metastasis involves a complex series of steps in which cancer cells leave the original tumour site and migrate to other parts of the body via the bloodstream or the lymphatic system. To do so, malignant cells break away from the primary tumour and attach to and degrade proteins that make up the surrounding extracellular matrix, which separates the tumour from adjoining tissue. By degrading these proteins, cancer cells are able to breach the extracellular matrix and escape.

The body resists metastasis by a variety of mechanisms through the actions of a class of proteins known as metastasis suppressors, of which about a dozen are known. It has also been determined that one of the critical events required is the growth of a new network of blood vessels, that is tumour angiogenesis. Significant research has therefore focussed on angiogenesis inhibitors as a means to prevent the growth of metastases. Despite these findings, however, the effective treatment of metastatic cancer has been elusive and largely still relies on the application of very non-specific and highly toxic chemotherapy based methods.

Equally elusive has been the development of a method for the early diagnosis of metastatic cancer. Where metastatic cancer is found at the same time as the primary tumour, often in the context of surgery, the prognosis for the patient is usually very poor due to the advanced stage of disease. However, in patients with either an advanced stage but non-metastasised primary tumour or those in whom metastasis has only just commenced, confirmation of metastatic cancer can be virtually impossible to make due to the limitations of current diagnostic techniques. In these patients the primary tumour will be removed and the patient may nevertheless be subjected to a full course of chemotherapy in the hope that this will be effective to kill any metastatic tumours which may be present. However, in the absence of having positively identified any such tumours it is difficult to assess the necessity of this treatment regime. A still further complicating factor is that not all primary tumours will necessarily metastasise and it is virtually impossible, based just on histological analysis, to predict which tumours will metastasise and which will not. In other situations, there will be no chemotherapy provided for possible metastases and if these in fact exist, they will ultimately not be identified until it is virtually too late for effective treatment.

To this end, there is a significant need to develop means of accurately determining the likelihood of a primary tumour becoming metastatic. The current histology based analysis of primary tumours is highly subjective and not all that accurate. The development of a means to reliably and routinely assess a patient presenting with a primary tumour, to determine the likelihood of the onset of metastatic cancer, is therefore highly desirable.

In work leading up to the present invention, a molecular signature has been identified which, if present in a primary tumour, is characteristic of the propensity of that tumour to metastasise. Specifically, downregulation in a tumour of the level of expression of genes which comprise an IRF7 binding site, relative to the levels present in a non-metastatic tumour, is indicative of the presence of a metastatic phenotype. This finding has therefore now provided a sensitive and reliable means to identify tumours which have, or are likely to, metastasise. This information in relation to the classification of the tumour can then inform the development of the therapeutic treatment and ongoing monitoring which is appropriate for the patient.

Still further, this finding has also facilitated the development of a method for therapeutically or prophylactically treating metastatic cancer based on upregulating the levels of Type I interferon in patients diagnosed with primary tumours exhibiting reduced expression levels of the subject gene signature.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention provides a method of assessing the metastatic status of a tumour from an individual, said method comprising detecting the expression of one or more genes by said tumour, which genes comprise an IRF7 binding site in their promoter, wherein a decreased level of expression of said genes relative to the level of expression of said genes in a corresponding, non-metastatic tumour is indicative of the metastatic phenotype of said tumour.

In another aspect there is provided a method of assessing the metastatic status of a tumour from an individual, said method comprising detecting the expression of one or more genes, of Table 1, by said tumour wherein a decreased level of expression of said genes relative to the level of expression of said genes in a corresponding non-metastatic tumour is indicative of the metastatic phenotype of said tumour.

In a related aspect there is provided a method of assessing the metastatic status of a tumour from an individual, said method comprising detecting the functional level of IRF7, IRF9 or STAT1 in said tumour wherein a decrease in the functional level of said IRF7, IRF9 or STAT1 relative to the level of expression of said genes in a corresponding non-metastatic tumour is indicative of the metastatic phenotype of said tumour.

In still another aspect there is provided a method of assessing the metastatic status of a tumour from an individual, said method comprising detecting the expression of one or more genes of Table 1 by said tumour wherein a decreased level of expression of said genes relative to the level of expression of said genes in a corresponding non-metastatic tumour is indicative of the metastatic phenotype of said tumour and wherein the metastases are bone metastases.

In a further aspect there is provided a method of assessing the metastatic status of a tumour from an individual said method comprising detecting the functional level of IRF7, IRF9 or STAT1 in said tumour wherein a decrease in the functional level of said IRF7, IRF9 or STAT1 is indicative of the metastatic phenotype of said tumour and wherein the metastases are bone metastases.

In one embodiment, said tumour is a tumour of the breast, colon, kidney, lungs, skin, ovary, pancreas, prostate, rectum, stomach, thyroid or uterus.

In a further embodiment said screening is directed to at least 10 genes, at least 20 genes, at least 30 genes, at least 40 genes, at least 50 genes, at least 60 genes, at least 70 genes, at least 80 genes, at least 90 genes, at least 100 genes, at least 110 genes, at least 120 genes, at least 130 genes, at least 140 genes, at least 150 genes, at least 160 genes, at least 170 genes, at least 180 genes, at least 190 genes, at least 200 genes or at least 208 genes.

In another embodiment, said screening is directed to one or more genes selected from Table 2.

A further aspect of the present invention is directed to a method of treating metastatic cancer in an individual, which cancer is characterised by aberrant IRF7 functionality, said method comprising administering an effective amount of a composition, wherein said composition comprises an agent which upregulates the level of Type I IFN in said individual.

In another aspect the present invention is more particularly directed to a method of treating a breast, kidney or prostate metastatic cancer in an individual, which cancer is characterised by aberrant IRF7 functionality, said method comprising administering an effective amount of a composition, wherein said composition comprises an agent which upregulates the level of Type I IFN in said individual.

In still another aspect there is provided a method of treating metastatic cancer, which metastases are present in the bone and which cancer is characterised by aberrant IRF7 functionality, in an individual, said method comprising administering an effective amount of a composition, wherein said composition comprises an agent which upregulates the level of Type I IFN in said individual.

In one embodiment there is provided a method of treating metastatic cancer in a patient which cancer is characterised by aberrant IRF7 functionality, said method comprising administering an effective amount of a composition, wherein said composition comprises an agent which upregulates the level of IFN-α in said patient.

In another embodiment there is provided a method of treating metastatic cancer in an individual which cancer is characterised by aberrant IRF7 functionality, said method comprising administering an effective amount of a composition wherein said composition comprises an agent which upregulates the level of IFN-β in said individual.

In a related aspect there is provided the use of an agent which upregulates the level of Type I IFN in the manufacture of a medicament for the treatment of a metastatic cancer in an individual, which cancer is characterised by aberrant IRF7 functionality.

DETAILED DESCRIPTION OF THE INVENTION

Figure 1:
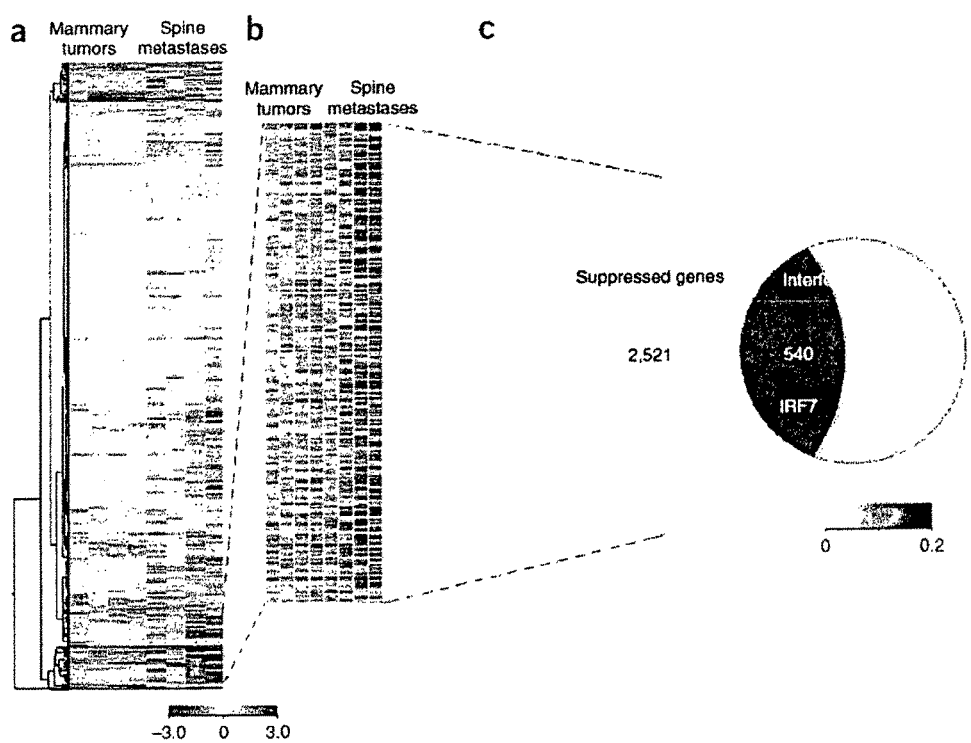
FIG. 1: Bone metastases of breast carcinoma origin down-regulate interferon pathways and other immune genes. Heat maps generated using hierarchical clustering applying Euclidean distance and centroid linkage rule. The colored scale bar represents fold change $Log_2$. The grey bar represents the CLOVER enrichment score as described in Methods. IRF7 was identified as a significant regulatory factor in the intersection of the suppressed genes and the INTERFEROME genes.

The present invention is predicated, in part, on the determination both that the loss of IRF7 gene functionality in a tumour induces a shift to a metastatic phenotype and, further, that this loss of functionality is routinely identifiable by virtue of the presence of a unique gene signature in the tumour, this signature being a downregulation in the level of expression of one or more genes comprising an IRF7 binding site in their promoter. This finding has facilitated not only the development of a method for screening a tumour to determine its propensity to metastasise, but has also led to the development of a means of therapeutically or prophylactically treating patients presenting with a primary tumour which exhibits a metastatic phenotype, said method being based on upregulating levels of Type 1 IFN in the patient.

Accordingly, in one aspect of the present invention there is provided a method of assessing the metastatic status of a tumour from an individual, said method comprising detecting the expression of one or more genes by said tumour, which genes comprise an IRF7 binding site in their promoter, wherein a decreased level of expression of said genes relative to the level of expression of said genes in a corresponding non-metastatic tumour is indicative of the metastatic phenotype of said tumour.

More particularly, there is provided a method of assessing the metastatic status of a tumour from an individual, said method comprising detecting the expression of one or more genes, of Table 1, by said tumour wherein a decreased level of expression of said genes relative to the level of expression of said genes in a corresponding non-metastatic tumour is indicative of the metastatic phenotype of said tumour.

In a related aspect there is provided a method of assessing the metastatic status of a tumour from an individual, said method comprising detecting the functional level of IRF7, IRF9 or STAT1 in said tumour wherein a decrease in the functional level of said IRF7, IRF9 or STAT1 relative to the level of expression of said genes in a corresponding non-metastatic tumour is indicative of the metastatic phenotype of said tumour.

The term "tumour" is used herein to describe an abnormal mass or growth of cells or tissue that is characterized by uncontrolled cell division. Tumours may be benign (not cancerous) or malignant (cancerous). Tumours may be identified, monitored or assessed through clinical screening or diagnostic procedures, including, but not limited to, palpation, biopsy, cell proliferation index, endoscopy, mammography, digital mammography, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art.

More particularly, said tumour is a primary tumour.

Reference to the "metastatic phenotype" of a tumour should be understood as a reference to the capacity of the cells of the subject tumour to spread from the organ or tissue of origin to another organ or tissue, typically via the lymphatics or the blood circulation. It should also be understood that the subject cells, although exhibiting a metastatic phenotype, may or may not have actually traveled to another organ in the patient in whom the tumour has developed. To this end, not only will the existence of advanced stage metastatisation be detected by the method of the present invention but, of more significance, very early stage metastatisation (where the metastases may be few in number and small in size and therefore difficult to detect by currently used methods) or where the primary tumour has transitioned to a metastatic phenotype but the cells of which have not yet actually traveled to another organ (this is likely to reflect a relatively brief period of time). Without limiting the present invention to any one theory or mode of action, the down-regulation of IRF7 functionality is understood to be the trigger for a shift to a metastatic phenotype. Accordingly, this will occur prior to the tumour cells entering the circulation and seeding other organs. By identifying individuals who are either in the very early stages of metastatic disease or who are about to undergo metastatic seeding of distant organs, there is provided the possibility of more appropriate therapeutic intervention than might otherwise have been deemed necessary had the metastatic phenotype not been diagnosable. In this regard, reference to metastatic "status" should be understood to mean that the tumour is assessed to determine whether or not it exhibits a metastatic phenotype.

Without limiting the present invention in any way, in one embodiment it has been determined that the subject method is particularly effective in detecting the metastatic phenotype of tumours which exhibit a predisposition to metastasising to the bone. This is an extremely valuable finding since bone metastases are generally regarded as particularly aggressive and difficult to treat. Accordingly, developing a means to identify tumours exhibiting a metastatic phenotype provides a mechanism of potentially identifying these bone metastases at a much earlier stage than is currently possible. This may then significantly improve the prognostic outcome for the patient.

According to this embodiment, there is provided a method of assessing the metastatic status of a tumour from an individual, said method comprising detecting the expression of one or more genes of Table 1 by said tumour wherein a decreased level of expression of said genes relative to the level of expression of said genes in a corresponding non-metastatic tumour is indicative of the metastatic phenotype of said tumour and wherein the metastases are bone metastases.

In a related embodiment there is provided a method of assessing the metastatic status of a tumour from an individual said method comprising detecting the functional level of IRF7, IRF9 or STAT1 in said tumour wherein a decrease in the functional level of said IRF7, IRF9 or STAT1 is indicative of the metastatic phenotype of said tumour and wherein the metastases are bone metastases.

Still without limiting the present invention in any way, the most common sites of cancer metastases are the lungs, bone and liver. Although most cancers have the ability to spread to many different parts of the body, they will often spread to one site more often than others. Listed below are the three most common sites for metastases, excluding lymph nodes, for several types of cancer:

| Cancer Type | Main sites of metastasis |
| --- | --- |
| Breast | Lungs, liver, bones |
| Colon | Liver, peritoneum, lungs |
| Kidney | Lungs, liver, bones |
| Lungs | Adrenal gland, liver lungs |
| Melanoma | Lungs, skin/muscle, liver |
| Ovary | Peritoneum, liver, lungs |
| Pancreas | Liver, lungs, peritoneum |
| Prostate | Bones, lungs, liver |
| Rectum | Liver, lungs, adrenal gland |
| Stomach | Liver, peritoneum, lungs |
| Thyroid | Lungs, liver, bones |
| Uterus | Liver, lungs, peritoneum |

In one embodiment, said tumour is a tumour of the breast, colon, kidney, lungs, skin, ovary, pancreas, prostate, rectum, stomach, thyroid or uterus.

In another embodiment there is provided a method of assessing the metastatic status of a breast, kidney or prostate tumour from an individual, said method comprising detecting the expression of one or more genes of Table 1 by said tumour wherein a decreased level of expression of said genes relative to the level of expression of said genes in a corresponding non-metastatic tumour is indicative of the metastatic phenotype of said tumour.

In a related embodiment there is provided a method of assessing the metastatic status of a breast, kidney or prostate tumour from an individual, said method comprising detecting the functional level of IRF7, IRF9 or STAT1 in said tumour wherein a decrease in the functional level of said IRF7, IRF9 or STAT1 relative to the level of expression in a corresponding non-metastatic tumour is indicative of the metastatic phenotype of said breast, kidney or prostate tumour.

It should be understood that the method of the present invention does not conclusively identify the site or likely site of metastases. However, the positive diagnosis of a metastatic phenotype does enable one to then design an appropriate monitoring and treatment regime to deal with the patient's transition to metastatic cancer.

As detailed hereinbefore, the present invention is predicated on the unexpected determination that a loss of the functionality of the transcription factor IRF7 in tumour cells results in the transition of these tumour cells to a metastatic phenotype. Without limiting the present invention to any one theory or mode of action interferon regulatory factors (IRFs) are a family of transcription factors with diverse functions which include host defense, cell cycle regulation, apoptosis, oncogenesis, and immune cell development and homeostasis. Currently, there are 10 members of the mammalian IRF family (IRFs 1 to 10), all of which contain a conserved DNA binding domain. The DNA binding domain is located at the amino termini of the IRFs and consists of a five-tryptophan repeat that binds to a specific GAAA genomic sequence that is similar to the IFN-stimulated response element (ISRE). The IRFs become activated via phosphorylation at their carboxyl termini, after which they translocate from the cytoplasm to the nucleus to effect transcription of ISRE-containing genes. The various IRFs differ in cellular localisation, structural properties, an activation-induced stimuli, thus conferring each IRF with unique functions.

The loss of IRF7 expression in a primary tumour has now been determined to shift that tumour to a metastatic phenotype. This finding in its own right provides a basis on which to routinely screen primary tumours to assess their metastatic status. However, it has been still further determined that in these tumours the loss of IRF7 results in downregulation of the expression of some or all of the panel of interferon regulated genes listed in Table 1(a). These genes have in common the presence of an IRF7 binding site in their promoter region. the genes in Table 1(b) are general type I interferon-regulated genes.

TABLE 1(a)

| Ensembl Gene ID | Gene Name |
|---|---|
| ENSG00000002549 | LAP3 |
| ENSG00000003402 | CFLAR |
| ENSG00000004468 | CD38 |
| ENSG00000005893 | LAMP2 |
| ENSG00000006210 | CX3CL1 |
| ENSG00000010278 | CD9 |
| ENSG00000011422 | PLAUR |
| ENSG00000011426 | ANLN |
| ENSG00000013374 | NUB1 |
| ENSG00000023909 | GCLM |
| ENSG00000026508 | CD44 |
| ENSG00000035687 | ADSS |
| ENSG00000038210 | PI4K2B |
| ENSG00000041357 | PSMA4 |
| ENSG00000048828 | FAM120A |

TABLE 1(a)-continued

| Ensembl Gene ID | Gene Name |
|---|---|
| ENSG00000052802 | MSMO1 |
| ENSG00000059378 | PARP12 |
| ENSG00000060491 | OGFR |
| ENSG00000064012 | CASP8 |
| ENSG00000068079 | IFI35 |
| ENSG00000073756 | PTGS2 |
| ENSG00000075785 | RAB7A |
| ENSG00000075886 | TUBA3D |
| ENSG00000081041 | CXCL2 |
| ENSG00000081181 | ARG2 |
| ENSG00000082153 | BZW1 |
| ENSG00000082781 | ITGB5 |
| ENSG00000085449 | WDFY1 |
| ENSG00000086061 | DNAJA1 |
| ENSG00000087157 | PGS1 |
| ENSG00000088205 | DDX18 |
| ENSG00000089127 | OAS1 |
| ENSG00000089505 | CMTM1 |
| ENSG00000091136 | LAMB1 |
| ENSG00000092010 | PSME1 |
| ENSG00000095303 | PTGS1 |
| ENSG00000095752 | IL11 |
| ENSG00000100106 | TRIOBP |
| ENSG00000100142 | POLR2F |
| ENSG00000100292 | HMOX1 |
| ENSG00000100380 | ST13 |
| ENSG00000100519 | PSMC6 |
| ENSG00000100596 | SPTLC2 |
| ENSG00000100664 | EIF5 |
| ENSG00000100714 | MTHFD1 |
| ENSG00000100764 | PSMC1 |
| ENSG00000100911 | PSME2 |
| ENSG00000101000 | PROCR |
| ENSG00000101347 | SAMHD1 |
| ENSG00000101367 | MAPRE1 |
| ENSG00000101384 | JAG1 |
| ENSG00000101577 | LPIN2 |
| ENSG00000102024 | PLS3 |
| ENSG00000102144 | PGK1 |
| ENSG00000102554 | KLF5 |
| ENSG00000103642 | LACTB |
| ENSG00000103811 | CTSH |
| ENSG00000103966 | EHD4 |
| ENSG00000104213 | PDGFRL |
| ENSG00000104375 | STK3 |
| ENSG00000104518 | GSDMD |
| ENSG00000104549 | SQLE |
| ENSG00000104635 | SLC39A14 |
| ENSG00000105808 | RASA4 |
| ENSG00000105835 | NAMPT |
| ENSG00000105939 | ZC3HAV1 |
| ENSG00000107175 | CREB3 |
| ENSG00000107798 | LIPA |
| ENSG00000108342 | CSF3 |
| ENSG00000108424 | KPNB1 |
| ENSG00000108679 | LGALS3BP |
| ENSG00000108691 | CCL2 |
| ENSG00000108771 | DHX58 |
| ENSG00000108946 | PRKAR1A |
| ENSG00000109736 | MFSD10 |
| ENSG00000110697 | PITPNM1 |
| ENSG00000111142 | METAP2 |
| ENSG00000111145 | ELK3 |
| ENSG00000111361 | EIF2B1 |
| ENSG00000112081 | SRSF3 |
| ENSG00000112242 | E2F3 |
| ENSG00000112297 | AIM1 |
| ENSG00000113070 | HBEGF |
| ENSG00000114316 | USP4 |
| ENSG00000114573 | ATP6V1A |
| ENSG00000114738 | MAPKAPK3 |
| ENSG00000114956 | DGUOK |
| ENSG00000115267 | IFIH1 |
| ENSG00000115364 | MRPL19 |
| ENSG00000115415 | STAT1 |
| ENSG00000115677 | HDLBP |
| ENSG00000116285 | ERRFI1 |
| ENSG00000116514 | RNF19B |

TABLE 1(a)-continued

| Ensembl Gene ID | Gene Name |
| --- | --- |
| ENSG00000117394 | SLC2A1 |
| ENSG00000117410 | ATP6V0B |
| ENSG00000117475 | BLZF1 |
| ENSG00000117525 | F3 |
| ENSG00000117650 | NEK2 |
| ENSG00000118503 | TNFAIP3 |
| ENSG00000119917 | IFIT3 |
| ENSG00000119922 | IFIT2 |
| ENSG00000120063 | GNA13 |
| ENSG00000120217 | CD274 |
| ENSG00000120265 | PCMT1 |
| ENSG00000121022 | COPS5 |
| ENSG00000121481 | RNF2 |
| ENSG00000121797 | CCRL2 |
| ENSG00000122877 | EGR2 |
| ENSG00000122884 | P4HA1 |
| ENSG00000122952 | ZWINT |
| ENSG00000123124 | WWP1 |
| ENSG00000123609 | NMI |
| ENSG00000124201 | ZNFX1 |
| ENSG00000124762 | CDKN1A |
| ENSG00000124783 | SSR1 |
| ENSG00000126067 | PSMB2 |
| ENSG00000126214 | KLC1 |
| ENSG00000127314 | RAP1B |
| ENSG00000128016 | ZFP36 |
| ENSG00000130066 | SAT1 |
| ENSG00000130303 | BST2 |
| ENSG00000130638 | ATXN10 |
| ENSG00000131238 | PPT1 |
| ENSG00000131389 | SLC6A6 |
| ENSG00000131711 | MAP1B |
| ENSG00000131724 | IL13RA1 |
| ENSG00000131979 | GCH1 |
| ENSG00000132002 | DNAJB1 |
| ENSG00000132294 | EFR3A |
| ENSG00000132530 | XAF1 |
| ENSG00000134001 | EIF2S1 |
| ENSG00000134321 | RSAD2 |
| ENSG00000134326 | CMPK2 |
| ENSG00000134470 | IL15RA |
| ENSG00000135046 | ANXA1 |
| ENSG00000135114 | OASL |
| ENSG00000135148 | TRAFD1 |
| ENSG00000136514 | RTP4 |
| ENSG00000137331 | IER3 |
| ENSG00000137575 | SDCBP |
| ENSG00000137628 | DDX60 |
| ENSG00000137824 | FAM82A2 |
| ENSG00000137965 | IFI44 |
| ENSG00000138032 | PPM1B |
| ENSG00000138642 | HERC6 |
| ENSG00000139318 | DUSP6 |
| ENSG00000139684 | ESD |
| ENSG00000140105 | WARS |
| ENSG00000140416 | TPM1 |
| ENSG00000141753 | IGFBP4 |
| ENSG00000141971 | FAM125A |
| ENSG00000142089 | IFITM3 |
| ENSG00000142657 | PGD |
| ENSG00000143322 | ABL2 |
| ENSG00000143384 | MCL1 |
| ENSG00000143753 | DEGS1 |
| ENSG00000143870 | PDIA6 |
| ENSG00000144381 | HSPD1 |
| ENSG00000144655 | CSRNP1 |
| ENSG00000145741 | BTF3 |
| ENSG00000146872 | TLK2 |
| ENSG00000148677 | ANKRD1 |
| ENSG00000149948 | HMGA2 |
| ENSG00000150093 | ITGB1 |
| ENSG00000150459 | SAP18 |
| ENSG00000151491 | EPS8 |
| ENSG00000151694 | ADAM17 |
| ENSG00000152894 | PTPRK |
| ENSG00000152952 | PLOD2 |
| ENSG00000153071 | DAB2 |
| ENSG00000153827 | TRIP12 |
| ENSG00000154589 | LY96 |
| ENSG00000156467 | UQCRB |
| ENSG00000157654 | PALM2-AKAP2 |
| ENSG00000158417 | EIF5B |
| ENSG00000159176 | CSRP1 |
| ENSG00000159200 | RCAN1 |
| ENSG00000159216 | RUNX1 |
| ENSG00000160209 | PDXK |
| ENSG00000160255 | ITGB2 |
| ENSG00000161057 | PSMC2 |
| ENSG00000161133 | USP41 |
| ENSG00000162521 | RBBP4 |
| ENSG00000162645 | GBP2 |
| ENSG00000162654 | GBP4 |
| ENSG00000162694 | EXTL2 |
| ENSG00000162735 | PEX19 |
| ENSG00000162772 | ATF3 |
| ENSG00000163512 | AZI2 |
| ENSG00000163564 | PYHIN1 |
| ENSG00000163565 | IFI16 |
| ENSG00000163659 | TIPARP |
| ENSG00000163734 | CXCL3 |
| ENSG00000163739 | CXCL1 |
| ENSG00000163746 | PLSCR2 |
| ENSG00000164053 | ATRIP |
| ENSG00000164111 | ANXA5 |
| ENSG00000164342 | TLR3 |
| ENSG00000164924 | YWHAZ |
| ENSG00000164949 | GEM |
| ENSG00000165806 | CASP7 |
| ENSG00000166710 | B2M |
| ENSG00000167460 | TPM4 |
| ENSG00000167900 | TK1 |
| ENSG00000168092 | PAFAH1B2 |
| ENSG00000168282 | MGAT2 |
| ENSG00000168283 | BMI1 |
| ENSG00000168461 | RAB31 |
| ENSG00000169032 | MAP2K1 |
| ENSG00000169139 | UBE2V2 |
| ENSG00000169245 | CXCL10 |
| ENSG00000169813 | HNRNPF |
| ENSG00000169908 | TM4SF1 |
| ENSG00000169919 | GUSB |
| ENSG00000170385 | SLC30A1 |
| ENSG00000170667 | RASA4B |
| ENSG00000171223 | JUNB |
| ENSG00000171497 | PPID |
| ENSG00000171960 | PPIH |
| ENSG00000173156 | RHOD |
| ENSG00000173221 | GLRX |
| ENSG00000173517 | PEAK1 |
| ENSG00000174437 | ATP2A2 |
| ENSG00000174640 | SLCO2A1 |
| ENSG00000174775 | HRAS |
| ENSG00000175592 | FOSL1 |
| ENSG00000177888 | ZBTB41 |
| ENSG00000177889 | UBE2N |
| ENSG00000178053 | MLF1 |
| ENSG00000178209 | PLEC |
| ENSG00000178719 | GRINA |
| ENSG00000180370 | PAK2 |
| ENSG00000180398 | MCFD2 |
| ENSG00000180628 | PCGF5 |
| ENSG00000184371 | CSF1 |
| ENSG00000184557 | SOCS3 |
| ENSG00000184979 | USP18 |
| ENSG00000184988 | TMEM106A |
| ENSG00000185201 | IFITM2 |
| ENSG00000185215 | TNFAIP2 |
| ENSG00000185507 | IRF7 |
| ENSG00000185885 | IFITM1 |
| ENSG00000185896 | LAMP1 |
| ENSG00000186283 | TOR3A |
| ENSG00000187735 | TCEA1 |
| ENSG00000188157 | AGRN |
| ENSG00000188313 | PLSCR1 |
| ENSG00000196233 | LCOR |
| ENSG00000197045 | GMFB |

TABLE 1(a)-continued

| Ensembl Gene ID | Gene Name |
|---|---|
| ENSG00000197063 | MAFG |
| ENSG00000198033 | TUBA3C |
| ENSG00000198060 | MARCH5 |
| ENSG00000198498 | TMA16 |
| ENSG00000198931 | APRT |
| ENSG00000204010 | IFIT1B |
| ENSG00000204264 | PSMB8 |
| ENSG00000205220 | PSMB10 |
| ENSG00000213281 | NRAS |
| ENSG00000213512 | GBP7 |
| ENSG00000213689 | TREX1 |
| ENSG00000213853 | EMP2 |
| ENSG00000215301 | DDX3X |
| ENSG00000217555 | CKLF |
| ENSG00000221914 | PPP2R2A |
| ENSG00000229644 | NAMPTL |
| ENSG00000237693 | IRGM |
| ENSG00000240065 | PSMB9 |
| ENSG00000241978 | AKAP2 |
| ENSG00000254788 | CKLF-CMTM1 |

TABLE 1(b)

| Ensembl Gene ID | Gene Name | Ensembl Gene ID | Gene Name |
|---|---|---|---|
| ENSG00000114013 | CD86 | ENSG00000122786 | CALD1 |
| ENSG00000020633 | RUNX3 | | LER3 |
| | IFI202B | ENSG00000163131 | CTSS |
| ENSG00000137801 | THBS1 | ENSG00000150540 | HNMT |
| ENSG00000147416 | ATP6V1B2 | ENSG00000009307 | CSDE1 |
| ENSG00000138755 | CXCL9 | ENSG00000100600 | LGMN |
| ENSG00000140157 | NIPA2 | ENSG00000177426 | TGIF1 |
| ENSG00000126759 | CFP | ENSG00000118520 | ARG1 |
| ENSG00000068366 | ACSL4 | | |

Reference to each of the genes detailed above should be understood as a reference to all forms of these genes and variants thereof. As would be appreciated by the person of skill in the art, some genes are known to exhibit allelic variation between individuals or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the genes described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA which arise from any other mutation, polymorphic or allelic variation.

In terms of the method of the present invention, screening for the "level of expression" of these genes may be achieved in a variety of ways including screening for any of the forms of RNA transcribed from these genes or cDNA generated therefrom or the protein expression product. Reference to "screening for the level of RNA transcripts" should be understood as a reference to either screening the RNA directly or screening cDNA transcribed therefrom. Changes to the levels of any of these products is indicative of changes to the expression of the subject gene. As detailed hereinbefore, the loss of functional IRF7 in tumours which have undergone transition to a metastatic phenotype will lead to a reduction or loss in the expression of all or some of the genes of Table 1. Accordingly, in such samples one would expect to observe a reduction in transcription and therefore a loss of mRNA transcripts and encoded protein expression product. Still further, the nucleic acid molecule or protein which is identified and measured may be a whole molecule or a fragment thereof. For example, one may identify only fragments of RNA, depending on how the sample has been processed. Provided that said fragment comprises sufficient sequence to indicate its origin with a particular gene or protein, fragmented molecules are useful in the context of the method of the present invention.

Reference to "nucleic acid molecule" should be understood as a reference to both deoxyribonucleic acid molecules and ribonucleic acid molecules and fragments thereof. The present invention therefore extends to both directly screening for RNA levels in a sample or screening for the complementary cDNA which has been reverse-transcribed from an RNA population of interest. It is well within the skill of the person of skill in the art to design methodology directed to screening for DNA, RNA or protein.

It is envisioned that any of the genes listed in Table 1 above may be used in the method of the invention either alone or in combination with other genes in Table 1 or other diagnostic markers. Although information concerning the expression of as few as one gene is expected to provide useful information, confidence in the accuracy of the classification of a tumour as metastatic will increase when more markers are included. Tumours may be analysed with respect to the expression of groups of these genes, including from 1 to 10 of the of the genes listed in Table 1, in any combination. It is well within the ability of one of skill in the art to select groups of genes for analysis from among the genes listed in Table 1.

In the interest of brevity, applicants are not expressly listing every possible combination of genes suitable for use in the invention. Nevertheless, it should be understood that every such combination is contemplated and is within the scope of the invention.

In further embodiments, said screening is directed to at least 10 genes, at least 20 genes, at least 30 genes, at least 40 genes, at least 50 genes, at least 60 genes, at least 70 genes, at least 80 genes, at least 90 genes, at least 100 genes, at least 110 genes, at least 120 genes, at least 130 genes, at least 140 genes, at least 150 genes, at least 160 genes, at least 170 genes, at least 180 genes, at least 190 genes, at least 200 genes or at least 208 genes.

In another embodiment, said screening is directed to one or more genes selected from Table 2.

TABLE 2

| Ensembl Gene ID | Gene Name |
|---|---|
| ENSG00000068079 | IFI35 |
| ENSG00000096696 | DSP |
| ENSG00000100368 | CSF2RB |
| ENSG00000108342 | CSF3 |
| ENSG00000108679 | LGALS3BP |
| ENSG00000108771 | DHX58 |
| ENSG00000119917 | IFIT3 |
| ENSG00000130303 | BST2 |
| ENSG00000131979 | GCH1 |
| ENSG00000134321 | RSAD2 |
| ENSG00000134326 | CMPK2 |
| ENSG00000136514 | RTP4 |
| ENSG00000137959 | IFI44L |
| ENSG00000137965 | IFI44 |
| ENSG00000163293 | NIPAL1 |
| ENSG00000163564 | PYHIN1 |
| ENSG00000163565 | IFI16 |

TABLE 2-continued

| Ensembl Gene ID | Gene Name |
| --- | --- |
| ENSG00000164136 | IL15 |
| ENSG00000164342 | TLR3 |
| ENSG00000185507 | IRF7 |
| ENSG00000185745 | IFIT1 |
| ENSG00000204010 | IFIT1B |
| ENSG00000237693 | IRGM |
| ENSG00000122786 | CALD1 |
| ENSG00000114013 | CD86 |
|  | LER3 |
| ENSG00000020633 | RUNX3 |
| ENSG00000163131 | CTSS |
|  | IFI202B |
| ENSG00000150540 | HNMT |
| ENSG00000137801 | THBS1 |
| ENSG00000009307 | CSDE1 |
| ENSG00000147416 | ATP6V1B2 |
| ENSG00000100600 | LGMN |
| ENSG00000138755 | CXCL9 |
| ENSG00000177426 | TGIF1 |
| ENSG00000140157 | NIPA2 |
| ENSG00000118520 | ARG1 |
| ENSG00000126759 | CFP |
| ENSG00000068366 | ACSL4 |

Still another embodiment is directed to a method of assessing the metastatic status of a tumour from an individual, said method comprising detecting the expression of IFITM3, TLR3, IRF7, and IL13RA1 by said tumour wherein a decreased level of expression of said genes relative to the level of expression of said genes in a corresponding non-metastatic tumour is indicative of the metastatic phenotype of said tumour.

Yet another embodiment is directed to a method of assessing the metastatic status of the tumour from an individual, said method comprising detecting the expression of CALD1, RUNX1, YWHAZ and HBEGF by said tumour wherein a decreased level of expression of said genes relative to the level of expression of said genes in a corresponding non-metastatic tumour is indicative of the metastatic phenotype of said tumour.

Still yet another embodiment is directed to a method of assessing the metastatic status of a tumour from an individual, said method comprising detecting the expression of IL13RA1, CSF2RB, STAT1, CD44, IRF7, IFI44, TLR3 and IFITM3 by said tumour wherein a decreased level of expression of said genes relative to the level of expression of said genes in a corresponding non-metastatic tumour is indicative of the metastatic phenotype of said tumour.

Preferably, said method comprises detecting the expression of L13RA1, CD86, CSF2RB, STAT1, CD44, IRF7, IFI44, TLR3, IER3, IFITM3, RUNX3 and CTSS.

Yet still another embodiment is directed to a method of assessing the metastatic status of a tumour from an individual, said method comprising detecting the expression of 1FI44, IRF7, CSF2RB, STAT1, TLR3, IL13RA1 and IFITM3 by said tumour wherein a decreased level of expression of said genes relative to the level of expression of said genes in a corresponding non-metastatic tumour is indicative of the metastatic phenotype of said tumour.

Preferably, said method comprises detecting the expression of IFI44, IRF7, CSF2RB, STAT1, TLR3, IFI202B, IER3, RUNX3, CTSS, IL13RA1, IFITM3 and CD86.

A further embodiment is directed to a method of assessing the metastatic status of a tumour from an individual, said method comprising detecting the expression of RUNX1, SQLE, PDXK, YWHAZ, DDX3X, RBBP4, HBEGF, DAB2 and FAM120A by said tumour wherein a decreased level of expression of said genes relative to the level of expression of said genes in a corresponding non-metastatic tumour is indicative of the metastatic phenotype of said tumour.

Preferably, said method comprises detecting the expression of RUNX1, SQLE, PDXK, HNMT, CALD1, YWHAZ, DDX3X, RBBP4, THBS1, HBEGF, DAB2 and FAM120A.

Another further embodiment is directed to a method of assessing the metastatic status of a tumour from an individual, said method comprising detecting the expression of PTPRK and SLC6A6 by said tumour wherein a decreased level of expression of said genes relative to the level of expression of said genes in a corresponding non-metastatic tumour is indicative of the metastatic phenotype of said tumour.

Preferably, said method comprises detecting the expression of CSDE1, ATP6VIB2, PTPRK, LGMN, CXCL9, TGIF1, NIPA2, SLC6A6, ARG1, CFP, CTSH and ACSL4.

Still another further embodiment is directed to a method of assessing the metastatic status of a tumour from an individual, said method comprising detecting the expression of DHX58, BST2, IFI44, IFIT3, IRF7, STAT1, DSP and USP18 by said tumour wherein a decreased level of expression of said genes relative to the level of expression of said genes in a corresponding non-metastatic tumour is indicative of the metastatic phenotype of said tumour.

In accordance with the previous aspects, in one embodiment said screening method is directed to screening for mRNA or cDNA.

In another embodiment, said screening method is directed to screening for the encoded protein expression product.

It would be appreciated by the person of skill in the art that the gene panels detailed hereinbefore may be screened for as isolated panels or they may form part of a larger panel. That is, one may elect to screen for a given panel together with one or more additional markers.

In relation to IRF7, IRF9 and STAT1, one may screen for localisation of one or more of these proteins to the intranuclear region of a tumour cell, since this would indicate the successful phosphorylation and thereby signalling of the molecule. Alternatively, one can screen for the intracellular presence of the phosphorylated form of the protein. Although one can screen for changes to the absolute levels of these proteins, it should be understood that the cellular defect which leads to metastatic transition is not necessarily a loss of IRF7, IRF9 or STAT1 expression per se. The defect may also be a loss of the functional form of these proteins. In this case, the protein may still be present, albeit not in a functional form.

Without limiting the present invention to any one theory or mode of action, these proteins function by undergoing phosphorylation and thereafter translocation from the cytoplasm to the nucleus. Once in the nucleus, IRF7 and IRF9 bind to the gene promoter in order to induce transcription. Non-functional protein is therefore detectable either by screening for the localisation of the protein, with cytoplasmic localisation being indicative of non-functionality, or phosphorylation, wherein a lack of phosphorylation is indicative of non-functionality. This form of testing may be done together with testing for the absolute levels of protein or for the RNA transcripts of said proteins.

Reference to "IRF7", "IRF9" and "STAT1" should be understood as a reference to all forms of these proteins including any isoforms which arise from alternative splicing, of the subject protein's mRNA or allelic or polymorphic variants.

The subject gene expression or functional protein levels are measured in the cells of the tumour. It would be appreciated by the person of skill in the art that the testing of a tumour to determine its metastatic status will often occur after the tumour has been surgically excised. However, to the extent that surgical excision may not be possible or desirable or to the extent that an immediate result is sought, a biopsy specimen can be harvested either at or immediately after initial diagnosis and the testing can be performed on this specimen.

The results obtained from the tumour of the individual in issue are assessed relative to the level which is present in a corresponding non-metastatic tumour. This is the control level, By "corresponding" is meant a tumour of the same tissue type as the tumour which is the subject of testing. For example, if a breast tissue tumour is the subject of analysis in accordance with the method of the present invention then the control level of gene or protein expression will be that of a non-metastatic breast tissue tumour. The control level may be a standard result which reflects individual or collective results obtained from individuals other than the mammal in issue. This form of analysis is in fact a preferred method of analysis since it enables the design of kits which require the collection and analysis of a single biological sample, being a test sample of interest. The standard results which provide the control level may be calculated by any suitable means which would be well known to the person of skill in the art. For example, a population of non-metastatic tumour tissues can be assessed in terms of the level of gene or protein expression thereby providing a standard value or range of values against which all future test samples are analysed. It should also be understood that this control level may be determined from the subjects of a specific cohort and for use with respect to test samples derived from that cohort. Accordingly, there may be determined a number of standard values or ranges which correspond to cohorts which differ in respect of characteristics such as age, gender, ethnicity or health status. It is to be expected that standards would be developed for each tissue type in which a tumour can arise. Said "control level" may be a discrete level or a range of levels.

The biological sample which is tested according to the method of the present invention may be tested directly or may require some form of treatment prior to testing. For example, a tissue sample may require homogenisation prior to testing or it may require sectioning for in situ testing of the intracellular localisation of proteins. Alternatively, a cell sample may require permeabilisation prior to testing. Further, to the extent that the biological sample is not in liquid form, (if such form is required for testing) it may require the addition of a reagent, such as a buffer, to mobilise the sample.

The biological sample may be directly tested or else all or some of the nucleic acid or protein material present in the biological sample may be isolated prior to testing. To this end, it would be appreciated that when screening for changes to the level of expression of the genes in Table 1, one may screen for the RNA transcripts themselves or cDNA which has been transcribed therefrom. In yet another example, the sample may be partially purified or otherwise enriched prior to analysis. It is within the scope of the present invention for the target cell population or molecules derived therefrom to be pretreated prior to testing, for example, inactivation of live virus or being run on a gel. It should also be understood that the biological sample may be freshly harvested or it may have been stored (for example by freezing) prior to testing or otherwise treated prior to testing (such as by undergoing culturing).

The term "individual" or "patient" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably the mammal is a human or a laboratory test animal. Even more preferably, the mammal is a human.

It should be understood that the decrease in the level of expression of the subject molecules, in a tumour which has transitioned to a metastatic phenotype, may be either a partial reduction in the level of expression relative to control levels or it may be a complete absence of expression. It should also be understood that the degree of reduction in expression may vary between genes. Accordingly to the extent that six or more of the genes of Table 1 are tested, the degree to which expression levels are reduced as between the genes may differ. However, the critical issue is that the levels of each gene will be reduced relative to its corresponding control. It should also be expected that as between different patients with the same type of primary tumour being tested, there may be observed variation in the degree of reduction of expression of the genes which are tested. However, provided that the observed level is below the non-metastatic tumour control level, this is indicative of the shift to a metastatic phenotype.

Means for testing for changes to the expression levels of one or more of the genes listed in Table 1 in a tumour sample can be achieved by any suitable method, which would be well known to the person of skill in the art, such as but not limited to assessment of expression profiles of RNA by array technologies (Alon et al., *Proc. Natl. Acad. Sci. USA:* 96, 6745-6750, June 1999).

A "microarray" is a linear or multi-dimensional array of preferably discrete regions, each having a defined area, formed on the surface of a solid support. The density of the discrete regions on a microarray is determined by the total numbers of target polynucleotides to be detected on the surface of a single solid phase support. As used herein, a DNA microarray is an array of oligonucleotide probes placed onto a chip or other surfaces used to detect complementary oligonucleotides from a complex nucleic acid mixture. Since the position of each particular group of probes in the array is known, the identities of the target polynucleotides can be determined based on their binding to a particular position in the microarray.

DNA microarray technology makes it possible to conduct a large scale assay of a plurality of target nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells or tissues, often a tissue of interest and a control tissue, is compared and any differences in gene expression among the respective tissues are identified. Such information is useful for the identification of the types of genes expressed in a particular tissue type and diagnosis of conditions based on the expression profile.

In one example, RNA from the sample of interest is subjected to reverse transcription to obtain labelled cDNA. See U.S. Pat. No. 6,410,229 (Lockhart et al.) The cDNA is then hybridized to oligonucleotides or cDNAs of known sequence arrayed on a chip or other surface in a known order. In another example, the RNA is isolated from a biological sample and hybridised to a chip on which are anchored cDNA probes. The location of the oligonucleotide to which the labelled cDNA hybridizes provides sequence information on the cDNA, while the amount of labelled hybridized RNA or cDNA provides an estimate of the relative representation of the RNA or cDNA of interest. See Schena et al. *Science* 270:467-470 (1995). For example, use of a cDNA microarray to analyze gene expression patterns in human cancer is described by DeRisi, et al. (*Nature Genetics* 14:457-460 (1996)).

In one embodiment, nucleic acid probes corresponding to the subject nucleic acids are made. The nucleic acid probes attached to the microarray are designed to be substantially complementary to the nucleic acids of the biological sample such that specific hybridization of the target sequence and the probes of the present invention occurs. This complementarity need not be perfect, in that there may be any number of base pair mismatches that will interfere with hybridization between the target sequence and the single stranded nucleic acids of the present invention. It is expected that the overall homology of the genes at the nucleotide level probably will be about 40% or greater, probably about 60% or greater, and even more probably about 80% or greater; and in addition that there will be corresponding contiguous sequences of about 8-12 nucleotides or longer. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions.

A nucleic acid probe is generally single stranded but can be partly single and partly double stranded. The strandedness of the probe is dictated by the structure, composition, and properties of the target sequence. In general, the oligonucleotide probes range from about 6, 8, 10, 12, 15, 20, 30 to about 100 bases long, with from about 10 to about 80 bases being preferred, and from about 15 to about 40 bases being particularly preferred. That is, generally entire genes are rarely used as probes. In some embodiments, much longer nucleic acids can be used, up to hundreds of bases. The probes are sufficiently specific to hybridize to a complementary template sequence under conditions known by those of skill in the art. The number of mismatches between the probe's sequences and their complementary template (target) sequences to which they hybridize during hybridization generally do not exceed 15%, usually do not exceed 10% and preferably do not exceed 5%, as-determined by BLAST (default settings).

Oligonucleotide probes can include the naturally-occurring heterocyclic bases normally found in nucleic acids (uracil, cytosine, thymine, adenine and guanine), as well as modified bases and base analogues. Any modified base or base analogue compatible with hybridization of the probe to a target sequence is useful in the practice of the invention. The sugar or glycoside portion of the probe can comprise deoxyribose, ribose, and/or modified forms of these sugars, such as, for example, 2'-O-alkyl ribose. In a preferred embodiment, the sugar moiety is 2'-deoxyribose; however, any sugar moiety that is compatible with the ability of the probe to hybridize to a target sequence can be used.

In one embodiment, the nucleoside units of the probe are linked by a phosphodiester backbone, as is well known in the art. In additional embodiments, internucleotide linkages can include any linkage known to one of skill in the art that is compatible with specific hybridization of the probe including, but not limited to phosphorothioate, methylphosphonate, sulfamate (e.g., U.S. Pat. No. 5,470,967) and polyamide (i.e., peptide nucleic acids). Peptide nucleic acids are described in Nielsen et al. (1991) *Science* 254: 1497-1500, U.S. Pat. No. 5,714,331, and Nielsen (1999) *Curr. Opin. Biotechnol.* 10:71-75.

In certain embodiments, the probe can be a chimeric molecule; i.e., can comprise more than one type of base or sugar subunit, and/or the linkages can be of more than one type within the same primer. The probe can comprise a moiety to facilitate hybridization to its target sequence, as are known in the art, for example, intercalators and/or minor groove binders. Variations of the bases, sugars, and internucleoside backbone, as well as the presence of any pendant group on the probe, will be compatible with the ability of the probe to bind, in a sequence-specific fashion, with its target sequence. A large number of structural modifications, are possible within these bounds. Advantageously, the probes according to the present invention may have structural characteristics such that they allow the signal amplification, such structural characteristics being, for example, branched DNA probes as those described by Urdea et al. (*Nucleic Acids Symp. Ser.*, 24:197-200 (1991)) or in the European Patent No. EP-0225,807. Moreover, synthetic methods for preparing the various heterocyclic bases, sugars, nucleosides and nucleotides that form the probe, and preparation of oligonucleotides of specific predetermined sequence, are well-developed and known in the art. A preferred method for oligonucleotide synthesis incorporates the teaching of U.S. Pat. No. 5,419,966.

Multiple probes may be designed for a particular target nucleic acid to account for polymorphism and/or secondary structure in the target nucleic acid, redundancy of data and the like. In some embodiments, where more than one probe per sequence is used, either overlapping probes or probes to different sections of a single target gene are used. That is, two, three, four or more probes, are used to build in a redundancy for a particular target. The probes can be overlapping (i.e. have some sequence in common), or are specific for distinct sequences of a gene. When multiple target polynucleotides are to be detected according to the present invention, each probe or probe group corresponding to a particular target polynucleotide is situated in a discrete area of the microarray.

Probes may be in solution, such as in wells or on the surface of a micro-array, or attached to a solid support. Examples of solid support materials that can be used include a plastic, a ceramic, a metal, a resin, a gel and a membrane. Useful types of solid supports include plates, beads, magnetic material, microbeads, hybridization chips, membranes, crystals, ceramics and self-assembling monolayers. One example comprises a two-dimensional or three-dimensional matrix, such as a gel or hybridization chip with multiple probe binding sites (Pevzner et al., *J. Biomol. Struc. & Dyn.* 9:399-410, 1991; Maskos and Southern, *Nuc. Acids Res.* 20:1679-84, 1992). Hybridization chips can be used to construct very large probe arrays that are subsequently hybridized with a target nucleic acid. Analysis of the hybridization pattern of the chip can assist in the identification of the target nucleotide sequence. Patterns can be manually or computer analyzed, but it is clear that positional sequencing by hybridization lends itself to computer analysis and automation. In another example, one may use an Affymetrix chip on a solid phase structural support in combination with a fluorescent bead based approach. In yet another example, one may utilise a cDNA microarray. In this regard, the oligonucleotides described by Lockkart et al. (i.e. Affymetrix synthesis probes in situ on the solid phase) are particularly preferred, that is, photolithography.

As will be appreciated by those in the art, nucleic acids can be attached or immobilized to a solid support in a wide variety of ways. By "immobilized" herein is meant the association or binding between the nucleic acid probe and the solid support is sufficient to be stable under the conditions of binding, washing, analysis, and removal. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as streptavidin, to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

Nucleic acid probes may be attached to the solid support by covalent binding such as by conjugation with a coupling agent or by covalent or non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (T. Sano and C. R. Cantor, *Bio/Technology* 9:1378-81 (1991)), or derivatives or combinations of these agents. Nucleic acids may be attached to the solid support by a photocleavable bond, an electrostatic bond, a disulfide bond, a peptide bond, a diester bond or a combination of these sorts of bonds. The array may also be attached to the solid support by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

In general, the probes are attached to the microarray in a wide variety of ways, as will be appreciated by those in the art. As described herein, the nucleic acids can either be synthesized first, with subsequent attachment to the microarray, or can be directly synthesized on the microarray.

The microarray comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. The solid phase support of the present invention can be of any solid materials and structures suitable for supporting nucleotide hybridization and synthesis. Preferably, the solid phase support comprises at least one substantially rigid surface on which the primers can be immobilized and the reverse transcriptase reaction performed. The substrates with which the polynucleotide microarray elements are stably associated and may be fabricated from a variety of materials, including plastics, ceramics, metals, acrylamide, cellulose, nitrocellulose, glass, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates may be two-dimensional or three-dimensional in form, such as gels, membranes, thin films, glasses, plates, cylinders, beads, magnetic beads, optical fibers, woven fibers, etc. A preferred form of array is a three-dimensional array. A preferred three-dimensional array is a collection of tagged beads. Each tagged bead has different primers attached to it. Tags are detectable by signalling means such as color (Luminex, Illumina) and electromagnetic field (Pharmaseq) and signals on tagged beads can even be remotely detected (e.g., using optical fibers). The size of the solid support can be any of the standard microarray sizes, useful for DNA microarray technology, and the size may be tailored to fit the particular machine being used to conduct a reaction of the invention. In general, the substrates allow optical detection and do not appreciably fluoresce.

In one embodiment, the surface of the microarray and the probe may be derivatized with chemical functional groups for subsequent attachment of the two. Thus, for example, the microarray is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known. In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside. In an additional embodiment, the immobilization to the solid support may be very strong, yet non-covalent. For example, biotinylated oligonucleotides can be made, which bind to surfaces covalently coated with streptavidin, resulting in attachment.

The arrays may be produced according to any convenient methodology, such as preforming the polynucleotide microarray elements and then stably associating them with the surface. Alternatively, the oligonucleotides may be synthesized on the surface, as is known in the art. A number of different array configurations and methods for their production are known to those of skill in the art and disclosed in WO 95/25116 and WO 95/35505 (photolithographic techniques), U.S. Pat. No. 5,445,934 (in situ synthesis by photolithography), U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference. Another method for coupling DNA to beads uses specific ligands attached to the end of the DNA to link to ligand-binding molecules attached to a bead. Possible ligand-binding partner pairs include biotin-avidin/streptavidin, or various antibody/antigen pairs such as digoxygenin-antidigoxygenin antibody (Smith et al., *Science* 258:1122-1126 (1992)). Covalent chemical attachment of DNA to the support can be accomplished by using standard coupling agents to link the 5'-phosphate on the DNA to coated microspheres through a phosphoamidate bond. Methods for immobilization of oligonucleotides to solid-state substrates are well established. See Pease et al., *Proc. Natl. Acad. Sci. USA* 91(11):5022-5026 (1994). A preferred method of attaching oligonucleotides to solid-state substrates is described by Guo et al., *Nucleic Acids Res.* 22:5456-5465 (1994). Immobilization can be accomplished either by in situ DNA synthesis (Maskos and Southern, supra) or by covalent attachment of chemically synthesized oligonucleotides (Guo et al., supra) in combination with robotic arraying technologies.

In addition to the solid-phase technology represented by microarray arrays, gene expression can also be quantified using liquid-phase assays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Green 1, is an example of an intercalating dye, that preferentially binds to dsDNA resulting in a concomitant increase in the fluorescent signal. Sequence specific probes, such as used with TaqMan technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signalling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, an array of probe/primer reactions can simultaneously quantify the expression of multiple gene products of interest. See Germer et al., *Genome Res.* 10:258-266 (2000); Heid et al., *Genome Res.* 6:986-994 (1996).

Means for testing for changes to the functional levels of the IRF7, IRF9 and STAT I proteins can also be achieved by any suitable method which would be well known to the person of skill in the art. For example, screening for the intracellular localisation of a protein can be achieved by simple immunohistochemistry.

Examples of suitable methods include, but are not limited to, antibody screening of tissue sections or biopsy specimens.

To the extent that antibody based methods of diagnosis are used, the presence of the marker protein may be determined in a number of ways such as by Western blotting, ELISA or flow cytometry procedures. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the marker or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking, covalently binding or physically adsorbing, the polymer-antibody complex is washed in preparation for the test sample. An aliquot of the sample to be tested is then added to the solid phase complex and incubated for a period of time sufficient (e.g. 2-40 minutes) and under suitable conditions (e.g. 25° C.) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the antigen.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence, observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

To the extent that one elects to screen for the phosphorylation status of these proteins, this can be achieved either qualitatively or quantitatively. At its simplest, assessment by eye of the intensity of a band which has developed, such, as on an autoradiograph following incorporation of a radioactive phosphate (e.g. [$^{32}$P]-γATP) or immunoblotting using an antibody that specifically recognises the phosphorylated residue, in isolation (i.e. the presence/absence of any phosphorylation) or relative to a control test may be performed, wherein a darker and/or thicker band is indicative of a higher level of phosphorylation than a fainter and/or thinner band. A corresponding type of analysis can be qualitatively or quantitatively performed with reporter readouts. More sophisticated analysis can be performed utilising equipment such as a densitometer based on visible light or fluorescence, which can empirically calculate the concentration of a phosphorylated protein in a given band relative to a standard.

In a related aspect, the present findings have enabled the development of means for treating metastatic cancer. It should be understood that the method of this aspect of the present invention is best used as an adjunct therapy to whatever treatment regime has been selected to target the primary tumour. For example, it may be that the primary tumour is surgically removed and the subject treatment method is subsequently applied in order to therapeutically treat metastatic disease. In another example, the primary tumour may not be surgically removable and is being treated by radiation therapy while nevertheless simultaneously treating the patient for metastatic turnouts using the present method. It would be appreciated by the skilled person that the application of the method of the present invention is generally going to be indicated after analysis of the primary tumour has revealed a shift to a metastatic phenotype.

Without limiting the present invention in any way, it would be appreciated that the diagnostic method herein disclosed identifies the shift to a metastatic phenotype, in some cases metastatic spread may already have commenced while in other clinical situations, although the shift to a metastatic phenotype may have occurred, the actual spread of primary tumour cells to other organs may not yet have occurred. It is to be expected that other than in the more advanced stages of metastatic cancer, where the metastatic tumours become more highly visible, one may not be able to confirm whether or not metastatic spread of the primary tumour has occurred. Accordingly, the method of the present invention may be functioning prophylactically, such as where a primary tumour exhibiting a metastatic phenotype cannot be surgically removed but has not yet actually spread, or it may be functioning therapeutically, such as where metastatic spread has commenced, even if these metastases are not yet detectable by conventional diagnostic techniques.

Although the treatment method of this aspect of the present invention has utility in the treatment of either advanced stage or early stage metastatic disease, its application in preventing or treating early stage metastases is particularly significant since this provides a means of potentially preventing a patient from reaching the point of advanced disease, which can be both debilitating and lead to poorer prognostic outcomes due to the range of other clinical problems which are associated with advanced stage disease and which can render late stage treatments less effective. To date there has not been an effective means of treating metastatic disease. Chemotherapy is the primary treatment used to date, this being very non-specific and of only moderate effectiveness. Clinicians have also been reluctant to subject patients to this treatment regime, due to its side effects, where there has been no clinical indication of metastatic disease. Often it is the case that by the time metastases are diagnosable, though, they are relatively advanced and the prognosis is poor. The fact that the method of the present invention has now, for the first time, provided both a means to accurately and simply determine, even at the very early stages, whether a primary tumour has become metastatic and a means to treat the metastatic tumours based on a treatment regime which targets the specific defect in these cells, being non-functional IRF7, is a significant step forward in the field of oncology.

As detailed hereinbefore, the present invention is predicated on the determination that the loss of functional IRF7 in a primary tumour induces a shift to a metastatic phenotype. Accordingly, in addition to the fact that a diagnostic method has been developed based on screening for the status of the IRF7 related gene signature in primary tumours, it has also been determined that restoration of the IRF7 pathway provides an effective treatment regime.

Accordingly, this aspect of the present invention is directed to a method of treating metastatic cancer in an individual, which cancer is characterised by aberrant IRF7 functionality, said method comprising administering an effective amount of a composition, wherein said composition comprises an agent which upregulates the level of Type I IFN in said individual.

Reference to "aberrant IRF7 functionality" should be understood as a reference to a metastatic cancer which derives from a primary tumour of the type diagnosable by the method of the first aspect of the present invention. That is, briefly, IRF7 has become non-functional or less functional within the primary tumour and has therefore resulted in the shift of the tumour to a metastatic phenotype. This is diagnostically characterised by a loss of expression of 6 or more genes of Table 1 by the tumour cells or a reduction in the functional levels of IRF7, IRF9 and STAT1. Without limiting the present invention to any one theory or mode of action, patients exhibiting this defect in a primary tumour have been determined to respond favourably to Type I IFN therapy which acts to restore IRF7 pathway functionality, thereby effectively treating metastatic disease.

Reference to "metastatic" and "individual" should be understood to have the same meaning as hereinbefore defined.

In one embodiment said metastatic cancer is a cancer of the breast, colon, kidney, lungs, skin, ovary, pancreas, prostate, rectum, stomach, thyroid or uterus.

In another embodiment the present invention is more particularly directed to a method of treating a breast, kidney or prostate metastatic cancer in an individual, which cancer is characterised by aberrant IRF7 functionality, said method comprising administering an effective amount of a composition, wherein said composition comprises an agent which upregulates the level of Type I IFN in said individual.

Reference to a "breast, kidney, prostate" or other metastatic cancer should be understood as a reference to a metastatic cancer which has arisen from a primary tumour present in one of these organs. The present invention is not limited to these organs, however, can extend to metastatic cancers arising from any organ, such as those mentioned hereinbefore, which are characterised by a loss of IRF7 functionality, this now being routinely diagnosable.

In another embodiment there is provided a method of treating metastatic cancer, which metastases are present in the bone and which cancer is characterised by aberrant IRF7 functionality, in an individual, said method comprising administering an effective amount of a composition, wherein said composition comprises an agent which upregulates the level if Type I IFN in said individual.

Without limiting the present invention to any one theory or mode of action, human Type I IFNs bind to a specific cell surface receptor complex known as the IFN-α receptor (IFNAR) that consists of IFNAR1 and IFNAR2 chains. The mammalian Type I IFNs are designated IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin). Reference to "Type I IFN" should therefore be understood as a reference to any interferon type which falls within this class including all precursor, proprotein, or intermediate forms. it also includes reference to any isoforms which may arise from alternative splicing of Type I IFN mRNA or polymorphic forms of a Type I IFN. Reference to Type I IFN extends to any Type I IFN protein, whether existing as a dimer, multimer or fusion protein. In one embodiment, said Type I IFN is IFN-α or IFN-β.

Accordingly, in one embodiment there is provided a method of treating metastatic cancer in a patient which cancer is characterised by aberrant IRF7 functionality, said method comprising administering an effective amount of a composition, wherein said composition comprises an agent which upregulates the level of IFN-α in said patient.

In another embodiment there is provided a method of treating metastatic cancer in an individual which cancer is characterised by aberrant IRF7 functionality, said method comprising administering an effective amount of a composition wherein said composition comprises an agent which upregulates the level of IFN-β in said individual.

An "effective amount" means an amount necessary at least partly to attain the desired immune response, or to prevent or to delay the onset or inhibit progression or halt altogether, the onset or progression of a particular condition being treated. This amount varies depending upon the health and physical condition of the individual to be treated, the taxonomic group of the individual to be treated, the capacity of the individual's immune system to stimulate a specific immune response, the degree of protection desired, the formulation of the vaccine, the assessment of the medical situation, and other relevant factors. It is expected that the amount will fall in a relatively broad range that can be determined through routine trials.

In a related aspect there is provided the use of an agent which upregulates the level of Type I IFN in the manufacture of a medicament for the treatment of a metastatic cancer in an individual, which cancer is characterised by aberrant IRF7 functionality.

In one embodiment said metastatic cancer is a cancer of the breast, colon, kidney, lungs, skin, ovary, pancreas, prostate, rectum, stomach, thyroid or uterus.

In another embodiment, said cancer is characterised by the onset of bone metastases.

In still another embodiment, said Type I IFN is IFN-α or IFN-β.

In terms of the agent which upregulates the level of Type I IFN, this can be any suitable molecule including, but not limited to:

(i) the Type I IFN protein or functional fragment thereof;

(ii) a nucleic acid molecule encoding Type I IFN or functional fragment thereof;

(iii) a proteinaceous or non-proteinaceous molecule which upregulates the expression of Type I IFN such as by modulating the transcriptional or translational regulation of the Type I IFN gene;

(iv) a proteinaceous or non-proteinaceous molecule which interacts with a Pattern Recognition receptor such as the Toll-like receptor including, for example, the TLR7/8 agonist imiquimod.

The proteinaceous molecules described above may be derived from any suitable source such as natural, recombinant or synthetic sources and includes fusion proteins or molecules which have been identified following, for example, natural product screening. The reference to non-proteinaceous molecules may be, for example, a reference to a nucleic acid molecule or it may be a molecule derived from natural sources, such as for example natural product screening, or may be a chemically synthesised molecule. The present invention contemplates analogues of Type I IFN expression product or small molecules capable of acting as agonists. Chemical agonists may not necessarily be derived from the Type I IFN expression product but may share certain conformational similarities. Alternatively, chemical agonists may be specifically designed to meet certain physiochemical properties.

The proteinaceous and non-proteinaceous molecules referred to in points (i)-(iv), above, are herein collectively referred to as "modulatory agents".

Screening for the modulatory agents hereinbefore defined can be achieved by any one of several suitable methods including, but in no way limited to, contacting a cell comprising the Type I IFN gene or functional equivalent or derivative thereof with an agent and screening for the modulation of Type I IFN protein production or functional activity, modulation of the expression of a nucleic acid molecule encoding Type I IFN or modulation of the activity or expression of a downstream Type I IFN cellular target. Detecting such modulation can be achieved utilising techniques such as Western blotting, electrophoretic mobility shift assays and/or the readout of reporters of Type I IFN activity such as luciferases, CAT and the like.

It should be understood that the Type I IFN gene or functional equivalent or derivative thereof may be naturally occurring in the cell which is the subject of testing or it may have been transfected into a host cell for the purpose of testing. Further, to the extent that a Type I IFN nucleic acid molecule is transfected into a cell, that molecule may comprise the entire Type I IFN gene or it may merely comprise a portion of the gene such as the portion which regulates expression of the Type I IFN product. For example, the Type I IFN promoter region may be transfected into the cell which is the subject of testing. In this regard, where only the promoter is utilised, detecting modulation of the activity of the promoter can be achieved, for example, by ligating the promoter to a reporter gene. For example, the promoter may be ligated to luciferase or a CAT reporter, the modulation of expression of which gene can be detected via modulation of fluorescence intensity or CAT reporter activity, respectively. Yet another example includes Type I IFN binding sites ligated to a minimal reporter.

These methods provide a mechanism for performing high throughput screening of putative modulatory agents such as the proteinaceous or non-proteinaceous agents comprising synthetic, combinatorial, chemical and natural libraries. These methods will also facilitate the detection of agents which bind either the Type I IFN nucleic acid molecule or expression product itself or which modulate the expression of an upstream molecule, which upstream molecule subsequently modulates Type I IFN expression or expression product activity. Accordingly, these methods provide a mechanism of detecting agents which either directly or indirectly modulate Type I IFN expression and/or activity.

The agents which are utilised in accordance with the method of the present invention may take any suitable form. For example, proteinaceous agents may be glycosylated or unglycosylated, phosphorylated or dephosphorylated to various degrees and/or may contain a range of other molecules used, linked, bound or otherwise associated with the proteins such as amino acids, lipid, carbohydrates or other peptides, polypeptides or proteins. Similarly, the subject non-proteinaceous molecules may also take any suitable form. Both the proteinaceous and non-proteinaceous agents herein described may be linked, bound otherwise associated with any other proteinaceous or non-proteinaceous molecules. For example, in one embodiment of the present invention said agent is associated with a molecule which permits its targeting to a localised region.

The subject proteinaceous or non-proteinaceous molecule may act either directly or indirectly to modulate the expression of Type I IFN or the activity of the Type I IFN expression product. Said molecule acts directly if it associates with the Type I IFN nucleic acid molecule or expression product to modulate expression or activity, respectively. Said molecule acts indirectly if it associates with a molecule other than the Type I IFN nucleic acid molecule or expression product which other molecule either directly or indirectly modulates, the expression or activity of the Type I IFN nucleic acid molecule or expression product, respectively. Accordingly, the method of the present invention encompasses the regulation of Type I IFN nucleic acid molecule expression or expression product activity via the induction of a cascade of regulatory steps.

"Derivatives" of the molecules herein described include fragments, parts, portions or variants from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, active regions of the molecule. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Derivatives also include fragments having particular epitopes or parts of the entire protein fused to peptides, polypeptides or other proteinaceous or non-proteinaceous molecules. Analogues of the molecules contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Derivatives of nucleic acid sequences which may be utilised in accordance with the method of the present invention may similarly be derived from single or multiple nucleotide substitutions, deletions and/or additions including fusion with other nucleic acid molecules. The derivatives of the nucleic acid molecules utilised in the present invention include oligonucleotides, PCR primers, antisense molecules, molecules suitable for use in cosuppression and fusion of nucleic acid molecules. Derivatives of nucleic acid sequences also include degenerate variants.

A "variant" or "mutant" of Type I IFN should be understood to mean molecules which exhibit at least some of the functional activity of the form of Type I IFN of which it is a variant or mutant. A variation or mutation may take any form and may be naturally or non-naturally occurring.

A "homologue" is meant that the molecule is derived from a species other than that which is being treated in accordance with the method of the present invention. This may occur, for example, where it is determined that a species other than that which is being treated produces a form of Type I IFN, for example, which exhibits similar and suitable functional characteristics to that of the Type I IFN which is naturally produced by the subject undergoing treatment.

Chemical and functional equivalents should be understood as molecules exhibiting any one or more of the functional activities of the subject molecule, which functional equivalents may be derived from any source such as being chemically synthesised or identified via screening processes such as natural product screening. For example chemical or functional equivalents can be designed and/or identified utilising well known methods such as combinatorial chemistry or high throughput screening of recombinant libraries or following natural product screening.

For example, libraries containing small organic molecules may be screened, wherein organic molecules having a large number of specific parent group substitutions are used. A general synthetic scheme may follow published methods (eg., Bunin B A, et al. (1994) *Proc. Natl. Acad. Sci. USA*, 91:4708-471.2; DeWitt S H, et al. (1993) *Proc. Natl. Acad. Sci. USA,* 90:6909-6913). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing Type I IFN analogues which exhibit properties such as more potent pharmacological effects. Type I IFN or a functional part thereof may according to the present invention be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practising the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

Analogues of Type I IFN contemplated herein include, but are not limited to, modifications to side chains, incorporating unnatural amino acids and/or derivatives during peptide, polypeptide or protein synthesis and the use of crosslinkers and other methods which impose conformational constraints on the analogues. The specific form which such modifications can take will depend on whether the subject molecule is proteinaceous or non-proteinaceous. The nature and/or suitability of a particular modification can be routinely determined by the person of skill in the art.

Modulation of said Type I IFN functional levels may be achieved via the administration of Type I IFN, a nucleic acid molecule encoding Type I IFN or an agent which effects modulation of Type I IFN activity or Type I IFN gene expression (herein collectively referred to as "modulatory agents").

Administration of a composition of the present invention in the form of a pharmaceutical composition, may be performed by any convenient means. The components of the pharmaceutical composition are contemplated to exhibit therapeutic or prophylactic activity when administered in an amount which depends on the particular case. The variation depends, for example, on the human or animal. A broad range of doses may be applicable. Dosage regimes may be adjusted to provide the optimum therapeutic response. For example, several divided doses may be administered daily, weekly, monthly or other suitable time intervals or the dose may be proportionally reduced as indicated by the exigencies of the situation.

The composition may be administered in a convenient manner such as by the oral, inhaled, intraperitoneal, subcutaneous, suppository routes or implanting (e.g. using slow release molecules). It may also be administered via non-mucosal routes, where appropriate, such as via intravenous or other such routes. The composition may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

The modulatory agents of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled the art would appreciate that the choice of a pharmaceutically acceptable carrier including a physiologically acceptable compound depends, for example, on the route of administration of the peptide or polypeptide of the invention and on its particular physio-chemical characteristics.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed. A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

The composition of the invention, when administered orally, can be protected from digestion. This can be accomplished either by complexing the composition with a composition to render it resistant to acidic and enzymatic hydrolysis or by packaging these molecules in an appropriately resistant carrier such as a liposome. Means of protecting compounds from digestion are well known in the art, see, e.g., Fix (1996) *Pharm Res.* 13:1760-1764; Samanen (1996) *J. Pharm. Pharmacol.* 48:119-135; U.S. Pat. No. 5,391,377, describing lipid compositions for oral delivery of therapeutic agents (liposomal delivery is discussed in further detail, infra).

The composition of the invention can also be administered in sustained delivery or sustained release mechanisms, which can deliver the formulation internally. For example, biodegradable microspheres or capsules or other biodegradable polymer configurations capable of sustained delivery of a peptide can be included in the formulations of the invention (see, e.g., Putney (1998) *Nat. Biotechnol.* 16:153-157).

For inhalation, the composition of the invention can be delivered using any system known in the art, including dry powder aerosols, liquid delivery systems, air jet nebulisers, propellant systems, and the like. See, e.g., Patton (1998) *Biotechniques* 16:141-143; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the Type I IFN formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulisers.

The Type I IFN will be formulated in pharmaceutically acceptable compositions suitable for pulmonary or respiratory delivery to a patient. Particular formulations include dry powders, liquid solutions or suspensions suitable for nebulisation, and propellant formulations suitable for use in metered dose inhalers (MDI's). The preparation of such formulations is well described in the patent, scientific, and medical literatures, and the following descriptions are intended to be exemplary only.

Liquid formulations of Type I IFN for use in nebuliser systems can include components to enhance or maintain chemical stability, including chelating agents, protease inhibitors, isotonic modifiers, inert gases, and the like.

For use in metered dose inhalers, the Type I IFN of the present invention will be dissolved or suspended in a suitable aerosol propellant, such as a chlorofluorocarbon (CFC) or a hydrofluorocarbon (HFC). Suitable CFC's include trichloromonofluoromethane (propellant 11), dichlorotetrafluoroethane (propellant 114), and dichlorodifluoromethane (propellant 12). Suitable HFC's include tetrafluoroethane (HFC-134a) and heptafluoropropane (HFC-227).

Preferably, for incorporation into the aerosol propellant, the Type I IFN of the present invention will be processed into respirable particles as described below for the dry powder formulations. The particles are then suspended in the propellant, typically being coated with a surfactant to enhance their dispersion. Suitable surfactants include oleic acid, sorbitan trioleate, and various long chain diglycerides and phospholipids.

Such aerosol propellant formulations may further include a lower alcohol, such as ethanol (up to 30% by weight) and other additives to maintain or enhance chemical stability and physiological acceptability.

Dry powder formulations will typically comprise the Type I IFN in a dry, usually lyophilized, form with a particular size within a preferred range for deposition within the alveolar region of the lung. Respirable powders of Type I IFN within the preferred size range can be produced by a variety of conventional techniques, such as jet-milling, spray-drying, solvent precipitation, and the like. Dry powders can then be administered to the patient in conventional dry powder inhalers (DPI's) that use the inspiratory breath through the device to disperse the powder or in air-assisted devices that use an external power source to disperse the powder into an aerosol cloud.

Dry powder devices typically require a powder mass in the range from about 1 mg to 10 mg to produce a single aerosolized dose ("puff"). Since the required dose of Type I IFN may be lower than this amount, the Type I IFN may be combined with a pharmaceutically acceptable dry bulking powder. Preferred dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like. Typically, suitable buffers and salts may be used to stabilize the Type I IFN in solution prior to particle formation. Suitable buffers include phosphate, citrate, acetate, and tris-HCl, typically at concentrations from about 5 mM to 50 mM. Suitable salts include sodium chloride, sodium carbonate, calcium chloride, and the like. Other additives, such as chelating agents, peptidase inhibitors, and the like, which would facilitate the biological activity of the Type I IFN once it is dissolved within the lung would be appropriate. For example, ethylenediaminetetraacetic acid (EDTA) would be useful as a chelator for divalent cations which are peptidase cofactors.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The pharmaceutical compositions of the invention can be administered in a variety of unit dosage forms depending upon the method of administration. Dosages for typical modulatory pharmaceutical compositions are well known to those of skill in the art. Such dosages are typically advisorial in nature and are adjusted depending on the particular therapeutic context, patient tolerance, etc. The amount of modulatory agent adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton (1997) "Bioavailability and transport of peptides and peptide drugs into the brain" *Peptides* 18:1431-1439; Langer (1990) *Science* 249:1527-1533.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present invention is further described by reference to the following non-limiting examples.

Example 1

Methods
Immunopurification

Immunopurification was performed according to the protocol developed by Parker and colleagues (Parker et al. 2008), with the epithelial selection antibody replaced by α-mouse-Ep-CAM antibody (BD Pharmingen, clone G818). Purity of populations was assessed by RT-PCR analysis for CD31, vWF and P1H12 (endothelial populations), CD45 (haemopoietic populations) and Ep-CAM, CK18 and CK19 (epithelial populations) and NeoR (tumour specific populations) (data not shown).

Microarray Analysis

RNA was extracted using and RNEASY kit (Qiagen, Hilden, Germany). RNA was amplified, labelled and fragmented using a GC Gene Expression 3' Amplification, Two-cycle target labelling kit (Affymetrix, Santa Clara, Calif., USA) with the first In Vitro Transcription performed using an MEGASCRIPT T7 kit (Ambion, Austin, Tex., USA). Affymetrix Mouse 430 v2.0 gene expression arrays were used to determine expression levels. Data analysis was performed in Genespring GX 7.3 (Agilent Technologies, Santa Clara, Calif., USA). Data was imported using an RMA file preprocessor and measurements less than 0.01 were set to 0.01. A per gene normalization of each matched spine metastatic epithelium sample and each primary tumour epithelium sample to the relevant primary tumour epithelium sample was performed. The samples were grouped by tissue type. A confidence filter with the t-test p-value set to 0.05 was used to minimize the number of genes in the data set that did not change expression between the primary tumour epithelium and the metastatic epithelium. An ANOVA (parametric test, not assuming equal variances) with a false discovery rate of 0.03 was used to identify differentially expressed genes. The full data set can be accessed online at GEO. Gene ontology analysis was performed using the gene ontology feature within Genespring GX 7.3, with the ontology table constructed using GenBank, LocusLink and UniGene. A focused promoter analysis using Genomatix (Genomatix Software GmbH, Munchen, Germany) was performed utilizing randomly selected genes from within the top three ontologies. The interferon stimulated response element (ISRE) consensus binding sequence was then used to perform an unfocused promoter analysis on the differentially expressed genes within Genespring GT 1.0 (Agilent Technologies, Santa Clara, Calif., USA) with the sequence data sourced from the MouseGenome9999 sequence file (Agilent Technologies, Santa Clara, Calif., USA).

INTERFEROME Analysis

Expression data was filtered by p value<0.05 and fold-change>2 to identify genes strongly differentially expressed between primary tumour epithelium and the metastatic epithelium. Genes were mapped to Ensembl release 59 gene models and the resulting gene list was analysed for IFN signatures using INTERFEROME, the database of IFN regulated genes. Significance was determined by the application of a Pearson chi-squared test.

Transcription Factor Binding Site Enrichment Analysis

Putative proximal promoter sequences 1500 bp 5' upstream and 200 bp downstream relative to the annotated transcription start site were extracted from Ensembl release 59 through the ENSEMBL BIOPERL API (Culhane et al. 2010, supra). The CLOVER algorithm (Frith et al., *Nucleic Acids Res* 32:1372-1381 (2004)) utilizing the Transfac Professional (ver. 2010.3) position weight matrices as described previously (Matys et al., *Nucleic Acids Res* 34:D108-110 (2006)) were employed to identify transcription factor enrichment within the gene set. Promoters from the complete INTERFEROME gene list and 22732 Ensembl protein-coding genes were employed as background sets with p-value thresholds of 0.01 and 1000 randomizations applied. Transcription factor binding site identification was performed using the MATCH algorithm of Transfac Professional (ver. 2010.3) with filters applied to minimize false positives. Transcription factor binding sites were visualized through the INTERFEROME promoter visualization scripts.

Promoter enrichment analysis using and binding site identification was performed on the 540 suppressed genes identified through INTERFEROME analysis. Transfac Pro 2010.3 matrices were applied in both the CLOVER and MATCH algorithms.

Cell Culture and Molecular Techniques

66cl4 and 4T1 cell lines were kindly provided by Dr. Fred Miller (Karmanos Cancer Institute, Detroit, Mich.). Derivation of the 4T1.2 line has previously been described (Eckhardt et al. 2005, supra; Lelekakis et al. 1999, supra). Recombinant Interferon-$\alpha_1$ was used at a dose of 1000 IU/mL. Interferon-$\alpha$ receptor blocking antibody (MAR1-5A3) was used at a concentration of 10 μg/mL (Leinco, St Louis, Mo.). G-CSF ELISA was performed according to manufacturer's instructions (R&D Systems, Minneapolis, Minn., USA). Flow cytometry was performed using standard techniques. MDSCs were assessed using Ly6G (clone IA8) and CD11b (clone M1/70) specific antibodies (BD Pharmingen, Franklin Lakes, N.J., USA) at a dilution of 1:200. Flow Cytometry was performed using an LSR-II (BD Pharmingen, San Jose, Calif.). Real-time RT-PCR was performed using standard techniques. In vitro proliferation was assessed using a sulforhodamine B binding assay as previously described (Eckhardt et al. 2005, supra). Immunohistochemistry was performed using standard techniques, using $\alpha$-mouse Irf7 (Zymed/Invitrogen, Carlsbad, Calif., USA) $\alpha$-human Irf7 (BD Pharmingen, Franklin Lakes, N.J., USA) at a concentration of 5 μg/mL.

CFSE T-Lymphocyte Suppression Assay

The mixture of MDSC and CFSE labelled splenocytes were plated in triplicates in a 96-well round-bottom plate. The suppressor and responder cells were cultured together at ratios of 1:1, 1:2, 1:4, 1:8 and 1:16 with the same number of responder cells in each well (100,000 cells/well). Cells were stimulated using anti-CD3 (clone 145-2c11, BD Biosciences, San Jose, Calif., USA) and anti-CD28 (clone 37.51, BD Biosciences, San Jose, Calif., USA) antibodies at 40 ng/ml. The total volume of medium in each well was adjusted to 175 Cells were incubated at 37° C. for 72 h, and the cell proliferation was measured by CFSE dilution using flow cytometry. CD4$^+$ and CD8$^+$ T-lymphocytes were assessed using specific antibodies (anti-mouse CD4-APC, clone GK1.5, eBioscience; anti-mouse CD8a PE-Cy7, clone 53-6.7, eBioscience)

Mouse Assays

Female Balb/c mice (6-8 weeks old) were obtained from ARC (Perth, WA, Australia) or Walter and Eliza Hall Institute (Kew, Vic, Australia) breeding facilities. Female NSG mice were obtained from WEHI breeding facility under license from The Jackson Laboratory and Balb/c Ifnar1$^{-/-}$ (Hwang et al. 1995, supra) were bred in-house. Recombinant IFN-$\alpha$1 was injected intraperitoneally 3 times weekly at a dose of $10^5$ IU/dose. All other mouse assays were performed using standard techniques. Metastasis was assessed using a previously described assay (Eckhardt et al. 2005, supra). Mouse investigations were performed with the approval of the Peter MacCallum Animal Ethics Experimentation Committee.

Statistics

Metastasis data has been $\log_{10}$ transformed for visualization. Unless otherwise stated, all statistics are Student's T-test performed on untransformed data. Dot plots and histograms are means and error bars are S.E.M. All statistics were performed using the data analysis package within Microsoft Excel or the analysis tool within GraphPad Prism 5. Kaplan-Meier survival analysis was performed using GraphPad Prism 5 and the Gehan-Breslow-Wilcoxon test was used to determine significance. Four publicly available breast cancer microarray datasets with known first site of distant relapse were used in the survival analyses: GSE2034, GSE12276, GSE2603, NKI295 as described in Harrell et al. (2012, supra). The Irf7 gene set was treated as a continuous variable and is defined as the averaged gene expression of the subgroup of 208 genes within the 540 IRGs that contained predicted Irf7 putative binding sites (including Irf7, FIG. 7).

Immunopurification

Immunopurification was performed according to the protocol developed by Parker and colleagues (Parker et al. 2008, supra; Parker et al., *Cancer Res* 64:7857-7866 (2004); St Croix et al., *Science* (New York, N.Y.) 289:1197-1202 (2000)), with the epithelial selection antibody replaced by $\alpha$-mouse-Ep-CAM antibody (BD Pharmingen, Franklin Lakes, N.J., USA). Briefly, mice were sacrificed and tissues collected. Tissues were disaggregated in DMEM containing 3 mg/mL Collagenase A (Roche Diagnostics GmbH, Mannheim, Germany) and digested for 90 min at 37° C. prior to filtration through a 100 μm and a 70 μm nylon filter and red blood cell lysis in an alkaline buffer (150 mM NH$_4$Cl, 1 mM KHCO$_3$, 0.1 mM EDTA). B lymphocytes and T lymphocytes were removed by incubation with pan-B and pan T DYNABEADS (Invitrogen, Carlsbad, Calif., USA) for 20 min at 4° C. Epithelial cells were then selected by incubation with sheep anti-rat DYNABEADS (Invitrogen, Carlsbad, Calif., USA) pre-conjugated to a rat anti-mouse EP-CAM antibody (BD Pharmingen, Franklin Lakes, N.J., USA) for 30 min at 4° C.

Enforced Gene Expression

We used the pMSCV retroviral expression vector (Clontech, Palo Alto, Calif., USA) to enforce the expression of Irf7. Empty plasmid or plasmid containing a flag tagged Irf7 construct was transfected into HEK-293 packaging cells using LIPOFECTAMINE (Invitrogen, Carlsbad, Calif., USA). Conditioned media was filtered and incubated with target 4T1.2 cells. 4T1.2 cells were then selected using puromycin, single cell cloned and multiple clones pooled.

Distant-Metastases Survival Analyses Using Gene Expression Datasets

Four publicly available breast cancer microarray datasets with known first site of distant relapse were used in the survival analyses: GSE2034, GSE12276, GSE2603, NKI295 as previously described in Harrell et al. (2012, supra). Normalised gene expression data was downloaded. The Irf7 gene signature was treated as a continuous variable and is defined as the averaged gene expression of the 208 genes within the 540 IRGs that contained predicted Irf7 putative binding sites and (including Irf7, FIG. 7). Probes were mapped to EntrezGeneIDs and when multiple probes existed, the probe with the highest variance was used. Gene expression values were scaled such that the quantiles 2.5% and 97.5% equalled −1 and +1 respectively. This scaling is robust to outliers and allows comparison between microarray datasets (Haibe-Kains et al., *J Natl Cancer Inst* 104: 311-325 (2012)). A Cox proportional regression model were used to estimate hazard ratios and 95% confidence intervals for distant relapse to bone in relation to the expression of the Irf7 signature as a continuous variable with adjustment for classic prognostic factors: tumour size (T1 vs T2), nodal status (positive vs negative), estrogen receptor status (positive vs negative) and histological grade (Grade 1 vs 2 vs 3) stratified according to dataset, using the change in the likelihood ratio $\chi2$ value. The Kaplan-Meier method was used to draw survival curves and the log-rank p test used to evaluate for differences in survival across the strata. In total, there were patient data for 855 patients with as first site of relapse bone (n=238), brain (n=49), lung (n=101) and liver (n=107). For analyses of bone relapse free survival, non-bone events (i.e. liver, lung and brain) were censored (and vice-versa for the non-bone survival analyses). Note that analyses separately for brain, lung and liver relapse-free survivals were also not significant (log-rank P=0.4, 0.8 and 0.56 respectively). Correlations were performed using a Spearman's Rho statistic ($R_s$). Analyses were performed using R version 2.9.2 (http://www.r-project.org/) and SPSS (SPSS Inc. Chicago, Ill.) version 20.0.

Real-Time RT-PCR (RNA Expression Analysis)

RNA was extracted using Trizol (Invitrogen, Carlsbad, Calif., USA) and reverse transcribed cDNA using standard techniques. Real-time PCR was performed using SYBR reagent (Applied Biosystems, Carlsbad, Calif., USA). The following primer sequences were used:

```
GAPDH
Fwd
                                   (SEQ ID NO: 1)
5'-TCCCACTCTTCCACCTTCGA-3'

Rev
                                   (SEQ ID NO: 2)
5'-GTCCACCACCCTGTTGCTGTA-3',

Irf7
Fwd
                                   (SEQ ID NO: 3)
5'-CCACACCCCCATCTTCGA-3'

Rev
                                   (SEQ ID NO: 4)
5'-CCTCCGAGCCCGAAACTC-3',

Irf9
Fwd
                                   (SEQ ID NO: 5)
5'-GCTCTAGCCATAGCCAAGAGAATC-3'

Rev
                                   (SEQ ID NO: 6)
5'-TCCAGTAAATGTCGGGCAAAG-3',

STAT1
Fwd
                                   (SEQ ID NO: 7)
5'-CGCGCATGCAACTGGCATATAACT-3'

Rev
                                   (SEQ ID NO: 8)
5'-AAGCTCGAACCACTGTGACATCCT-3',

G-CSF
Fwd
                                   (SEQ ID NO: 9)
5'-AGGTACGAAATGGCCAGGACA-3'

Rev
                                   (SEQ ID NO: 10)
5'-TGGCAGCAGATGGAAAACCTAG-3'.
```

Expression level of each gene was calculated based on the cycle threshold (CT), set within the linear range of DNA amplification. Expression level (arbitrary units) was calculated as relative transcript abundance (RTA) by: RTA=10000/($2^{\Delta CT}$), where $\Delta CT$=CT (gene of interest)–CT (GAPDH).

Mouse Metastasis, Survival Assays and In Vivo Depletion of Antibodies

These techniques have previously been described by Eckhardt and colleagues (Eckhardt 2005). Briefly, mice were inoculated with $10^5$ cells into the $4^{th}$ mammary fatpad of female 6-8 week old Balb/c mice. Tumour volumes were monitored by caliper measurement 3 times weekly. All animals were sacrificed by isoflurane overdose when any animal showed signs of distress (usually ds 28-35). Metastatic burden in secondary tissues was detected by a Q-PCR based assay using a reporter sequence inserted into the genome of the 4T1.2 cells. Survival assays were conducted in the same way except at day 22 the mice were anaesthetized using either a combination of ketamine hydrochloride (1.2 m/g of mouse)/xylaxil hydrochloride (3 µg/g of mouse) or 2.5% aerosol isoflurane in 100% oxygen and the primary tumour was surgically removed and weighed. Mice were harvested individually, not as a group, when they showed signs of distress. At time of sacrifice, all mice had evidence of bone and lung metastasis unless otherwise stated. Anti-CD8 (clone 53-6.7, produced in house) and the control antibody rat IgG2a (clone 2A3, produced in house) were injected intraperitoneally at 50 µg per dose on days –1, 0, 1, 4, 7 and subsequently every 7 d. Rabbit anti-asialo GM1 was purchased from Wako chemicals and injected intraperitoneally according to the manufacturer's instructions.

Histology and Immunohistochemistry

With one exception, all tissues were fixed in 10% neutral buffered formalin for 24 h. Bones were decalcified in 20% EDTA for 14 d at room temperature. All tissues were paraffin embedded and sectioned by the Peter MacCallum Cancer Centre histology facility or Peter MacCallum Cancer Centre Pathology Division. H&E staining was also performed by the same histology facility. The exception was a separate series of tissue microarrays constructed by P.A. at The Johns Hopkins Hospital from paired primary breast carcinomas and hematogenous metastases from the same patients, most of which were harvested at rapid autopsy as previously described (Wu et al. 2008; Cimino et al., *Breast Cancer Res Treat* 123:701-708 (2010)). Standard immunohistochemistry techniques were used to prepare the sections for staining. Heat antigen retrieval was performed in citrate buffer (10 mM tri-sodium citrate, pH 6.0) at 125° C. for 3 min under pressure. α-mouse Irf7 antibody was obtained from Invitrogen (clone zm7), α-human/mouse Irf9 antibody from abcam (cat #ab51634) and α-human Irf7 antibody from BD Pharmingen (cat #AHP1179).

Interferon-α ELISA

IFN-α ELISA was performed using standard molecular biology techniques. Antibody clone RMMA-1 was used as the capture antibody (PBL Interferon Source, Piscataway, N.J., USA) and a rabbit polyclonal anti-mouse IFN-α was used as the detection antibody (PBL Interferon Source, Piscataway, N.J., USA). Cells were seeded at a density of 50,000/mL and allowed to adhere for 4 h before being treated with vehicle control or 10 µg/mL of poly(I:C) for 24 h.

Ly6G$^+$ Cell Preparation (MDSC Preparation)

Mouse blood was harvest by cardiac puncture and the spleens were removed and single cell suspension was prepared. Red blood cells were lysed by resuspending the cells in 1 ml of red blood cell lysis buffer containing 150 mM $NH_4Cl$, 1 mM $KHCO_3$ and 0.1 mM EDTA at room temperature for five min. Cells were then washed twice and resuspended at $5 \times 10^7$-cells/ml in FACS buffer containing 0.1% sodium azide, 2% FCS and 2 mM EDTA. Ly6G$^+$ MDSC cells were selected based on their expression of Ly6G and CD11b (Ly6G$^+$CD11b$^+$). Cell sorting was performed using the FACSDiVa cell sorter (BD Biosciences, San Jose, Calif., USA) and FACSAria II cell sorter (BD Biosciences, San Jose, Calif., USA). Unlabelled samples and single labelled controls for each fluorochrome were included for setting voltage and compensation parameters.

CFSE Labelling

Splenocyte single cell suspension was prepared. Cells were resuspended in 20 mL PBS containing 2 mM EDTA and subsequently labelled with 1 µM CFSE (Invitrogen, Carlsbad, Calif., USA). After a seven-min incubation at room temperature, the tube was filled up with α-MEM containing 5% FCS and spun at 800 g for five min. After being washed twice, the cells were then resuspended in α-MEM containing 5% FCS. The labelling of cells by CFSE was analyzed by flow cytometry.

MS-HRM
DNA Samples

Sections were cut from eight blocks containing formalin-fixed paraffin-embedded (FFPE) normal mammary tissue, primary tumours and matched bone metastases. One 3 µm section from each block was stained with H&E to identify the tumour enriched area. The content of tumour cells in all cases was assessed by a pathologist. Tissue areas consisting of at least 80% tumour cell content were selected for needle macrodissection. Seven µm tissue sections of each sample were stained with methyl green and subsequently subjected to needle macrodissection.

DNA was extracted using the QIAamp DNA Blood Mini Kit (Qiagen, Hilden, Germany) according to Wu et. al. (Wu et al., *Appl Immunohistochem Mol Morphol* 10:269-274 (2002)) with slight modifications. Briefly, needle macrodissected tissue from each sample was transferred immediately to a 1.5 mL screw tube containing 100 µL Tissue Lysis Buffer ATL (Qiagen) and incubated at 98° C. for 15 min. Subsequently the tube was cooled to room temperature, 12 µl proteinase K (20 mg/mL) (Worthington Biochemical Corporation, Lakewood, N.J.) was added and incubated at 56° C. for 72 h. Every 24 h an additional 12 µL proteinase K (20 mg/mL) was added. Following incubation, 110 µL Lysis Buffer AL was added and incubated at 72° C. for 10 min. The reaction mixture was cooled to room temperature, 110 µL ethanol was added and the mixture transferred into a QIAamp Mini Spin Column (Qiagen) for DNA elution as per manufacturer's instructions.

DNA was quantified and its purity assessed using the NanoDrop spectrophotometer 2000 (NanoDrop Technologies, Thermo Fisher Scientific, Wilmington, Del.). The purity of all DNA samples extracted had an absorbance $A_{260}/A_{280}$ ratio of between 1.8 and 1.9.

SssI Treatment

Fully methylated control DNA was prepared from 500 ng of extracted lung DNA of a normal BALB/c mouse by utilising the CpG Methyltransferase M.SssI (New England BioLabs, Ipswich, Mass.). M.SssI treatment was performed as described elsewhere (Mikeska et al., *Methods Mol. Biol.* 791:33-53 (2011)). The preparation was stored at −35° C.

Bisulfite Treatment

Five hundred ng of DNA were bisulfite modified using the EpiTect Bisulfite Kit (Qiagen) according to the manufacturer's instructions. The SssI treated DNA (fully methylated control DNA) and the corresponding genomic DNA (unmethylated control DNA) was eluted twice in a final volume of 50 µL Elution Buffer EB, whereas FFPE-derived DNA was eluted twice in a final volume of 404 Elution Buffer EB. The eluate was stored at 4° C.

Methylation-Sensitive High Resolution Melting (MS-HRM)

A DNA methylation standard series was prepared by diluting fully methylated control DNA in unmethylated control DNA. The DNA methylation standards comprised 100% 50%, 25%, 10% and 0% of fully methylated control DNA. MS-HRM (Wojdacz and Dobrovic, *Nucleic Acids Res* 35:e41 (2007)) was performed on a Rotor-Gene 6000 (Corbett, Sydney, Australia). Each DNA methylation standard and each sample was run in duplicate, while the bisulfite untreated genomic DNA control and the no template control were performed only once.

The primer sequences for the analysis of the CpG rich region spanning exon 1 of Irf7 were: 5'-GAGTGGTT-TAAGAGTTTTATATATTTGGTAT-3' (SEQ ID NO:11) and 5'-ACCACACCCTACCTAAACTCTA-3' (SEQ ID NO:12) (Region 1). The amplified region corresponds to GenBank accession number AC163434, nucleotides 62597-62727. The primer sequences for the analysis of the CpG island associated with the boundary of intron 1/exon 2 of Irf7 were: 5'-AGATAGCGGGAAGTTAGTAGTTAT-3' (SEQ ID NO:13) and 5'-CTAAATAAACTATCACAAA-CTAAAC-CCTA-3' (SEQ ID NO:14) for region 2 and 5'-GGTT-TAGTTTGTGATAGTTTATTTAGGT-3' (SEQ ID NO:15) and 5'-CTCAATATAAATTCCTCTACCAAAATAACTA-3' (SEQ ID NO:16) for region 3. The amplified regions correspond to GenBank accession number AC163434, nucleotides 62250-62388 (Region 2) and nucleotides 62152-62275 (Region 3). PCR was performed in 0.1 mL tubes with a final reaction volume of 20 µL containing 200 nmol/L of each primer, 200 µmol/L of each dNTP, 5 µmol/L SYTO 9 (Invitrogen, Life Technologies, Carlsbad, Calif.), 2.5 mmol/L MgCl$_2$ (2.0 mmol/L for region 3), 0.5 U HotStarTaq DNA Polymerase in its supplied buffer (1×) (Qiagen) and 1 µL (1.5 µl, for region 3) of bisulfite modified DNA. PCR amplification conditions were: 1 cycle of 95° C. for 15 min, 50 cycles of 95° C. for 25 s (20 s for region 3), 60° C. (57° C. for region 2 and 57.5° C. for region 3) for 20 s (15 s for region 3) and 72° C. (70° C. for region 3) for 25 s (20 s for region 3). This was immediately followed by a hold at 97° C. for 1 min, 60° C. for 1.5 min and a HRM step from 60 to 95° C. rising at 0.2° C. per second, and holding for 1 sec after each stepwise increment.

The primer sequences for the analysis of the CpG island associated with the promoter region of Stat1 were: 5'-GGT-GNGTTGATGGAATAGT-3' (SEQ ID NO:17) and 5'-CNAAAATCTCC-AAAAAACTTTAACAA-3' (SEQ. ID NO:18) (N corresponds to a mixture of the bases A, C, G and T). The amplified region corresponds to GenBank accession number AC123752, nucleotides 146569-146709. PCR was performed in 0.1 mL tubes with a final reaction volume of 20 µL containing 200 nmol/L of each primer, 200 µmol/L of each dNTP, 5 µmol/L SYTO 9 (Invitrogen, Life Technologies), 1.75 mmol/L MgCl$_2$, 0.5 U HotStarTaq DNA Polymerase in its supplied buffer (1×) (Qiagen) and 1 µL of bisulfate modified DNA. PCR amplification conditions were: 1 cycle of 95° C. for 15 min, 50 cycles of 95° C. for 25 s, 56° C. for 20 s and 72° C. for 25 s. This was immediately followed by a hold at 97° C. for 1 min, 60° C. for 1.5 min and a HRM step from 60 to 95° C. rising at 0.2° C. per second, and holding for 1 sec after each stepwise increment.

Results
Profiling of Matched Mammary Tumours and Spine Metastases

Tumour epithelial cells were isolated from 4T1.2 primary tumours growing in the mammary gland and matched spine metastases (Eckhardt et al. 2005), as described previously (Parker et al., *J Pathol* 214:337-346 (2008)). Differences in gene expression profiles of tumour cells isolated from four matched pairs of primary tumours and bone metastases (FIG. 1) were interrogated by gene ontology analysis and found to be highly enriched for immune and defense response ontologies (confidence level P<0.003) (Table 3a).

3,547 probes sets representing 3,061 genes were significantly down-regulated ≥2-fold in spine (P<0.05), while 1,530 probes sets representing 1,012 genes were up-regulated (FIG. 1). Genes were unambiguously identified through Ensemble annotation (Culhane et al., *Nucleic Acids*

Figure 7:
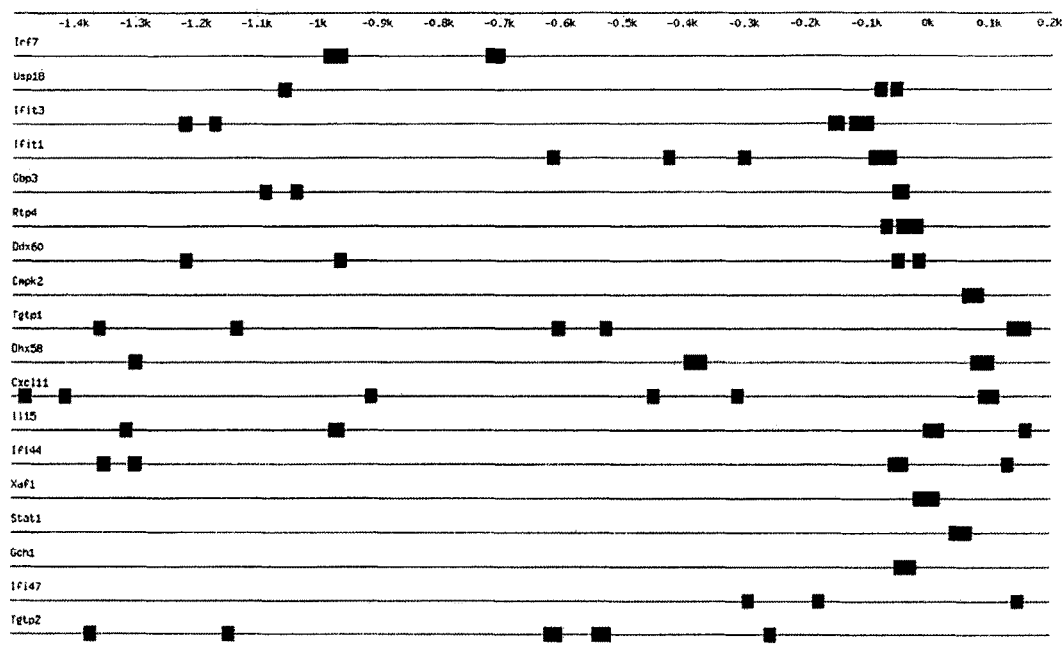
FIG. 7: Visualization of the TRANSFAC Match predicted IRF/IRF7, ISRE and IRF2 sites in the putative promoter regions (−1,500 bp-200 bp) of a subset of interferon regulated metastases suppressed genes.
Figure 8:
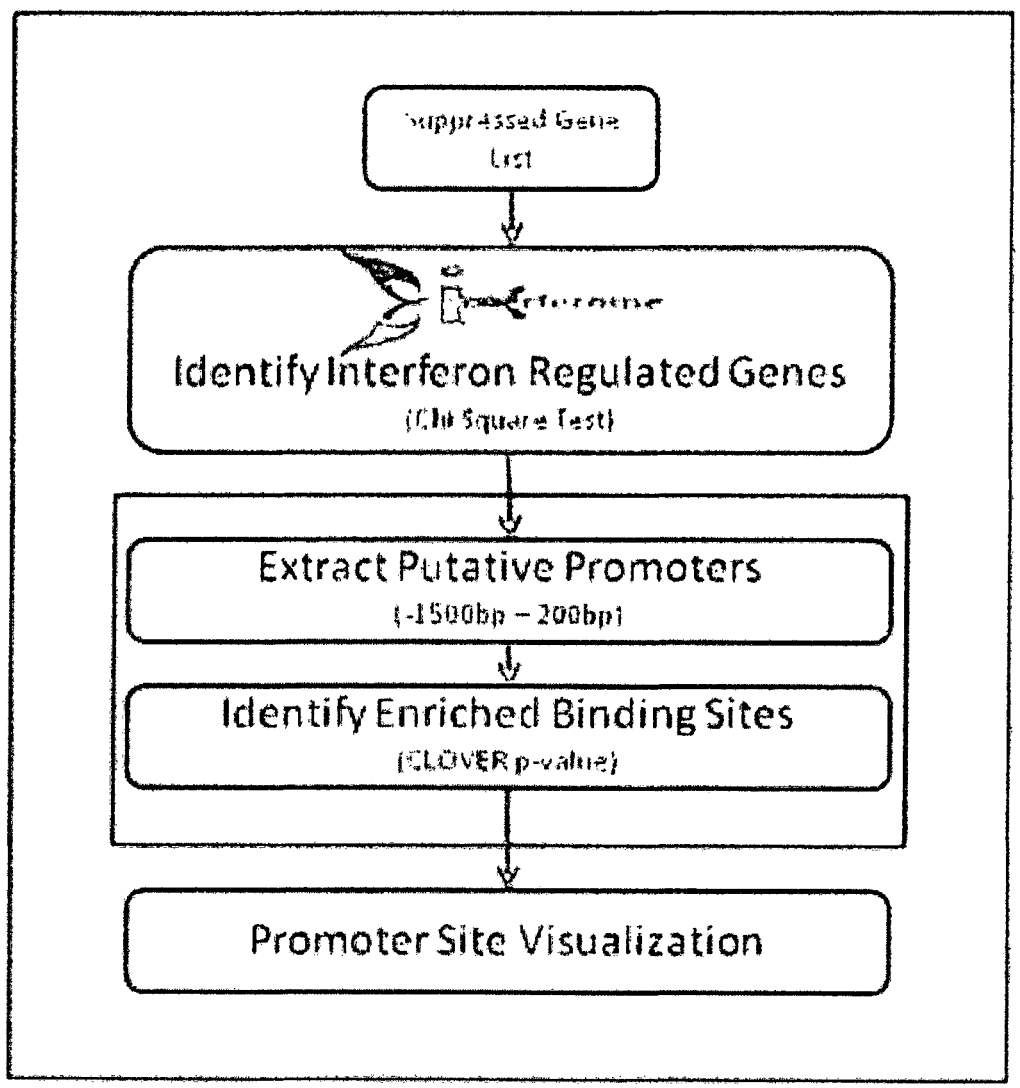
FIG. 8: Promoter analysis framework applied in the identification and visualization of Interferon signature enrichment and IRF promoter binding sites from the suppressed gene list. Type I IFN signature was identified using the Interferome database. Promoter analysis was performed on sequence extracted from Ensembl v59 and analysed using the CLOVER algorithm and the TRANSFAC database. Visualization was achieved using the Interferome interface.

*Research* 38:D716-D725 (2010)). Analysis of the 3061 suppressed genes using the INTERFEROME database identified a high number (540) of IRGs (FIG. 1, Table 4)—a significant over-representation (P<0.001). In contrast, there was no significant enrichment of IRGs in the up-regulated gene list. Promoter enrichment analysis of the INTERFEROME gene set (540 genes) identified significant IRF and ISGF-3 enrichment (P<0.001) and IRF/Irf7 enrichment (P<0.001) and further analysis identified that 208 of the 540 IRGs including Irf7, contained predicted Irf7 binding sites (FIG. 7, 8).

Figure 2:
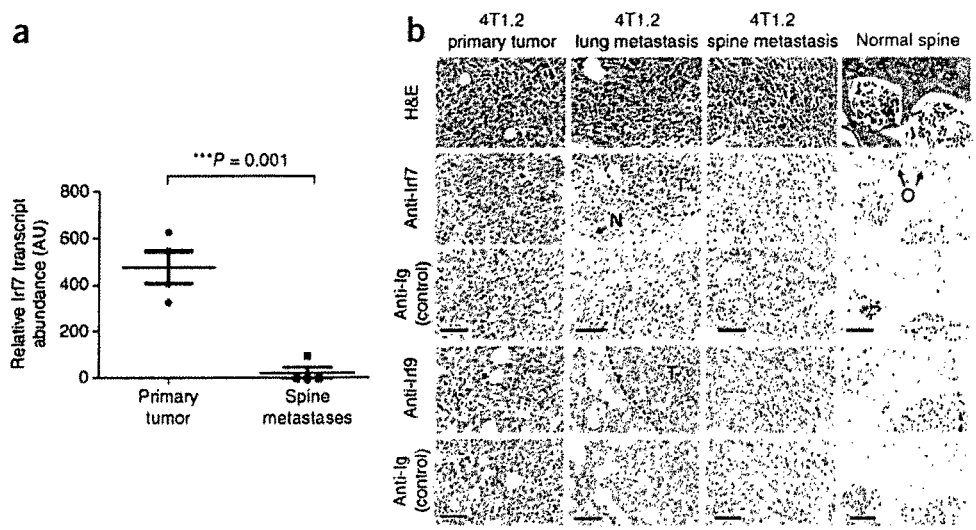
FIG. 2: Expression of the transcription factor IRF7 is suppressed in bone metastases. (a) Real-time RT-PCR analysis for IRF7 expression in mRNA isolated from 4T1.2 primary tumours and spine metastases (error bars represent SEM, n=4). IRF7 transcript abundance is relative to GAPDH. (b) Immunohistochemical staining of tissue sections taken from 4T1.2 tumour bearing Balb/c mice (primary tumours, lung metastases and spine metastases) and control mice (normal spine). Serial sections were stained with haematoxylin and eosin (H&E) for morphology (top), IRF7 specific antibodies ($\alpha$-IRF7), pre-immune rabbit Ig control, IRF9 specific antibodies ($\alpha$-IRF9) or rat IgG control. T=tumour, N=normal lung epithelium, 0=osteocytes. Scale bar=50 µm. Dashed line represents tumour boundaries.

Irf7 is a major regulator of the type I IFN pathway (Honda et al., *Nature* 434:772-777 (2005)) and was itself significantly suppressed in tumour cells from bone metastases (Table 5). The expression of Irf7 in primary tumour epithelium and its loss in matched bone metastases was validated by real-time RT-PCR of epithelial mRNA (FIG. 2a, P<0.001) and by immunohistochemistry (FIG. 2b). The dramatic suppression of both the Irf7 transcription factor and 208 putative target genes provided compelling argument for the functional importance of this innate signalling pathway.

Figure 9:
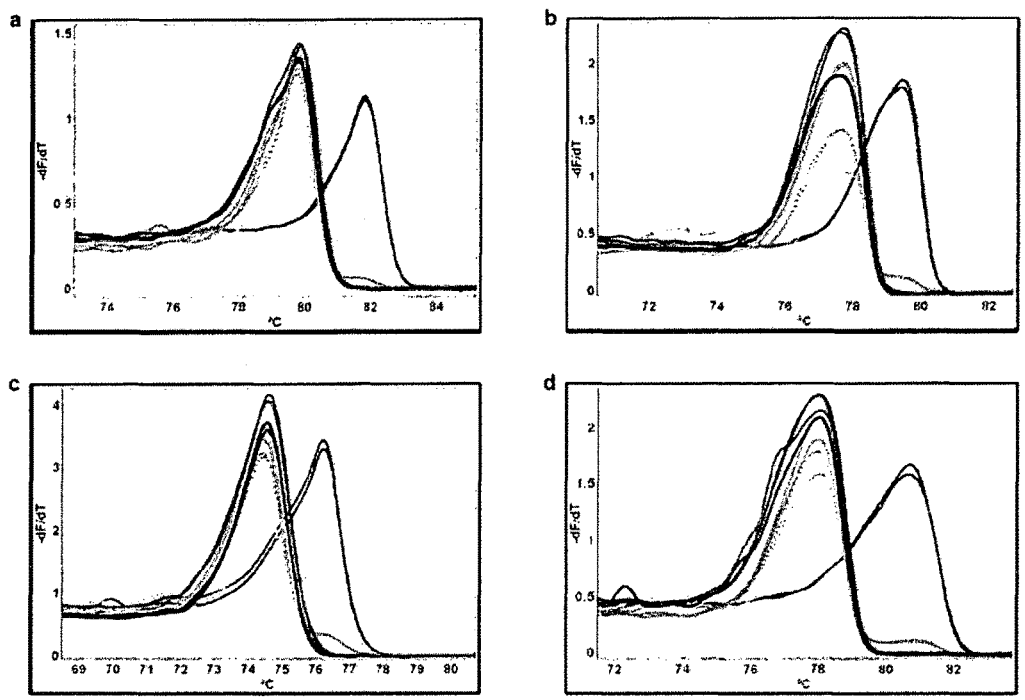
FIG. 9: Tm plots (negative first derivative of the high resolution melting curves) obtained from MS-HRM experiments for the DNA methylation analysis of IRF7 and STAT1. The Tm curves were partly smoothened by applying a light digital filter available in the analysis software. The curves for the unmethylated and fully methylated control DNAs are shown in green and red respectively. Additionally, the DNA methylation standards of 50% (turquoise dotted curves) and 10% (grey dotted curves) are shown. The black curves correspond to the normal tissue sample 841/07 and the blue curves correspond to the spine metastasis 2,375.07. The normal tissue and all tumour samples were unmethylated for all regions analysed. For clarity, only sample 2375/07 is shown as a representative tumour sample. a) Tm plot for the CpG rich region spanning exon 1 of IRF7 (Region 1). b) Tm plot for the CpG island associated with the boundary of intron 1/exon 2 of IRF7 (Region 2). c) Tm plot for the CpG island associated with the boundary of intron 1/exon 2 of IRF7 (Region 3). d) Tm plot for the promoter region of STAT1.

The mechanism of loss of Irf7 expression could be due to direct epigenetic modification (methylation) or a decrease in the expression of components of the ISGF3 complex (containing STAT1, STAT2 and Irf9) that directly regulates Irf7 expression (Lu et al., *J Biol Chem* 275:31805-31812 (2000)). These results indicate the latter. Analysis of tumour cells macrodissected from primary tumours and matched spine metastases revealed no methylation at the CpG rich region spanning exon 1 or the boundary of intron 1 and exon 2 of Irf7 (FIG. 9a-c). However, expression of ISGF3 components, STAT1, Irf9 and STAT2 was reduced in bone metastases, correlating with Irf7 down-regulation (Table 5). The loss of STAT I expression was not due to methylation (FIG. 9d). Thus the mechanism of suppression of Irf7 expression is likely to be down-regulation of its upstream regulators, the ISGF3 transcriptional regulator complex. Consistent with this hypothesis, we detected nuclear localization of Irf9 in primary 4T1.2 tumours (FIG. 2b) indicative of ISGF3 translocation to the nucleus. By contrast, nuclear staining was barely detectable in bone metastases, mirroring that of Irf7 expression (FIG. 2b).

Irf7 Restores Type I IFN Signalling and Suppresses Metastasis

Figure 10:
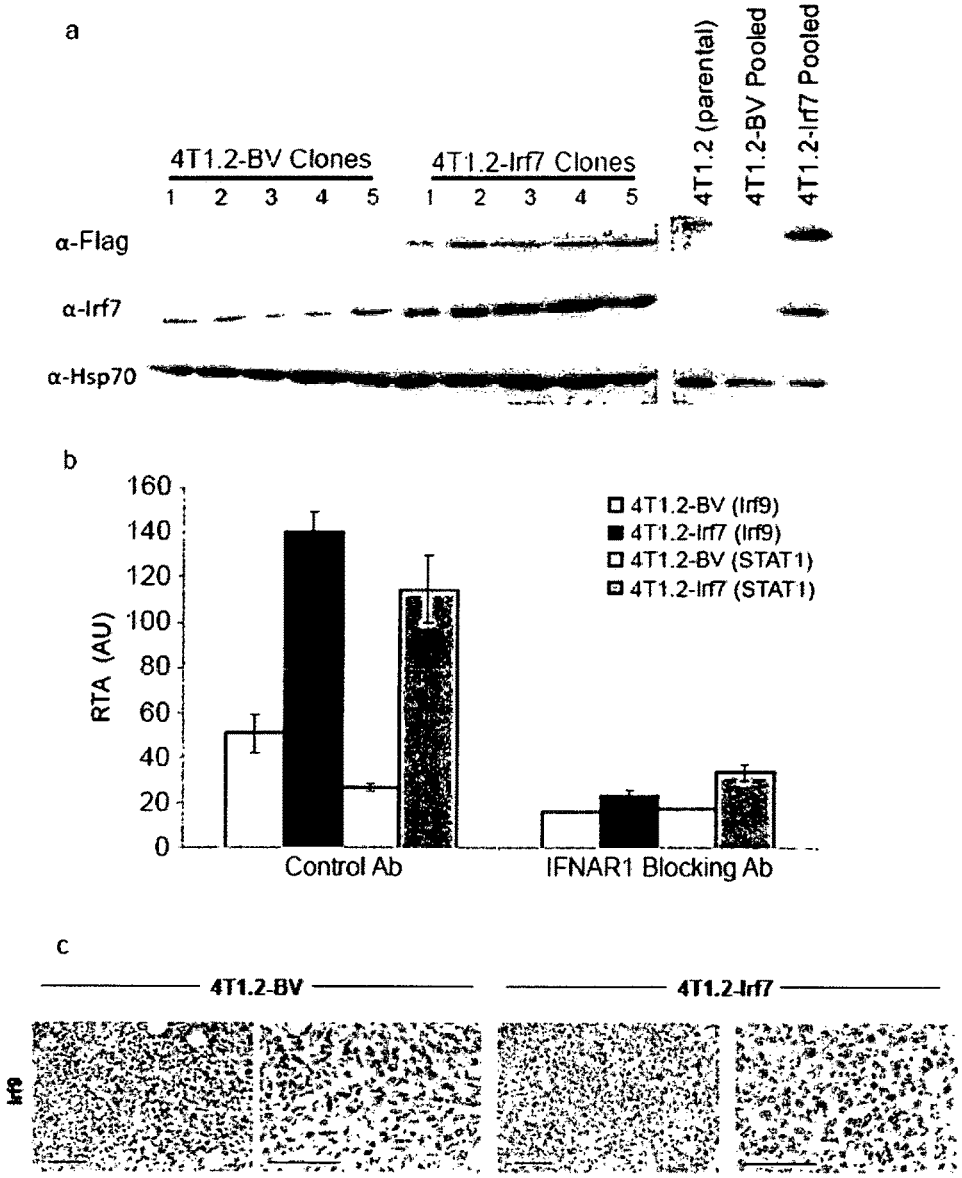
FIG. 10: Enforced expression of IRF7 restores expression of Type I IFN pathway. a. IRF7 expression in parental cells (4T1.2) or cells expressing a base vector construct (BV) or an IRF7 expression construct (IRF7). 5 individual clones were pooled in each group. b. Expression of IRF9 and STAT1 in BV cells or cells expressing IRF7, in the presence of an isotype control antibody or an IFNAR1 blocking antibody. c. Sections of primary tumours from mice bearing 4T1.2-BV or 4T1.2-IRF7 tumours stained for IRF9. Scale bar=50 µm.
Figure 11:
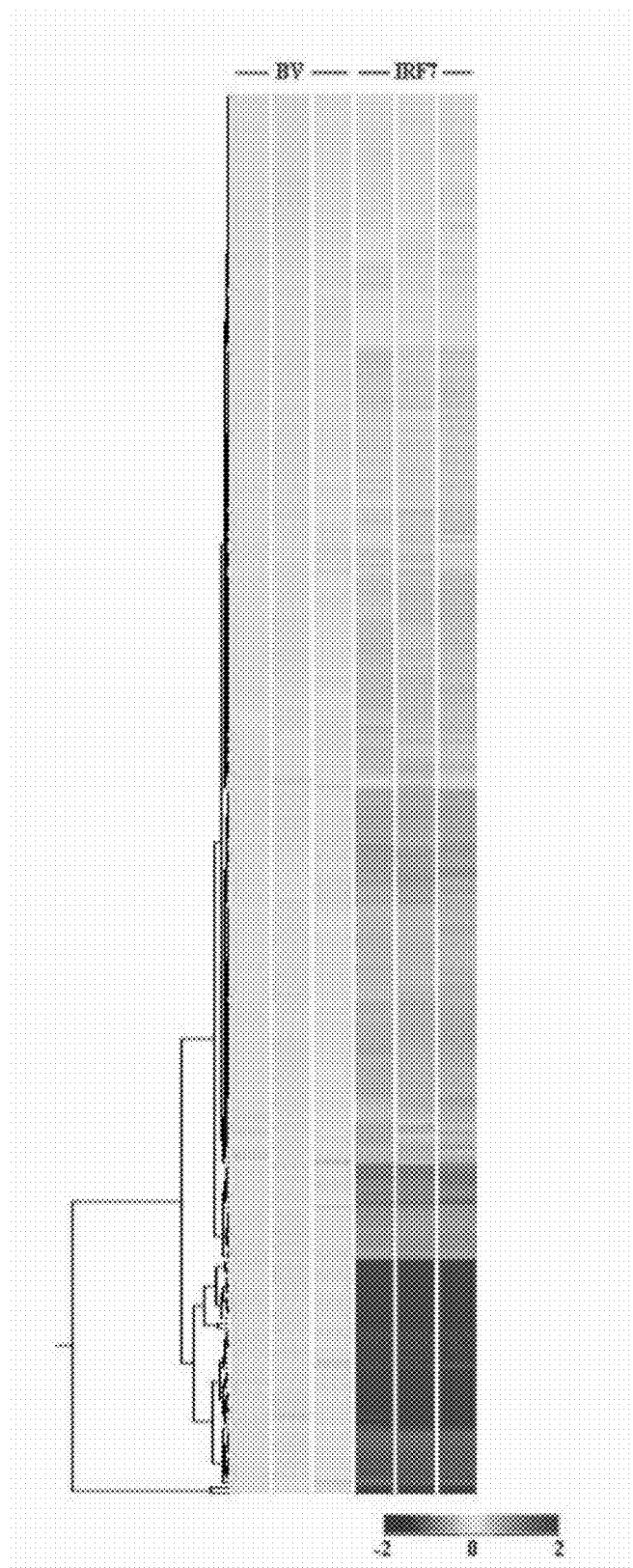
FIG. 11: Enforced IRF7 expression in 4T1.2 cells restores the IRF7-signature. Heat map representation of expression values for differentially expressed genes between 4T1.2BV and 4T1.2-IRF7 cells (fold change >2, P<0.05) hierarchically clustered on gene expression value. Red coloration represents induction while blue indicates reduction of expression relative to base vector control.

To determine the functional contribution of Irf7 in bone metastases, 4T1.2 clones were generated overexpressing Irf7 (4T1.2-Irf7, FIG. 10a), which did not display altered proliferation in vitro (FIG. 3a), even in the presence of pathway stimulation with IFN-α or a TLR3 agonist (Poly I:C) (data not shown). The expected increased expression of IFN-α, by ELISA (FIG. 3b), and two IRGs, Irf9 and STAT1, by qRT-PCR (FIG. 10b) was confirmed. The latter was due to secondary signalling by type I IFN, because an Ifnar1 neutralizing antibody (Sheehan et al., *J Interferon Cytokine Res* 26:804-819 (2006)) reduced Irf9 and STAT1 expression in 4T1.2-Irf7 cells to levels seen in control cells (4T1.2-BV) (FIG. 10b). In fact, microarray analysis of gene expression comparing 4T1.2-Irf7 to 4T1.2-BV cells revealed that all 208 genes that contained predicted Irf7 binding sites in their promoters were upregulated by Irf7 expression (FIG. 11). Furthermore, there was an increase in nuclear Irf9 expression in mammary tumours compared to 4T1.2-BV tumours (FIG. 10c). Thus, the production of IFN by enforced Irf7 expression stimulates the IFN/Ifnar signal transduction pathway.

Figure 3:
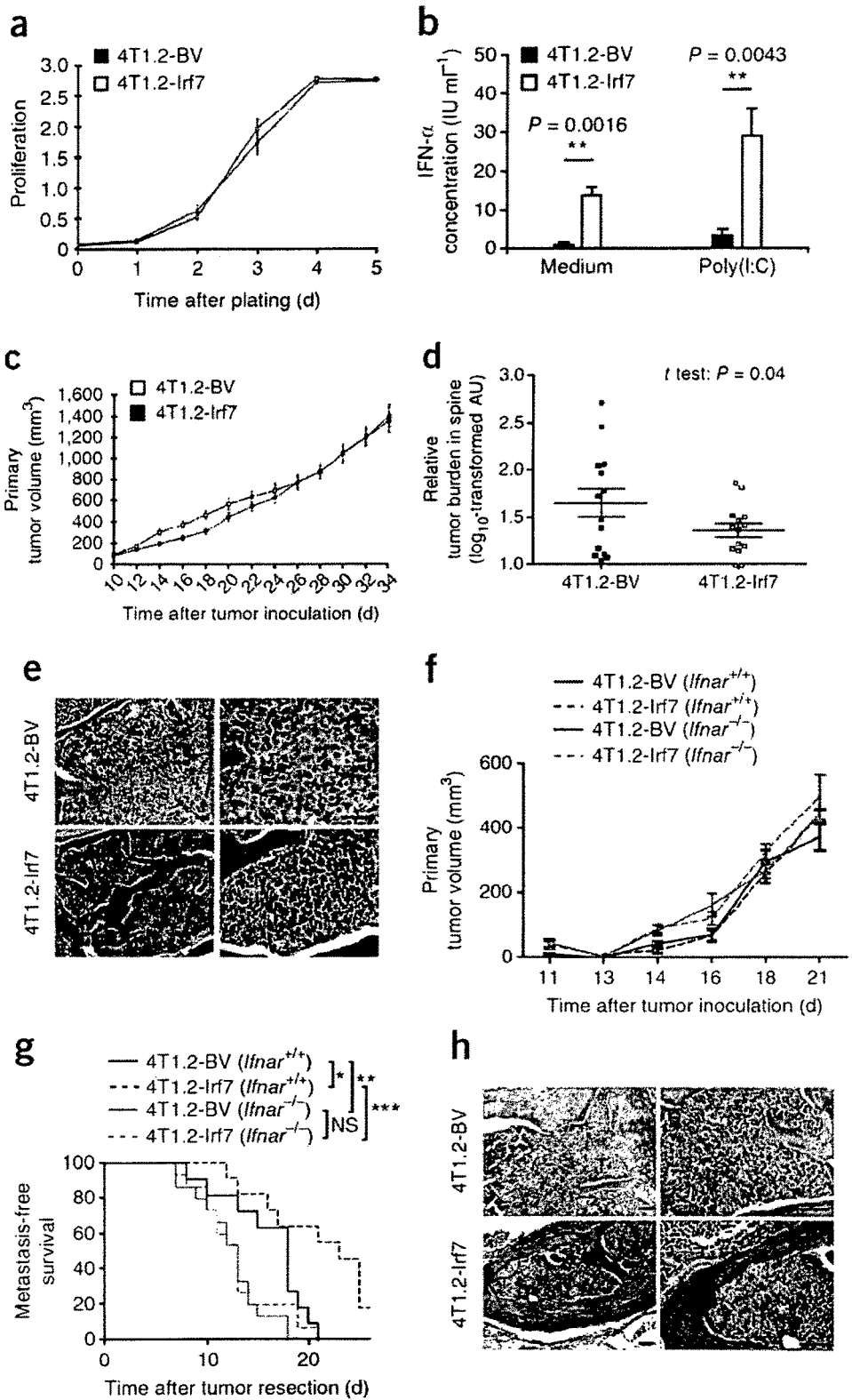
FIG. 3: Restoration of IRF7 expression enhances IFN signalling and inhibits metastasis. (a) In vitro proliferation assay of 4T1.2-BV and 4T1.2-IRF7 cells. n=6, error bars are S.E.M. (b) ELISA for IFN-$\alpha$ of conditioned medium from 4T1.2-BV or 4T1.2-IRF7 cells, with and without poly(I:C) stimulation. n=6 (c) Tumour volumes subsequent to inoculation of 4T1.2-BV or 4T1.2-IRF7 cells into the mammary gland of syngeneic, immunocompetent Balb/c mice. (d) Q-PCR detection of metastatic tumour burden in spines of 4T1.2-BV and 4T1.2-IRF7 tumour burdened mice (endpoint, d 32) (e) H&E stained sections of spines from immunocompetent Balb/c mice bearing 4T1.2-BV or 4T1.2-IRF7 tumours (Scale bar=50 µm, T=Tumour, Dashed line represents tumour boundaries). (1) Tumour volumes subsequent to inoculation of 4T1.2-BV and 4T1.2-IRF7 tumour cells into litter-matched Ifnar1$^{-/-}$ and wild-type mice. (g) When the primary tumours from mice bearing 4T1.2-BV or 4T1.2-IRF7 tumours reached 500 mm$^3$, they were resected and the disease-free survival rates were analysed. Log-rank test was performed. 4T1.2-BV Ifnar1$^{+/+}$ vs 4T1.2-IRF7 Ifnar1$^{+/+}$ (*P=0.0123); 4T1.2-BV Ifnar1$^{-/-}$ vs 4T1.2-IRF7 Ifnar1$^{-/-}$ (ns P=0.4317); 4T1.2 IRF7 Ifnar1$^{+/+}$ vs 4T1.2 IRF7 Ifnar1$^{-/-}$ (*P=0.0002); 4T1.2 BV Ifnar1$^{+/+}$ vs 4T1.2 BV Ifnar1$^{-/-}$ (P=0.0067). 4T1.2-BV Ifnar1$^{+/+}$ (n=12); 4T1.2-IRF7 Ifnar1$^{+/+}$ (n=13); 4T1.2-BV Ifnar1$^{-/-}$ (n=16); 4T1.2-IRF7 Ifnar1$^{-/-}$ (n=16) (h) H&E stained sections of spines from Ifnar1$^{-/-}$ mice bearing 4T1.2-BV or 4T1.2-IRF7 tumours at end-point (Scale bar=50 µm, T=Tumour, Dashed line represents tumour boundaries).

Restoration of the type I IFN pathway by enforced expression of Irf7 was demonstrated to reduce metastatic burden but not affect the primary tumour growth rates (FIG. 3c). Importantly, Irf7 overexpression resulted in a significant reduction in metastasis to spine (FIG. 3d) measured by PCR and by histology. Spine macrometastases were detected in 60% of mice bearing 4T1.2-BV tumours, yet were undetectable in mice bearing 4T1.2-Irf7 tumours (FIG. 3e).

To confirm that the Irf7-mediated reduction in metastasis can prolong survival and is dependent on type I IFN signalling to host cells, 4T1.2-BV or 4T1.2-Irf7 cells were inoculated into Balb/c wildtype or Ifnar1$^{-/-}$ (Hwang et al., *Proc Natl Acad Sci USA* 92:11284-11288 (1995)) mice. Although there was no difference in primary tumour growth between all groups (FIG. 3c), enforced expression of Irf7 led to a significantly prolonged metastasis-free survival in wild-type mice (FIG. 3g). In contrast, Ifnar1$^{-/-}$ mice, succumbed to metastasis faster and enforced Irf7 expression did not suppress metastasis (FIG. 3g), which were evident in all Ifnar1$^{-/-}$ animals (FIG. 3h).

Taken together, these results demonstrate that tumour cell IFN signalling driven by Irf7 reduces metastasis to bone, and the host response through Ifnar1 is critical for metastasis suppression and associated prolonged survival.

Irf7 Expression Restores Anti-Metastatic Immune Responses

Figure 4:
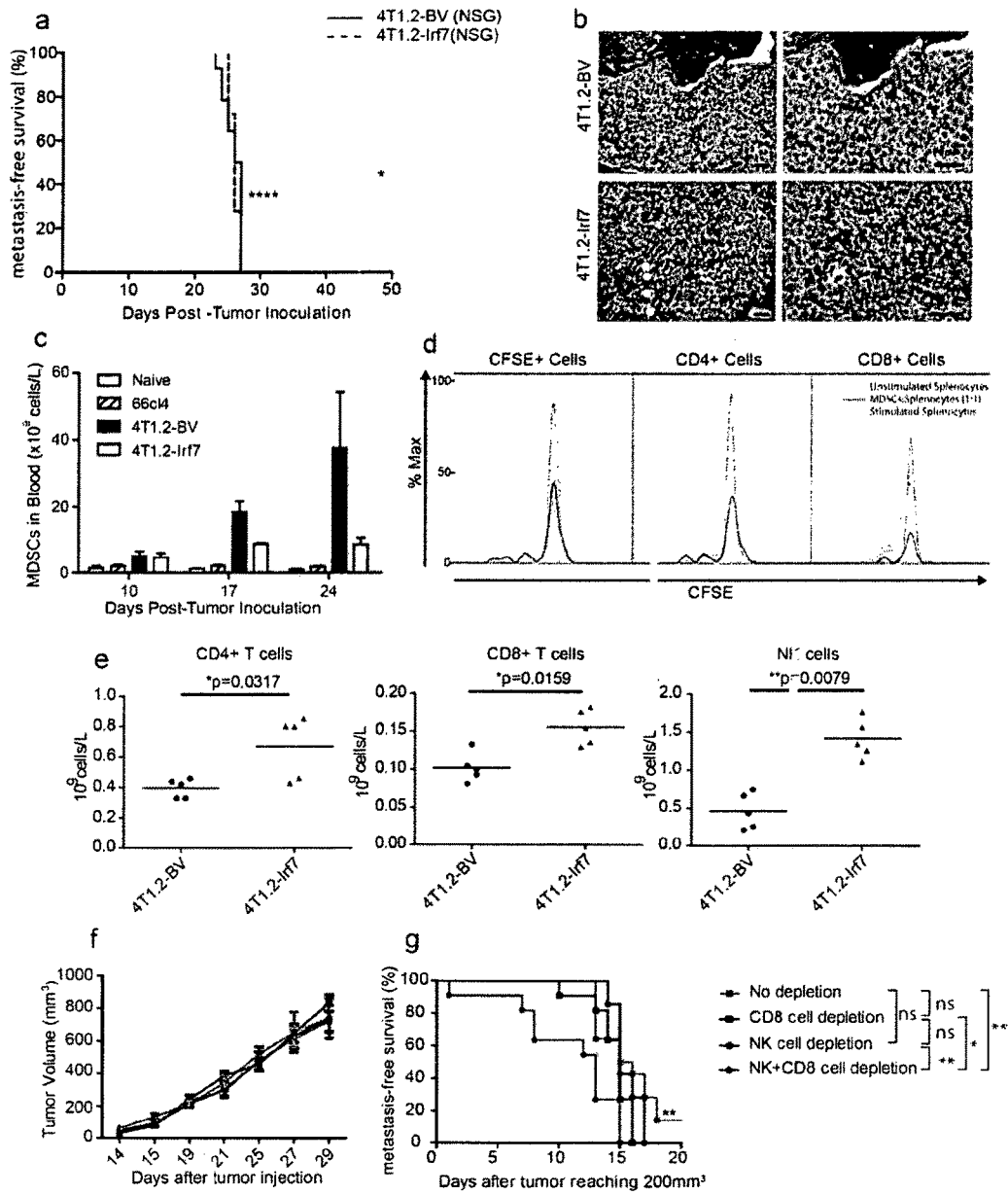
FIG. 4: Modulation of the immune system by metastatic tumour cells and reversion of these effects by enforced expression of the type I IFN pathway. (a) Disease-free survival of mice bearing 4T1.2-BV or 4T1.2-IRF7 tumours on either immunocompetent Balb/c background (*P=0.03, n=15, reproduced from FIG. 3g for comparison) or immunocompromised NSG background (** P=ns, n=15). (b) H&E stained sections of spines from NSG mice bearing 4T1.2-BV or 4T1.2-IRF7 tumours at the endpoint (Scale bar=50 µm, zoomed in on the right panel). (c) Accumulation of MDSCs over time in the peripheral blood of Balb/c mice bearing no tumour (naïve) or 66cl4, 4T1.2-BV or 4T1.2-IRF7 tumours (n=3). (d) CFSE labelled naïve Balb/c splenocytes were activated with anti-CD3/CD28 antibodies and co-cultured with or without CD11b$^+$Ly6G$^+$ MDSCs (ratio 1:1) derived from the 4T1.2-BV tumour-bearing mice. Total splenocytes, CD4$^+$ and CD8$^+$ T cell proliferation at 72 h was measured by flow cytometry. A two-tailed student t-test was performed and the mean fluorescence intensity (MFI) for CFSE was compared between the splenocytes±MDSC of 7 replicate samples. Total splenocytes * p=0.0006; CD8$^+$ T cells P=0.0021 and CD4$^+$ T cells P=0.0021. (e) The numbers of CD4$^+$ T cells (CD4$^+$ TCR$\beta^+$), CD8$^+$ T cells (CD8$^+$TCR$\beta^+$) and NK cells (DX5$^+$TCR$\beta^-$) in the peripheral blood of mice inoculated with 4T1.2-BV or 4T1.2-IRF7 tumours 5 d earlier. (f) Tumour volumes of 4T1.2-IRF7 tumour-bearing mice depleted of CD8 cells (anti-CD8 antibody, clone 53-6.7), NK cells (anti-asialo GM1), or both populations. (g) Disease-free survival rates of mice depleted with CD8 cells, NK cells, or both populations. No depletion (n=14), CD8 depletion (n=11), NK cell depletion (n=7), NK+CD8 cell depletion (n=11). Log-rank test was used to analyse the survival rates between groups. No depletion vs NK+CD8 depletion (**P=0.0014); No depletion vs NK (ns, P=0.4382); No depletion vs CD8 (ns, P=0.0795); NK vs CD8 (ns, P=0.1294); NK+CD8 cell depletion vs CD8 (* P=0.0114); NK+CD8 cell depletion vs NK (** P=0.0047).

Since the host IFN response is critical for metastasis suppression and the innate IFN pathway regulates the development and activity of immune effector cells (Dunn et al. 2005, supra), their potential role in this model was assessed by inoculating 4T1.2-BV or 4T1.2-Irf7 cells into NOD-SCID IL-2rγ$^{-/-}$ mice (NSG). Again, primary tumours grew at the same rate, suggesting primary tumour growth is not restrained by the immune system. Importantly, NSG mice lacking mature lymphocytes succumbed to metastasis more rapidly than syngeneic WT Balb/c mice and disease-free survival was not extended by expression of Irf7 (FIG. 4a)—in contrast to the outcome in immunocompetent mice where Irf7 had a significant survival benefit (FIG. 4a). These data demonstrate that functional immune cells are necessary for Irf7 protection against metastasis. Histological examination revealed spine metastases in all immunocompromised animals (FIG. 4b), consistent with their reduced survival. These results demonstrate that metastatic tumours are restrained by the immune system and that Irf7 possibly suppresses metastasis by restoring anti-tumour immune responses without impacting on primary tumour growth.

Figure 12:
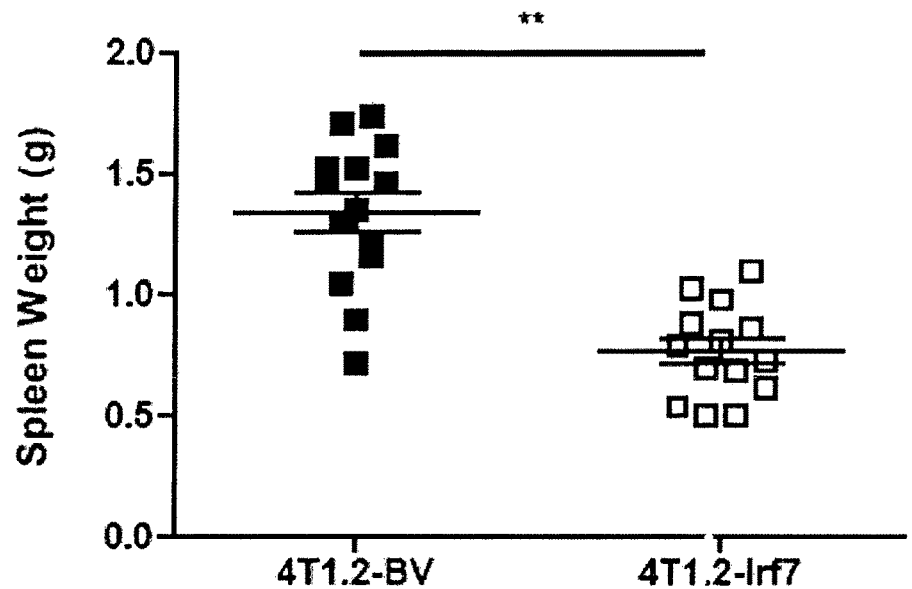
FIG. 12: Changes in haematological phenotypes in immunocompetent Balb/c mice bearing metastatic breast tumours. Spleen weight (a) and WBC count (b) in immunocompetent mice bearing 4T1.2-BV or 4T1.2-IRF7 tumours. (n=14, P<0.01).
Figure 12:
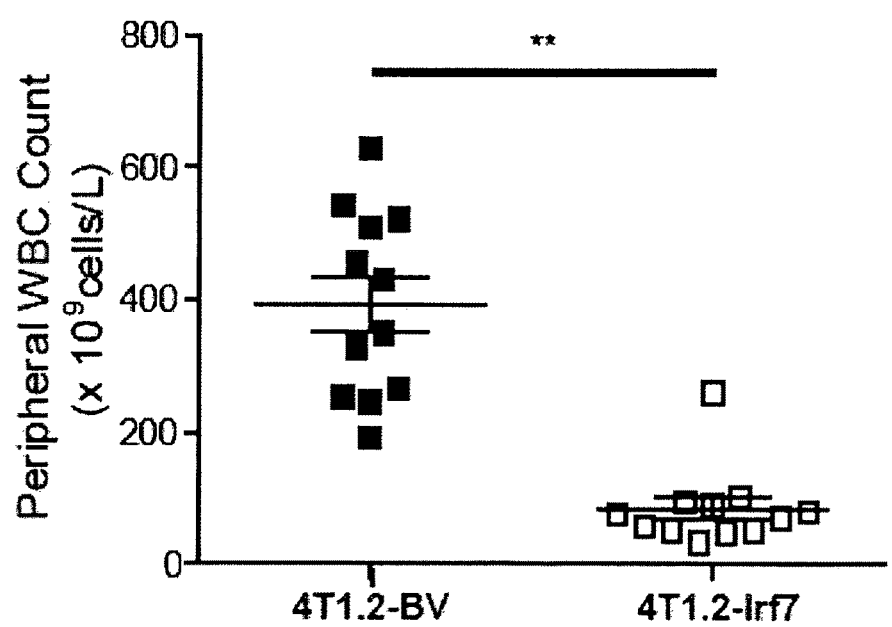
Figure 13:
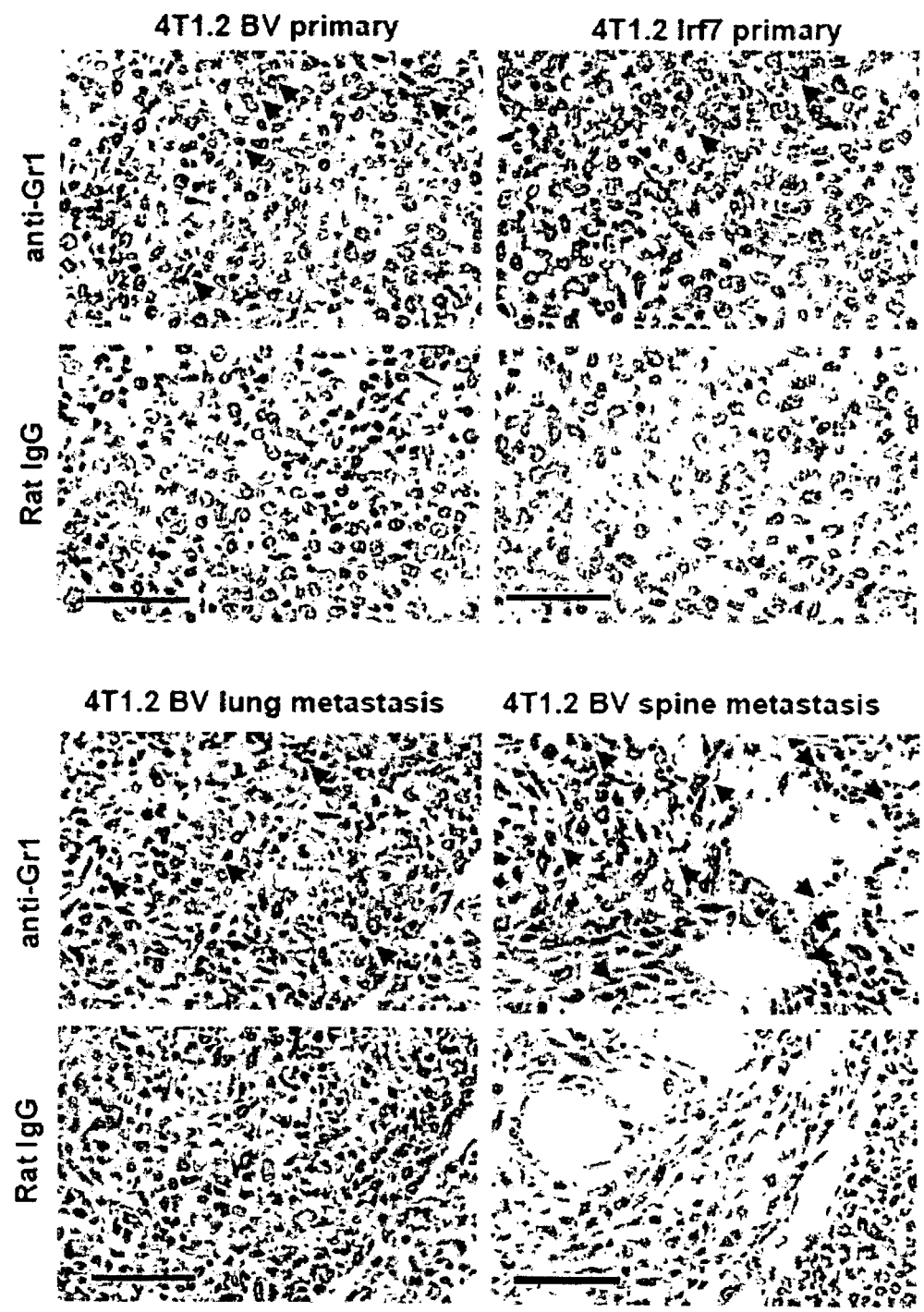
FIG. 13: Gr1 expression of 4T1.2 primary tumours and metastases. Samples of 4T1.2-BV primary tumours, lung metastases and spine metastases, along with 4T1.2-IRF7 primary tumours were stained for Gr1 and rat IgG (as indicated). Arrows indicated On positive cells. Scale bar=50 µm.
Figure 14:
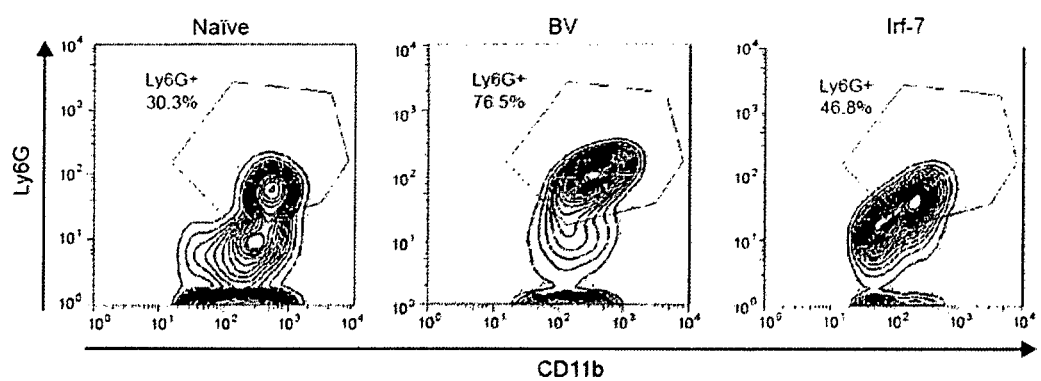
FIG. 14: Measurement of CD11b$^+$Ly6G$^+$ cells in tumour bearing mice. Representative image of flow cytometry plots of CD11b$^+$Ly6G$^+$ populations in the peripheral blood of naïve mice or mice bearing 4T1.2-BV or 4T1.2-IRF7 tumours.

To determine the immune cells mediating the Irf7-regulated modulation of bone metastases, systemic parameters of immune function were examined. Mice bearing 4T1.2-BV tumours have a marked elevation of peripheral white blood cells (WBCs) and splenomegaly compared to naïve mice. This response was reduced in mice bearing 4T1.2-Irf7 tumours (FIG. 12). Previous studies in the 4T1 model have detected an increase in myeloid-derived suppressor cells (MDSC) which suppress immune surveillance to promote tumour growth (Yang et al., *Cancer Cell* 13:23-35 (2008); DuPre and Hunter, *Exp Mol Pathol* 82:12-24 (2007). Gr1$^+$ CD11b$^+$ MDSC were measured in the peripheral blood of tumour bearing mice and detected a significant increase of this population in mice bearing the highly metastatic 4T1.2 tumours relative to 4T1.2-Irf7 or the non-bone metastatic variant, 66cl4 (FIG. 4c). MDSC infiltration into 4T1.2-Irf and 4T1.2-BV tumours was also visualized by immunohistochemical staining for Gr1-expressing cells (FIG. 13a). Gr1$^+$ cells were detected to a greater extent in bone metastases from mice bearing 4T1.2-BV tumours (FIG. 13b). Bone metastases from 4T1.2-Irf tumour-bearing mice were not detected. As MDSC consist of two major subsets, Ly6G+CD11b+ neutrophil-like MDSC and the Ly6G+CD11b+ monocytic MDSC (Youn et al., *J Immunol* 181: 5791-5802 (2008)), both populations were measured revealing a marked increase of Ly6G$^{hi}$ neutrophillic MDSC in all 4T1.2 tumour-bearing mice. The percentage Ly6G+CD11b+ cells were significantly reduced in 4T1.2-Irf7 compared to 4T1.2-BV mice (FIG. 14). To demonstrate the activity of Ly6G+CD11b+ MDSC, they were isolated from 4T1.2-bearing mice and demonstrated to inhibit proliferation of CD4+ or CD8+ T-lymphocytes (FIG. 4*d*). These data demonstrate that the MDSC population reduced in 4T1.2-Irf7 tumour-bearing mice is functionally capable of suppressing lymphocyte activity.

Figure 15:
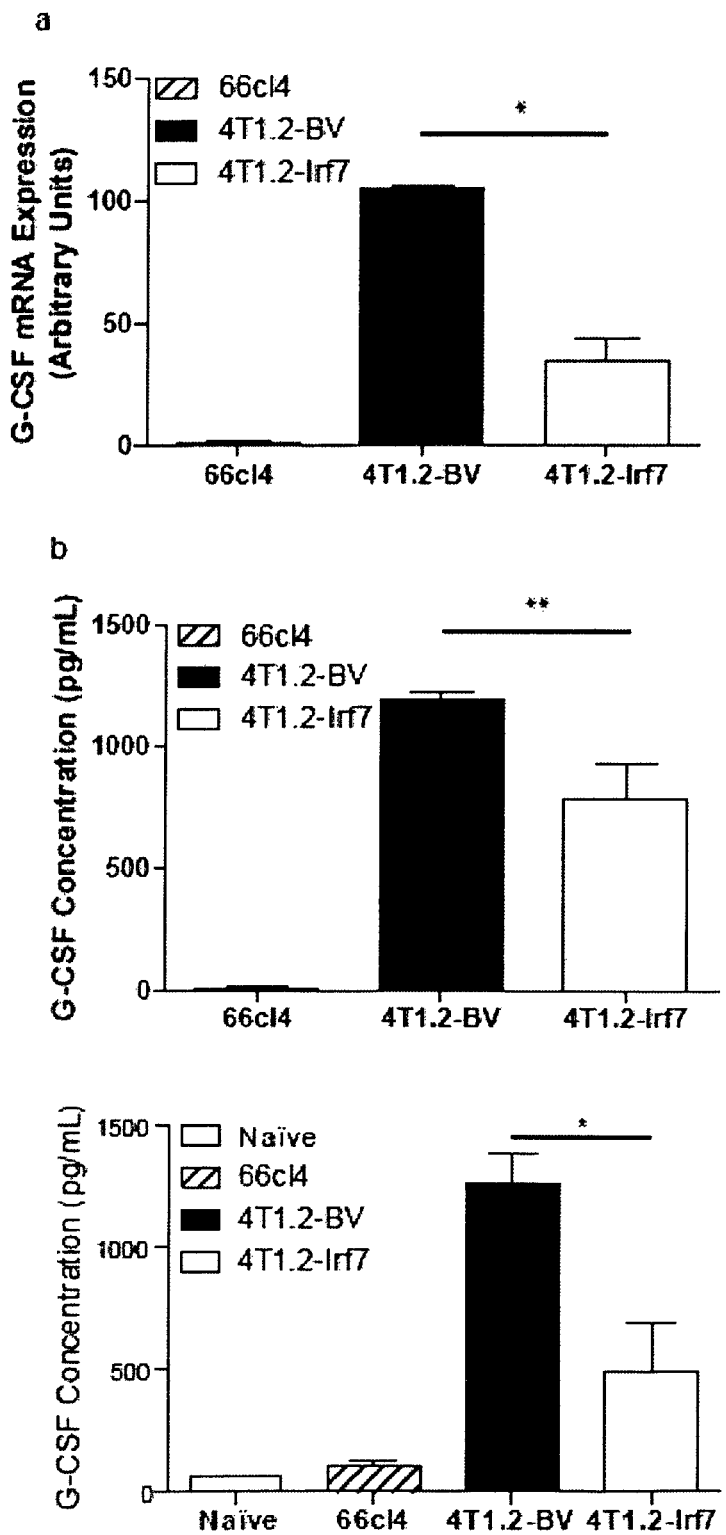
FIG. 15: G-CSF production in tumour-bearing immunocompetent mice. (a) G-CSF mRNA expression in primary tumours (n=5, *P<0.05). (b) G-CSF levels in primary tumour lysates (n=3) or in plasma (n=12) of mice bearing 66cl4, 4T1.2-BV or 4T1.2-IRF7 tumours or in naïve mice (++P<0.05).
Figure 16:
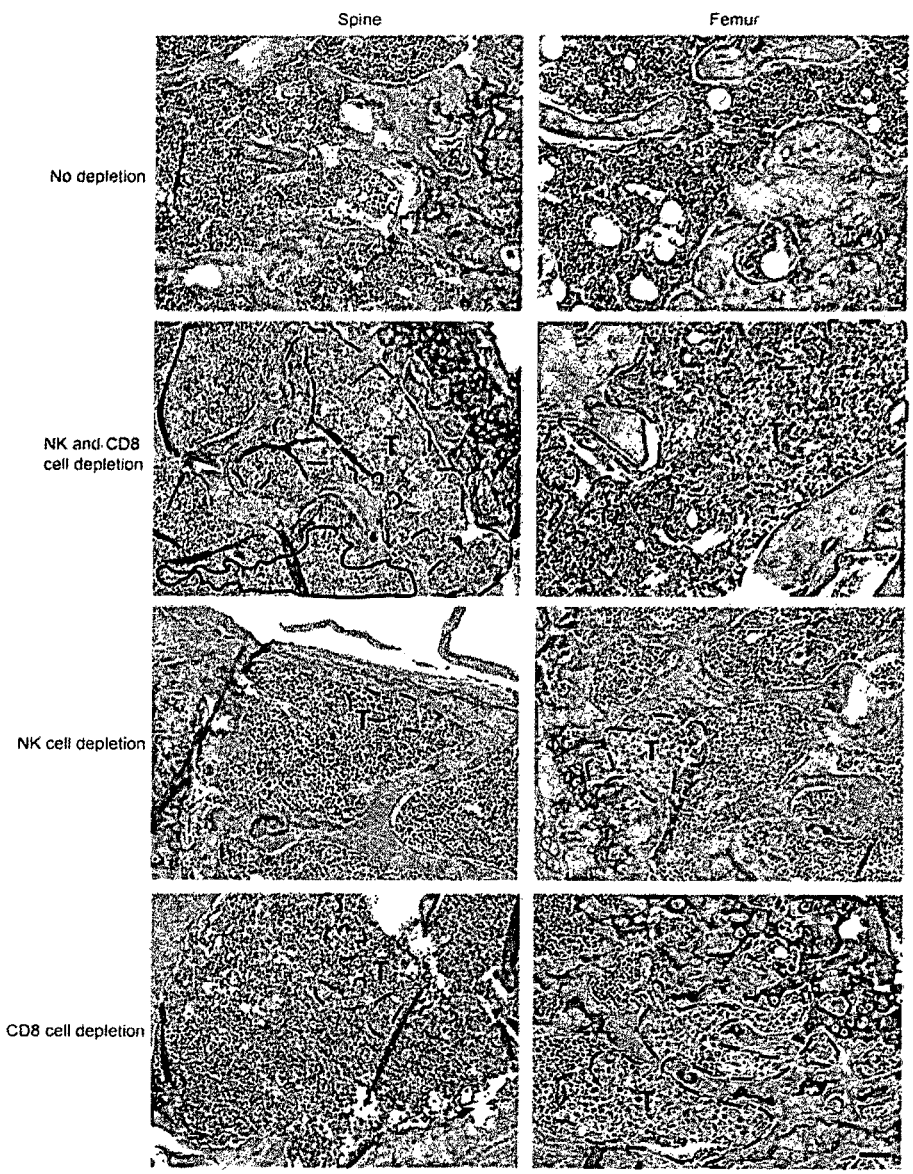
FIG. 16: Histopathological visualisation of bone metastases in mice depleted of NK cells and CD8$^+$ T cells. Sections of spines and femurs from mice bearing 4T1.2-IRF7 tumours and depleted of NK and or CD8$^+$ T cell s (as indicated) were H&E stained to visualise metastases. Dashed lines indicate tumour regions. T=tumour.

Previous reports linked tumour MDSC with granulocyte colony stimulating factor (G-CSF) (Waight et al., *PLoS One* 6:e27690 (2011); Adeegbe et al., *Cell Transplant* 20:941-954 (2011)). Significantly lower primary tumour and plasma levels of G-CSF were found in 4T1.2-Irf7 tumour-bearing mice than in 4T1.2-BV or non-bone metastatic 66cl4 tumour-bearing animals (FIG. 15). The reduction of MDSC in 4T1.2-Irf7 tumour-bearing mice, along with the ability of type I IFNs to directly enhance T cell and NK cell effector functions (Hervas-Stubbs et al., *Clin Cancer Res* 17:2619-2627 (2011)) suggests that enhanced tumour cell recognition may be involved in the suppression of metastasis mediated by Irf7. Consistent with this, a significant increase in CD4+, CD8+ and NK cell populations was observed in the peripheral blood of mice bearing 4T1.2-Irf7 tumours compared to 4T1.2-BV (FIG. 4*e*) at early time points, when cells are likely to have intravasated into the circulation but are yet to form metastases. To test their function, CD8+ T cells and NK cells were depleted from 4T1.2-Irf7 tumour- and 4T1.2-BV tumour-bearing mice. As with all previous in vivo experiments, primary tumour growth was unaltered by depletion of either or both cell types (FIG. 4*f*). However, depletion of both CD8+ T cells and NK cells significantly accelerated metastasis and shortened survival (FIG. 4*g*), indicating that both of these effector cells contribute to the Irf7/IFN-mediated control of metastases. Importantly, an obvious increase in paralysis in these mice caused by the development of bone metastases was observed and was confirmed by histology (FIG. 16). In summary, these data confirm that Irf7 induced IFN-dependent immune suppression of metastasis to bone was dependent on CD8+ T cells and NK cells.

IRF7 Pathway in Human Breast Cancer

Figure 5:
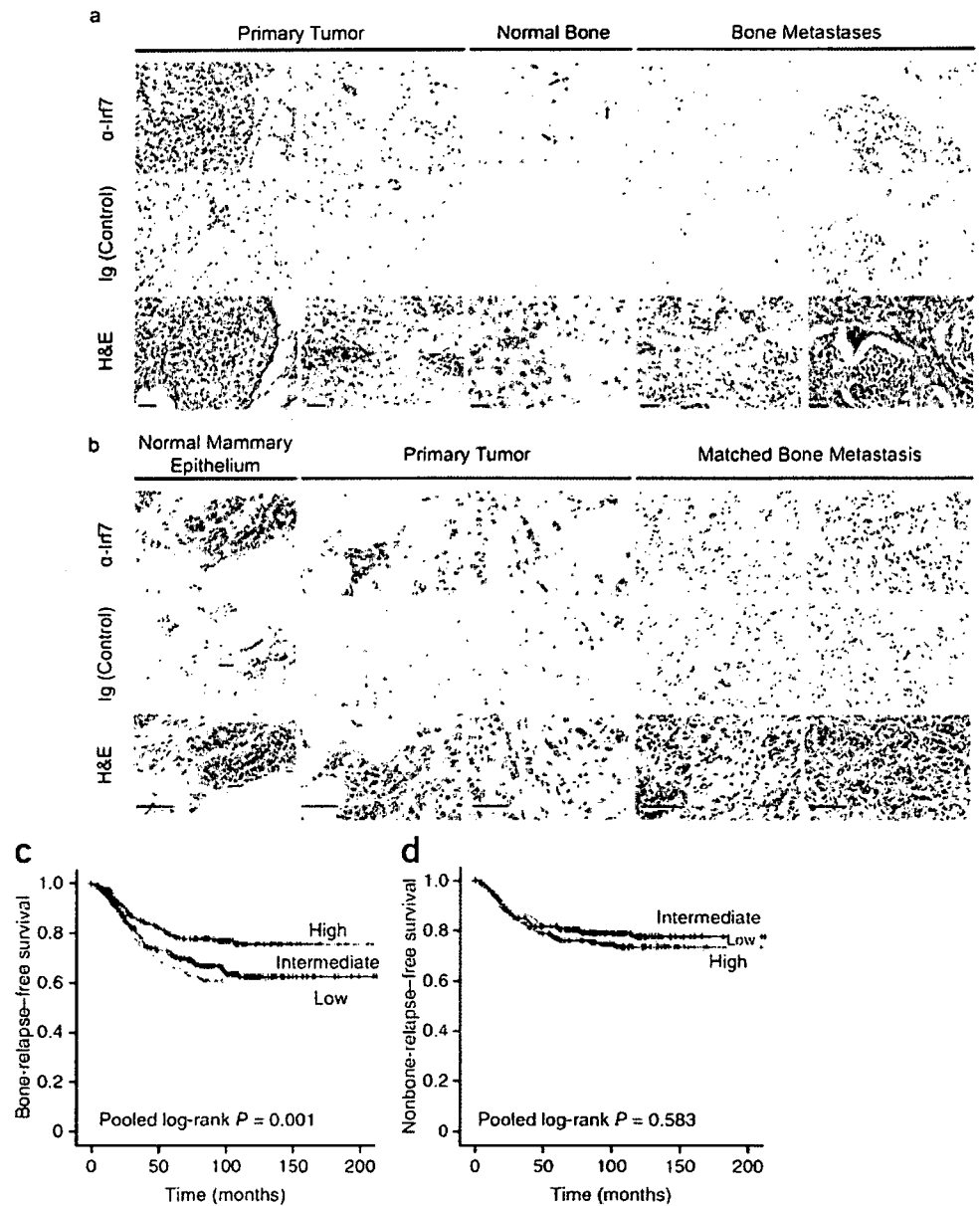
FIG. 5: IRF7 expression in human breast cancer metastases. (a) Samples of unmatched primary breast tumours and bone metastases as well as normal bone stained for IRF7, Ig control and H&E (as indicated). Arrows indicate osteocyte staining. Scale bar=50 µm. (b) Primary breast tumour and a matched bone metastasis stained for IRF7, Ig control and H&E. Also shown is normal mammary epithelium from a breast reduction mammoplasty for comparison. Scale bar=50 µm. (c) IRF7 pathway activity as measured by gene expression in human breast cancers and significant association with bony metastases as first site of distant relapse. Y axis on Kaplan-Meier curve represents "Bone Relapse-free survival", X axis is time in months. Purple, black and blue represents highest, intermediate and lowest tertile of expression of the IRF7 gene signature respectively. Log-rank p value is calculated pooled across the three strata. (d) The IRF7 gene signature is not significantly associated with non-bony relapses (brain, liver, lung).

The expression of IRF7 in primary tumours and its loss in distant metastases, including bone, was verified by IHC using tissue arrays derived from the Rapid Autopsy Program, Johns Hopkins Hospital (Wu et al., *Clin Cancer Res* 14:1938-1946 (2008)). In these cases, it was demonstrated that IRF7 was frequently expressed in normal breast tissue (7/10) and in primary tumours (9/16). Importantly, reduced IRF7 expression was observed in metastases, with only 16.7% of distant metastases expressing IRF7 (3/18), (P<0.04 relative to primary tumours, Table 6). Analysis of matched primary tumours and bone metastases within this cohort revealed that of 9 pairs, 7 primaries expressed IRF7, only one of which retained expression in the matched bone metastasis (representative images in FIG. 5*a,b*). As also shown in mouse tissues (FIG. 2*b*), bone osteocytes expressed IRF7 whereas the tumour cells were negative in most cases.

In order to determine the clinical relevance of the IRF7 pathway in human breast cancers, publicly available gene expression datasets of 855 primary tumours with known location of first site of distant metastases were used (Minn et al. *Nature* 436:518-524 (2005); Harrell et al. *Breast Cancer Res Treat* 132:523-535 (2012)). Using the 208 genes previously predicted as being Irf7-regulated (FIG. 1, FIG. 7) associations between this Irf7 signature, relapses to bone and non-bone as the first site of distant metastases were evaluated. Interestingly, it was found that the Irf7 signature was significantly associated with bone metastases-free survival in a linear manner, with low expression of the Irf7-gene set associated with increased bone metastatic events (FIG. 5*c*) whereas no relationship was observed for other sites (brain, lung and liver, FIG. 5*d*). The ability to predict bone metastases was independent of estrogen receptor status, lymph node involvement, tumour size and histological grade (adjusted hazard ratio HR:0.63 (95% CI:0.42-0.93) P=0.021). Overall, these results support the mouse data that the Irf7 pathway is important for the suppression of bone metastases in human breast cancer.

Treatment with IFN-$\alpha_1$ Suppresses Metastasis

Figure 6:
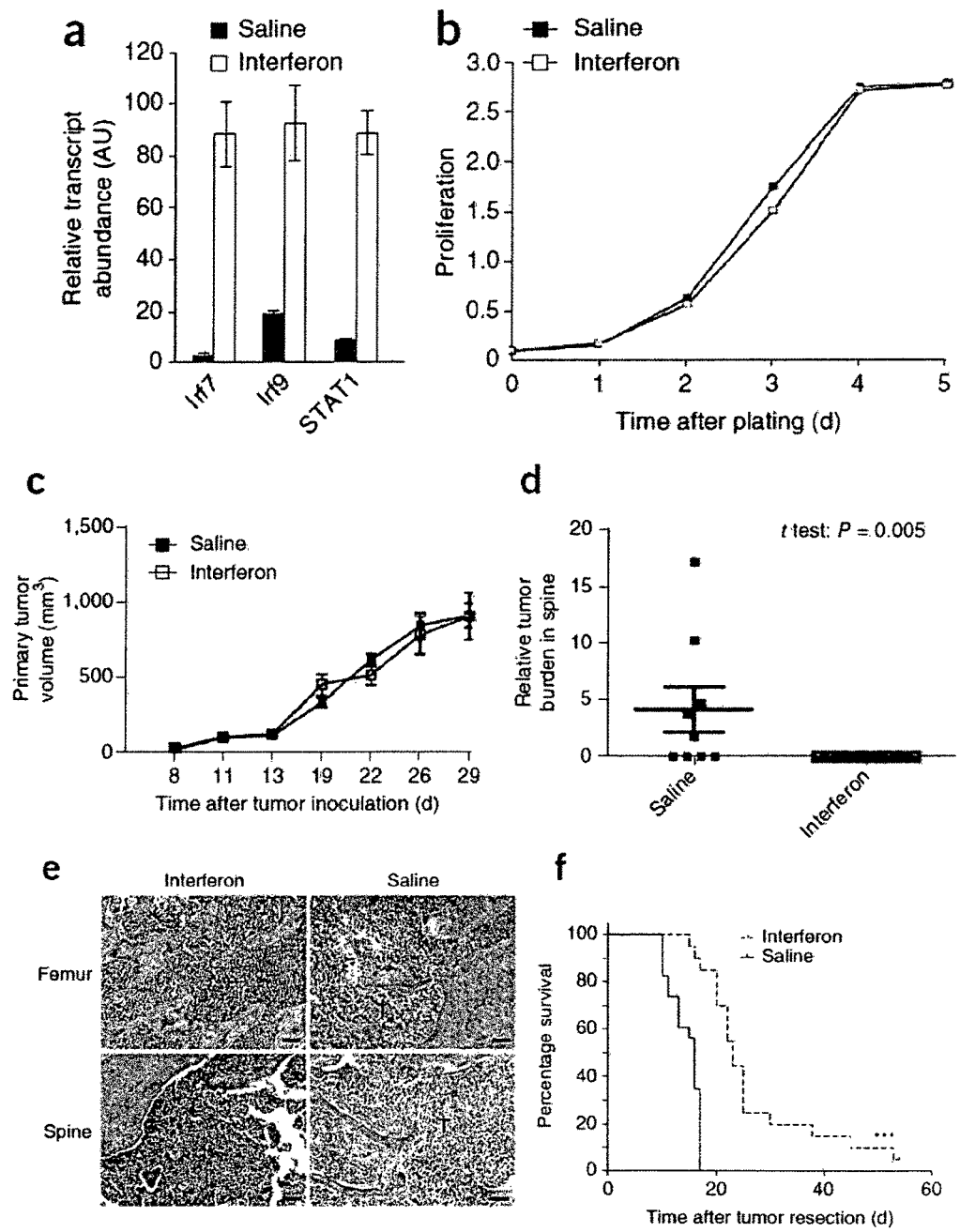
FIG. 6: The effect of type I IFN treatment on metastasis. (a) Real-time RT-PCR analysis of 4T1.2 cells treated with 10001 U/mL recombinant IFN-$\alpha_1$. (n=3, * p<0.05, error bars are S.E.M.). (b) Proliferation of 4T1.2 cells treated with 1000 IU/mL of recombinant IFN$_{+1}$. (n=6, error bars are S.E.M.). (c) Primary tumour volume, n=15. (d) Q-PCR detection of metastatic 4T1.2 tumour burden in spine (at day 33 post tumour cell inoculation) of mice treated with IFN$_{\alpha 1}$ or vehicle. (e) H&E stained sections of spines and femurs from 4T1.2 bearing mice treated with IFN-$_{\alpha 1}$ or vehicle (Scale bar=50 T=Tumour). (f) Kaplan-Meier disease-free survival analysis of mice bearing 4T1.2 tumours that were subsequently resected. Mice were treated with 10$^5$ IU of recombinant IFN-$\alpha$1 or saline from day 3. (n=15).
Figure 17:
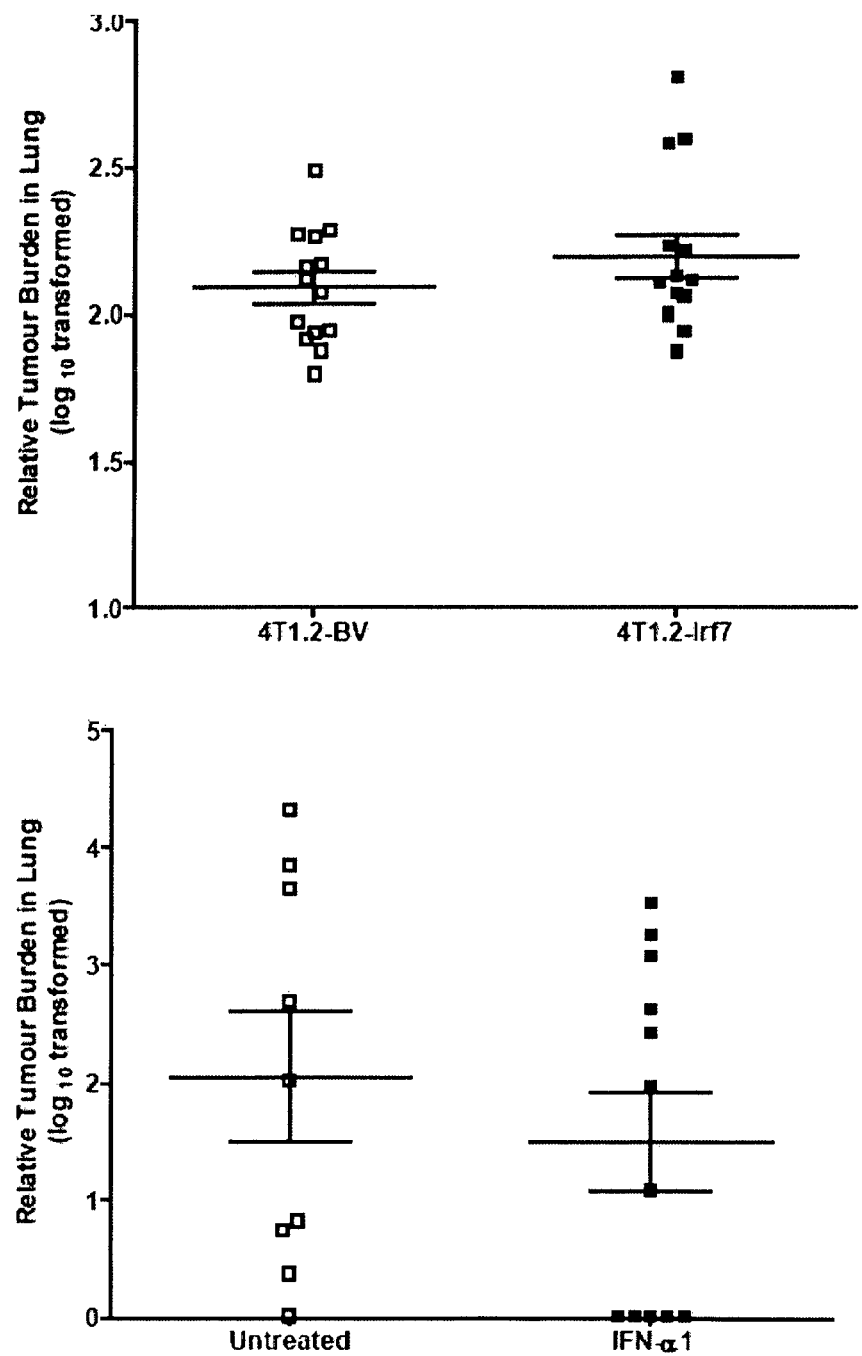
FIG. 17: Quantitation of lung metastases in mice bearing 4T1.2 tumours. Q-PCR detection of metastatic tumour burden in spines of 4T1.2-BV and 4T1.2-IRF7 tumour burdened mice (endpoint, day 32), or 4T1.2-BV mice treated with saline or IFNα1 (endpoint, day 33).
Figure 18:
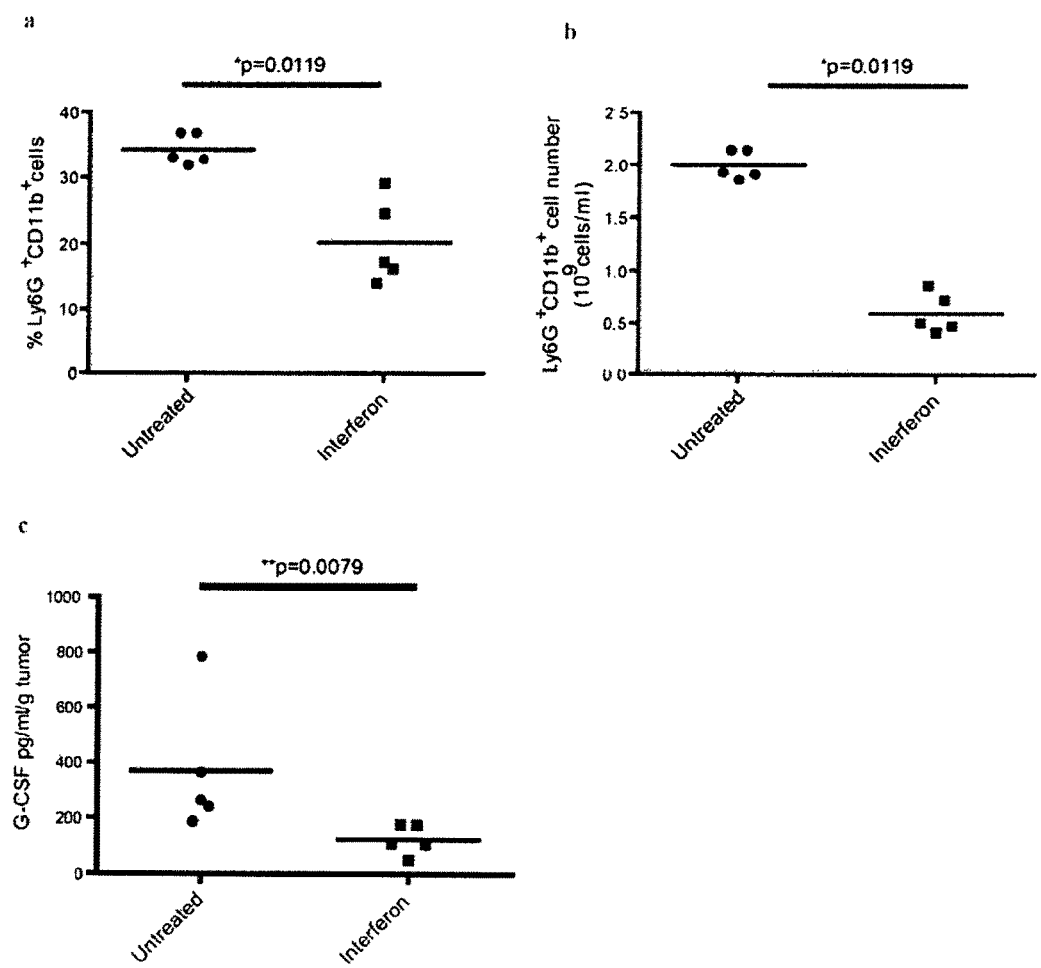
FIG. 18: Measurement of MDSC and G-CSF in blood of 4T1.2 tumour bearing mice treated with IFNα1. Mice were treated with IFN-al or saline control one day after 4T1.2 tumour cell inoculation into the mammary gland. Five days after tumour inoculation, MDSC percentage (a) and absolute numbers (b) were measured, along with G-CSF levels by ELISA (c).

Since Irf7 metastasis suppression was reliant on type I IFN, it was sought to determine whether IFN administration would reverse metastatic burden in bone. IFN-$\alpha_1$ treatment increased expression of Irf7, as well as Irf9 and STAT1 in 4T1.2 cells in vitro (FIG. 6*a*), consistent with the data demonstrating that Irf7 increased Irf9 and STAT1 expression via IFN. As expected from our data above, IFN$_{\alpha 1}$ treatment did not affect 4T1.2 cell proliferation in vitro (FIG. 6*b*) or primary tumour growth in vivo (FIG. 6*c*). In stark contrast, IFN treatment significantly reduced metastasis to the spine and femur to undetectable levels (P<0.007) (FIG. 6*d, e*). The extent of metastasis to lung was not reduced (FIG. 17) decreased MDSC accumulation and G-CSF levels were observed in the peripheral blood in IFN-treated mice (FIG. 18 For metastasis-free survival studies, 4T1.2-bearing mice were treated with either saline or IFN-$\alpha_1$ for five weeks, with primary tumour resection at 3 weeks. Again, IFN-$\alpha_1$ had no effect on the growth of primary tumours, but resulted in a significant extension of metastasis-free survival (FIG. 6*f*). At end point, all mice in this analysis succumbed to bone and lung metastases. These data demonstrate that therapeutic administration of IFN-α1 can reduce metastatic burden and is a viable therapeutic strategy worthy of further investigation.

Figure 19:
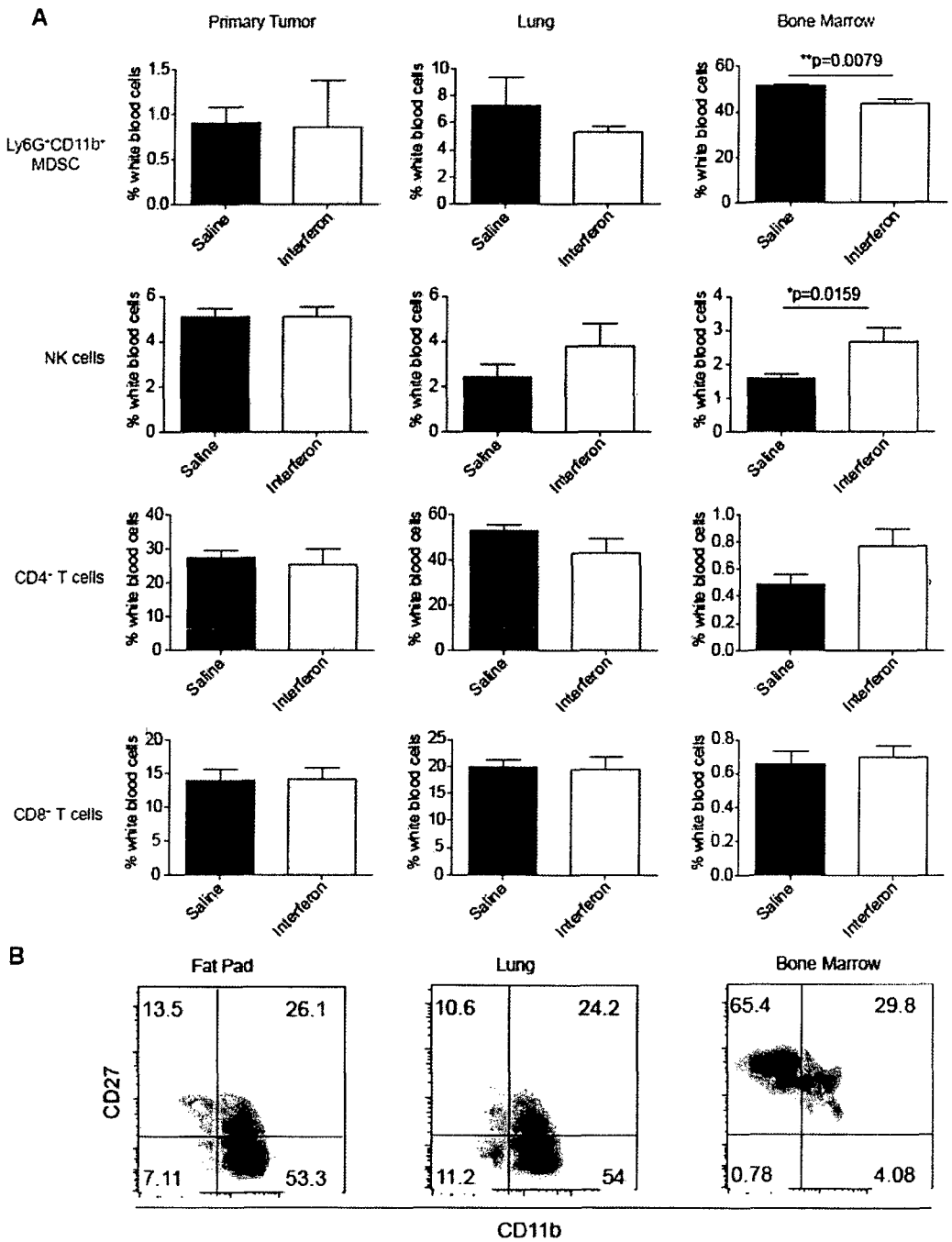
FIG. 19: Changes in immune cells in the mammary gland, lung and bone. a) Mice were treated with IFN-α1 or saline control on day 1, 3 and 5 after 4T1.2 tumour cell inoculation into the mammary gland. Ten days after tumour inoculation MDSC, NK, CD4$^+$ and CD8$^+$ T cell percentages were measured in fatpad/primary tumour, lung and bone marrow. N=5. Difference between treatment groups was assessed using an unpaired T test and significance is indicated. b) Cells isolated from the mammary gland, lung and bone marrow of naïve Balb/c mice were stained for DX5, TCR, CD11b and CD27. Shown are representative profiles for CD11b and CD27 expression on gated DX5$^+$TCR. Percentage of CD11b$^{low/high}$ and/or CD27$^{low/high}$ are indicated.

In order to provide insights into the mechanism of IFN inhibition of bone metastases specifically, the effect of IFN treatment on immune cell populations in tumour bearing animals was measured. The percentage of CD11b+Ly6G+ MDSC was far greater in the bone marrow compared to lung and mammary gland (FIG. 19 Importantly, IFN treatment significantly decreased MDSC in the bone marrow and peripheral blood (FIG. 18, 19*a*) but not in the mammary gland/primary tumour or in the lungs (FIG. 19). Additionally, NK cells were significantly increased in the bone marrow following IFN treatment, an effect that was not observed at the primary site or in lungs of tumour-bearing animals (FIG. 19*a*). These data show that IFN reduces immune suppressor cells and increases effectors specifically in the bone marrow. In addition, NK cells from the mammary gland and lungs were predominantly CD11b$^{high}$/CD27$^{low}$ (FIG. 19*b*), indicative of terminally differentiated cells that have a higher threshold for stimulation (Hayakawa and Smyth, *J Immunol* 176:1517-1524 (2006)). In contrast, the majority of NK cells from the bone marrow were CD11b$^{low}$/CD27$^{high}$ (FIG. 10*b*), representing NK cells with greater effector function that are reportedly more sensitive to stimulation by cytokines such as IFN.

Together these data imply that the mechanism whereby IFN specifically inhibits bone metastases of mammary cancers is by selective modulation of MDSC and NK effectors in bone marrow.

Figure 20:
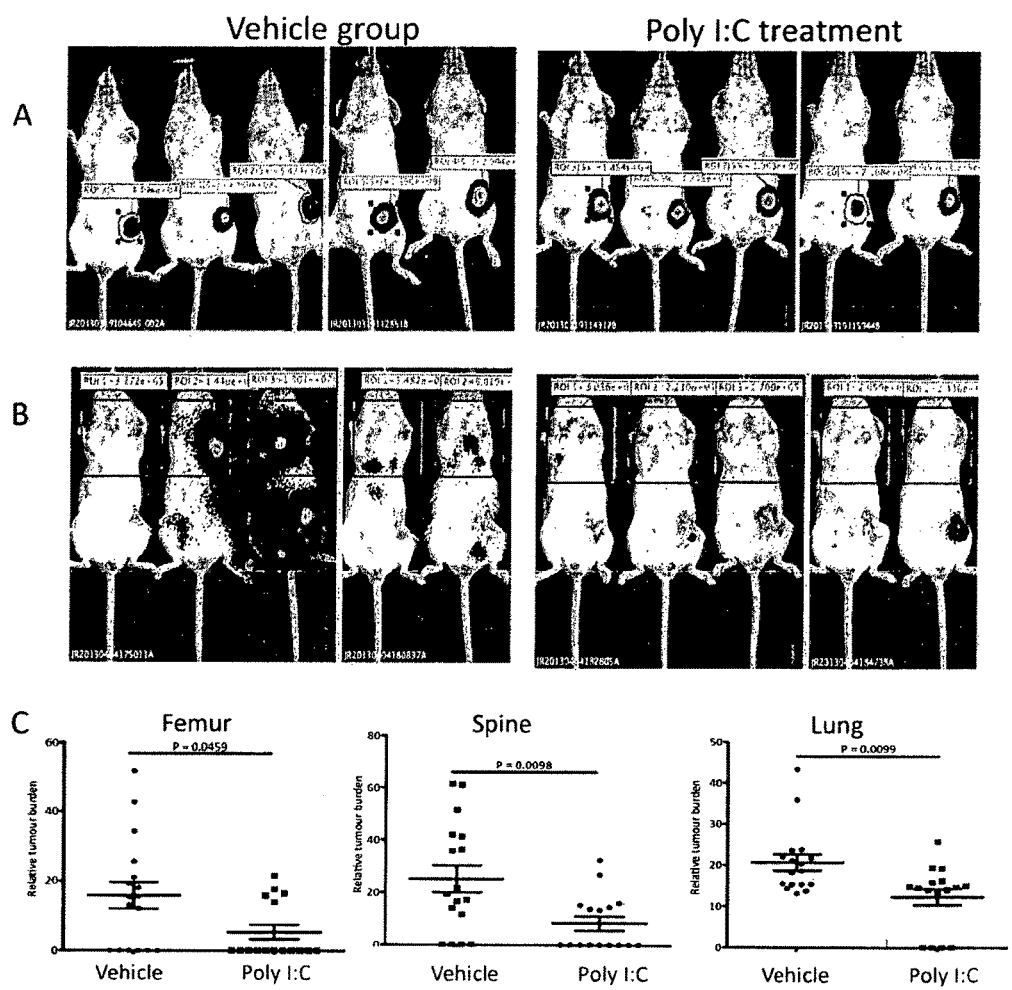
FIG. 20: Treatment with the IFN agonist poly I:C suppresses metastasis. Mice bearing 4T1.2 cells were treated with 25 ug poly I:C 3× weekly by tail vein injection beginning at day 3. (a) Bioluminescence imaging of 4T1.2 primary tumour burden prior to surgical resection (b) Bioluminescence imaging of metastatic burden in mice treated with vehicle or poly I:C (c) Q-PCR detection of 4T1.2 tumour burden in femur, spine and lung of mice at day 33.

These studies revealed that one such type I IFN (IFNα1) could suppress metastasis to bone. To determine whether metastasis suppression could be even more potent with an agonist of the pathway that stimulates expression of multiple type I IFNs, 4T1.2 bearing mice were treated with the TLR3 agonist poly I:C that mimics a double-stranded viral infection. Treatment of mice bearing 4T1.2 tumours with poly I:C did not alter primary tumour growth, as confirmed by bioluminescence imaging (FIG. 20a). However, after primary tumour resection, it became clear by bioluminescence that poly I:C treatment suppressed metastasis to multiple organs (FIG. 20b). This was confirmed and quantitated by PCR detection of tumour cell markers in distant organs, where we observed a significant decrease in metastatic burden in lung and bone in the treatment group (FIG. 20c).

Figure 21:
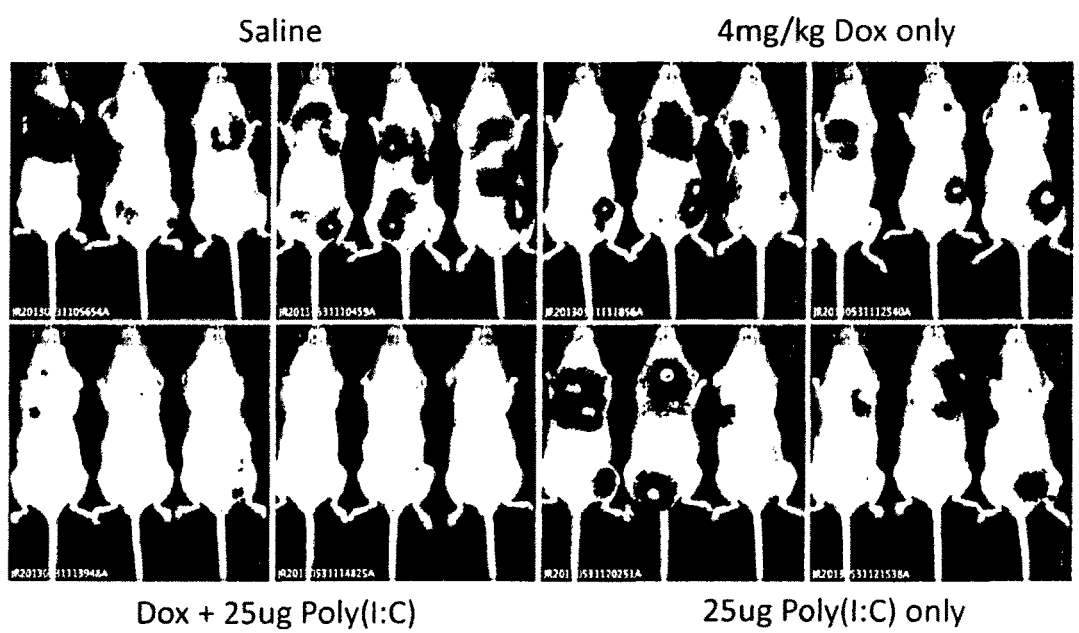
FIG. 21: Combination of poly I:C and doxorubicin reduces metastasis in an early treatment setting. 4T1.2 cells were inoculated into the 4$^{th}$ mammary gland of Balb/c mice. Primary tumours were resected when they reached 0.2 g and 2 days later treatment was started for a period of 2 weeks. Mice were treated with vehicle alone, 25 ug poly I:C every 2 days, 4 mg/kg doxorubicin every 4 days, or the combination of poly I:C and doxorubicin. Metastatic burden was visualised in all mice at a set time point using bioluminescence imaging.
Figure 22:
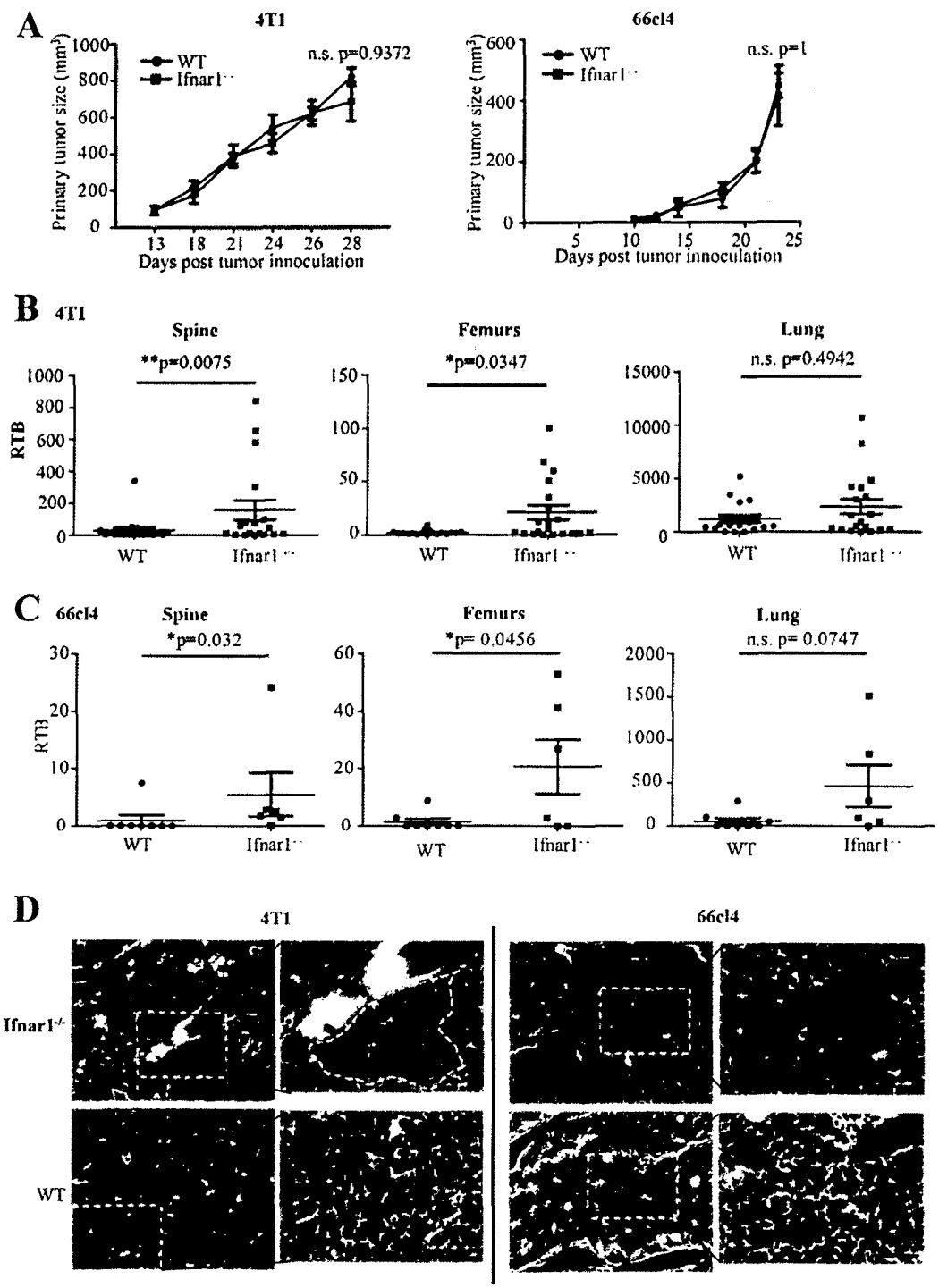
FIG. 22: Blocking type I IFN signaling using mice deficient in Ifnar1 enhances bone metastasis in weakly (4T1) and non-metastatic (66cl4) breast cancer models. (a) primary tumour growth of 4T1 and 66cl4 tumours. (b) Metastatic burden in mice bearing 4T1 tumours (day 32 without resection). (c) Metastatic burden in mice bearing 66cl4 tumors (day 21 after resection). RTB, relative tumour burden. (d) Representative H&E-stained sections of femurs from mice bearing 4T1 and 66cl4 tumors at endpoint. Scale bar, 50 T represents a tumour region.

The dose of poly I:C was reduced by mimicking an early treatment setting and initiating treatment after primary tumour removal for only 2 weeks, before the detection of large metastases. Also evaluated was the value of combining poly I:C treatment with a commonly used chemotherapeutic, doxorubicin. Although the single agents did not significantly impact metastasis alone in this short-treatment setting, the combination was very effective, with an obvious reduction in metastasis at end point (FIG. 21). This work indicates that combining IFN agonists with chemotherapeutics has potent anti-metastatic effects, even at reduced doses.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3 a

| Category | Genes in Category | % Genes in Category | Genes in List in Category | % Genes in List in Category | P-Value |
| --- | --- | --- | --- | --- | --- |
| GO: 6952: defense response | 704 | 3.084 | 71 | 6.58 | 1.50E−09 |
| GO: 9607: response to biotic stimulus | 716 | 3.136 | 71 | 6.58 | 3.08E−09 |
| GO: 6955: immune response | 548 | 2.401 | 55 | 5.097 | 1.28E−07 |
| GO: 6935: chemotaxis | 127 | 0.556 | 21 | 1.946 | 5.23E−07 |
| GO: 6898: receptor mediated endocytosis | 18 | 0.0789 | 7 | 0.649 | 1.04E−05 |
| GO: 50896: response to stimulus | 1556 | 6.816 | 108 | 10.01 | 3.49E−05 |
| GO: 50874: organismal physiological process | 1320 | 5.782 | 94 | 8.712 | 4.48E−05 |
| GO: 9605: response to external stimulus | 512 | 2.243 | 45 | 4.171 | 5.13E−05 |
| GO: 42221: response to chemical stimulus | 251 | 1.1 | 27 | 2.502 | 6.20E−05 |
| GO: 9613: response to pest, pathogen or parasite | 315 | 1.38 | 30 | 2.78 | 0.000227 |
| GO: 43207: response to external biotic stimulus | 323 | 1.415 | 30 | 2.78 | 0.000349 |
| GO: 9628: response to a biotic stimulus | 363 | 1.59 | 32 | 2.966 | 0.000563 |
| GO: 6956: complement activation | 43 | 0.188 | 8 | 0.741 | 0.000804 |
| GO: 6959: humoral immune response | 100 | 0.438 | 13 | 1.205 | 0.000856 |
| GO: 8361: regulation of cell size | 106 | 0.464 | 13 | 1.205 | 0.00148 |
| GO: 7585: respiratory gaseous exchange | 28 | 0.123 | 6 | 0.556 | 0.00169 |
| GO: 1701: embryonic development | 12 | 0.0526 | 4 | 0.371 | 0.00181 |
| GO: 6954: inflammatory response | 149 | 0.653 | 16 | 1.483 | 0.00187 |
| GO: 1558: regulation of cell growth | 84 | 0.368 | 11 | 1.019 | 0.00197 | b
Interferon Stimulated Response Element

| Sequence | Distance | Expected Frequency | Observed Frequency | Genes Analysed | P-value |
| --- | --- | --- | --- | --- | --- |
| AGTTTCNNCNY | 500 | 16.78 | 59 | 1282 | 1.98E−09 |
| AGTTTCNNCNY | 1000 | 37.35 | 95 | 1282 | 2.40E−09 |
| AGTTTCNNCNY | 2000 | 78.5 | 169 | 1282 | 7.70E−09 |
| AGTTTCNNCNY | 5000 | 192.3 | 362 | 1282 | 2.75E−09 |

Global gene changes observed in highly metastatic primary tumors versus bone metastases. (a) Top 20 most significant gene ontologies. Highlighted in grey are ontologies related to immune regulation. (b) Frequency that interferon stimulated response element (ISRE) was observed in untranslated upstream regions of genes significantly altered between primary tumors and metastases that were in immune related ontologies, in a preliminary analysis of all known promoter regions upstream of ORFs. This result lead to analysis of the dataset with the INTERFEROME analysis package.

TABLE 4

| | | | |
| --- | --- | --- | --- |
| ENSMUSG00000035373 | ENSMUSG00000048779 | ENSMUSG00000015340 | ENSMUSG00000023175 |
| ENSMUSG00000019987 | ENSMUSG00000032314 | ENSMUSG00000020641 | ENSMUSG00000004814 |
| ENSMUSG00000026981 | ENSMUSG00000024621 | ENSMUSG00000022150 | ENSMUSG00000004371 |
| ENSMUSG00000021190 | ENSMUSG00000030786 | ENSMUSG00000025019 | ENSMUSG00000022781 |
| ENSMUSG00000003617 | ENSMUSG00000054766 | ENSMUSG00000024661 | ENSMUSG00000026193 |
| ENSMUSG00000030096 | ENSMUSG00000027435 | ENSMUSG00000014956 | ENSMUSG00000026896 |
| ENSMUSG00000025804 | ENSMUSG00000046879 | ENSMUSG00000026356 | ENSMUSG00000022346 |
| ENSMUSG00000020572 | ENSMUSG00000055172 | ENSMUSG00000036112 | ENSMUSG00000016541 |
| ENSMUSG00000027800 | ENSMUSG00000030342 | ENSMUSG00000024675 | ENSMUSG00000030846 |

TABLE 4-continued

| | | | |
|---|---|---|---|
| ENSMUSG00000049723 | ENSMUSG00000027206 | ENSMUSG00000031712 | ENSMUSG00000001175 |
| ENSMUSG00000032554 | ENSMUSG00000048490 | ENSMUSG00000036606 | ENSMUSG00000021520 |
| ENSMUSG00000002602 | ENSMUSG00000038014 | ENSMUSG00000021178 | ENSMUSG00000022052 |
| ENSMUSG00000025283 | ENSMUSG00000025044 | ENSMUSG00000029767 | ENSMUSG00000070348 |
| ENSMUSG00000016529 | ENSMUSG00000036322 | ENSMUSG00000025917 | ENSMUSG00000024659 |
| ENSMUSG00000046031 | ENSMUSG00000044583 | ENSMUSG00000022010 | ENSMUSG00000047554 |
| ENSMUSG00000039146 | ENSMUSG00000071713 | ENSMUSG00000043998 | ENSMUSG00000028932 |
| ENSMUSG00000035385 | ENSMUSG00000027087 | ENSMUSG00000003131 | ENSMUSG00000046718 |
| ENSMUSG00000024486 | ENSMUSG00000038067 | ENSMUSG00000054889 | ENSMUSG00000028466 |
| ENSMUSG00000045932 | ENSMUSG00000028270 | ENSMUSG00000019850 | ENSMUSG00000015806 |
| ENSMUSG00000047250 | ENSMUSG00000069874 | ENSMUSG00000001999 | ENSMUSG00000002897 |
| ENSMUSG00000038507 | ENSMUSG00000015961 | ENSMUSG00000025702 | ENSMUSG00000021427 |
| ENSMUSG00000019916 | ENSMUSG00000052681 | ENSMUSG00000037868 | ENSMUSG00000067219 |
| ENSMUSG00000027962 | ENSMUSG00000034640 | ENSMUSG00000033088 | ENSMUSG00000021116 |
| ENSMUSG00000067284 | ENSMUSG00000059498 | ENSMUSG00000041936 | ENSMUSG00000060802 |
| ENSMUSG00000068823 | ENSMUSG00000058818 | ENSMUSG00000024150 | ENSMUSG00000026484 |
| ENSMUSG00000029371 | ENSMUSG00000000628 | ENSMUSG00000028961 | ENSMUSG00000017830 |
| ENSMUSG00000024371 | ENSMUSG00000034789 | ENSMUSG00000000420 | ENSMUSG00000019795 |
| ENSMUSG00000019960 | ENSMUSG00000018930 | ENSMUSG00000028128 | ENSMUSG00000029017 |
| ENSMUSG00000017057 | ENSMUSG00000079293 | ENSMUSG00000025498 | ENSMUSG00000031878 |
| ENSMUSG00000056758 | ENSMUSG00000032359 | ENSMUSG00000000787 | ENSMUSG00000031639 |
| ENSMUSG00000018920 | ENSMUSG00000015932 | ENSMUSG00000022257 | ENSMUSG00000027852 |
| ENSMUSG00000033880 | ENSMUSG00000043587 | ENSMUSG00000052837 | ENSMUSG00000006728 |
| ENSMUSG00000061232 | ENSMUSG00000044786 | ENSMUSG00000026535 | ENSMUSG00000015656 |
| ENSMUSG00000029417 | ENSMUSG00000004730 | ENSMUSG00000021282 | ENSMUSG00000030142 |
| ENSMUSG00000024521 | ENSMUSG00000026628 | ENSMUSG00000025809 | ENSMUSG00000027639 |
| ENSMUSG00000026750 | ENSMUSG00000022285 | ENSMUSG00000031278 | ENSMUSG00000024912 |
| ENSMUSG00000021477 | ENSMUSG00000034947 | ENSMUSG00000061878 | ENSMUSG00000028976 |
| ENSMUSG00000040552 | ENSMUSG00000034120 | ENSMUSG00000028249 | ENSMUSG00000021036 |
| ENSMUSG00000041827 | ENSMUSG00000028214 | ENSMUSG00000039682 | ENSMUSG00000041058 |
| ENSMUSG00000034394 | ENSMUSG00000015766 | ENSMUSG00000029186 | ENSMUSG00000001440 |
| ENSMUSG00000034438 | ENSMUSG00000029761 | ENSMUSG00000062014 | ENSMUSG00000020432 |
| ENSMUSG00000057666 | ENSMUSG00000040158 | ENSMUSG00000018199 | ENSMUSG00000079477 |
| ENSMUSG00000078088 | ENSMUSG00000017493 | ENSMUSG00000004085 | ENSMUSG00000024851 |
| ENSMUSG00000078142 | ENSMUSG00000034855 | ENSMUSG00000027479 | ENSMUSG00000060680 |
| ENSMUSG00000078162 | ENSMUSG00000030107 | ENSMUSG00000016534 | ENSMUSG00000027566 |
| ENSMUSG00000078965 | ENSMUSG00000078153 | ENSMUSG00000039501 | ENSMUSG00000062070 |
| ENSMUSG00000078967 | ENSMUSG00000033379 | ENSMUSG00000034684 | ENSMUSG00000027340 |
| ENSMUSG00000079501 | ENSMUSG00000030161 | ENSMUSG00000029380 | ENSMUSG00000078920 |
| ENSMUSG00000032369 | ENSMUSG00000047945 | ENSMUSG00000037411 | ENSMUSG00000032374 |
| ENSMUSG00000051355 | ENSMUSG00000017652 | ENSMUSG00000033355 | ENSMUSG00000031168 |
| ENSMUSG00000027398 | ENSMUSG00000074305 | ENSMUSG00000022817 | ENSMUSG00000022014 |
| ENSMUSG00000026836 | ENSMUSG00000037921 | ENSMUSG00000022216 | ENSMUSG00000032698 |
| ENSMUSG00000029798 | ENSMUSG00000005148 | ENSMUSG00000028410 | ENSMUSG00000017715 |
| ENSMUSG00000029287 | ENSMUSG00000037236 | ENSMUSG00000046223 | ENSMUSG00000000290 |
| ENSMUSG00000021589 | ENSMUSG00000007815 | ENSMUSG00000025779 | ENSMUSG00000036427 |
| ENSMUSG00000022094 | ENSMUSG00000027293 | ENSMUSG00000067194 | ENSMUSG00000028124 |
| ENSMUSG00000018398 | ENSMUSG00000028837 | ENSMUSG00000023206 | ENSMUSG00000036353 |
| ENSMUSG00000079227 | ENSMUSG00000028793 | ENSMUSG00000034652 | ENSMUSG00000054277 |
| ENSMUSG00000047407 | ENSMUSG00000031996 | ENSMUSG00000026083 | ENSMUSG00000070544 |
| ENSMUSG00000006273 | ENSMUSG00000019923 | ENSMUSG00000039285 | ENSMUSG00000052593 |
| ENSMUSG00000021281 | ENSMUSG00000028645 | ENSMUSG00000022575 | ENSMUSG00000003541 |
| ENSMUSG00000023307 | ENSMUSG00000026031 | ENSMUSG00000001768 | ENSMUSG00000074147 |
| ENSMUSG00000021660 | ENSMUSG00000020571 | ENSMUSG00000027712 | ENSMUSG00000047501 |
| ENSMUSG00000020457 | ENSMUSG00000038633 | ENSMUSG00000028405 | ENSMUSG00000026509 |
| ENSMUSG00000033306 | ENSMUSG00000035274 | ENSMUSG00000030630 | ENSMUSG00000029084 |
| ENSMUSG00000036777 | ENSMUSG00000016496 | ENSMUSG00000071172 | ENSMUSG00000032577 |
| ENSMUSG00000056501 | ENSMUSG00000060183 | ENSMUSG00000041431 | ENSMUSG00000019088 |
| ENSMUSG00000024672 | ENSMUSG00000026358 | ENSMUSG00000022351 | ENSMUSG00000052776 |
| ENSMUSG00000036438 | ENSMUSG00000000579 | ENSMUSG00000029580 | ENSMUSG00000066861 |
| ENSMUSG00000023067 | ENSMUSG00000073411 | ENSMUSG00000020638 | ENSMUSG00000037580 |
| ENSMUSG00000024401 | ENSMUSG00000004709 | ENSMUSG00000032724 | ENSMUSG00000033813 |
| ENSMUSG00000032487 | ENSMUSG00000002233 | ENSMUSG00000013089 | ENSMUSG00000030789 |
| ENSMUSG00000004936 | ENSMUSG00000050737 | ENSMUSG00000043953 | ENSMUSG00000021996 |
| ENSMUSG00000047126 | ENSMUSG00000057113 | ENSMUSG00000020057 | ENSMUSG00000025068 |
| ENSMUSG00000001128 | ENSMUSG00000026946 | ENSMUSG00000040681 | ENSMUSG00000024190 |
| ENSMUSG00000042029 | ENSMUSG00000026029 | ENSMUSG00000030934 | ENSMUSG00000030681 |
| ENSMUSG00000005413 | ENSMUSG00000031604 | ENSMUSG00000022336 | ENSMUSG00000045817 |
| ENSMUSG00000025534 | ENSMUSG00000024338 | ENSMUSG00000005087 | ENSMUSG00000022892 |
| ENSMUSG00000020865 | ENSMUSG00000014361 | ENSMUSG00000037851 | ENSMUSG00000010358 |
| ENSMUSG00000073489 | ENSMUSG00000074781 | ENSMUSG00000020612 | ENSMUSG00000025492 |
| ENSMUSG00000000982 | ENSMUSG00000028967 | ENSMUSG00000042396 | ENSMUSG00000020368 |
| ENSMUSG00000021125 | ENSMUSG00000029553 | ENSMUSG00000024337 | ENSMUSG00000026577 |
| ENSMUSG00000053113 | ENSMUSG00000004952 | ENSMUSG00000031897 | ENSMUSG00000027680 |
| ENSMUSG00000022895 | ENSMUSG00000056515 | ENSMUSG00000033257 | ENSMUSG00000026170 |
| ENSMUSG00000015002 | ENSMUSG00000054400 | ENSMUSG00000036591 | ENSMUSG00000029860 |
| ENSMUSG00000020611 | ENSMUSG00000051223 | ENSMUSG00000032366 | ENSMUSG00000021591 |
| ENSMUSG00000040152 | ENSMUSG00000052459 | ENSMUSG00000028037 | ENSMUSG00000031778 |

TABLE 4-continued

| | | | |
|---|---|---|---|
| ENSMUSG00000022901 | ENSMUSG00000078921 | ENSMUSG00000009079 | ENSMUSG00000073643 |
| ENSMUSG00000026739 | ENSMUSG00000078922 | ENSMUSG00000027804 | ENSMUSG00000031078 |
| ENSMUSG00000019866 | ENSMUSG00000017760 | ENSMUSG00000041247 | ENSMUSG00000031729 |
| | | ENSMUSG00000038612 | ENSMUSG00000026480 |
| | | ENSMUSG00000022403 | ENSMUSG00000079316 |
| | | ENSMUSG00000039997 | ENSMUSG00000019889 |
| | | ENSMUSG00000034459 | ENSMUSG00000029826 |
| | | ENSMUSG00000025888 | ENSMUSG00000032788 |
| | | ENSMUSG00000031799 | ENSMUSG00000025980 |
| | | ENSMUSG00000022323 | ENSMUSG00000028657 |
| | | ENSMUSG00000024949 | ENSMUSG00000024803 |
| | | ENSMUSG00000028788 | ENSMUSG00000009185 |
| | | ENSMUSG00000020377 | ENSMUSG00000032301 |
| | | ENSMUSG00000021963 | ENSMUSG00000026596 |
| | | ENSMUSG00000061104 | ENSMUSG00000035493 |
| | | ENSMUSG00000020794 | ENSMUSG00000040549 |
| | | ENSMUSG00000008398 | ENSMUSG00000001507 |
| | | ENSMUSG00000020423 | ENSMUSG00000039128 |
| | | ENSMUSG00000032515 | ENSMUSG00000020707 |
| | | ENSMUSG00000037712 | ENSMUSG00000070691 |
| | | ENSMUSG00000030265 | ENSMUSG00000016477 |
| | | ENSMUSG00000024805 | ENSMUSG00000028480 |
| | | ENSMUSG00000034543 | ENSMUSG00000004040 |
| | | ENSMUSG00000021109 | ENSMUSG00000049401 |
| | | ENSMUSG00000014554 | ENSMUSG00000005483 |
| | | ENSMUSG00000026276 | ENSMUSG00000002660 |
| | | ENSMUSG00000028268 | ENSMUSG00000057236 |
| | | ENSMUSG00000024991 | ENSMUSG00000025745 |
| | | ENSMUSG00000031447 | ENSMUSG00000030045 |
| | | ENSMUSG00000033020 | ENSMUSG00000059552 |
| | | ENSMUSG00000024052 | ENSMUSG00000025439 |
| | | ENSMUSG00000015850 | ENSMUSG00000030452 |
| | | ENSMUSG00000024781 | ENSMUSG00000025076 |
| | | ENSMUSG00000032370 | ENSMUSG00000024610 |
| | | ENSMUSG00000019528 | ENSMUSG00000029148 |
| | | ENSMUSG00000026622 | ENSMUSG00000022952 |
| | | ENSMUSG00000031483 | ENSMUSG00000041845 |
| | | ENSMUSG00000022359 | ENSMUSG00000003464 |
| | | ENSMUSG00000019943 | ENSMUSG00000032548 |
| | | ENSMUSG00000031595 | ENSMUSG00000021025 |
| | | ENSMUSG00000027944 | ENSMUSG00000037434 |
| | | ENSMUSG00000026421 | ENSMUSG00000042726 |
| | | ENSMUSG00000036381 | ENSMUSG00000026219 |
| | | ENSMUSG00000025499 | ENSMUSG00000027276 |
| | | ENSMUSG00000052727 | ENSMUSG00000029534 |
| | | ENSMUSG00000024737 | ENSMUSG00000020903 |
| | | ENSMUSG00000028029 | ENSMUSG00000079111 |
| | | ENSMUSG00000025574 | ENSMUSG00000028364 |
| | | ENSMUSG00000029388 | ENSMUSG00000034088 |
| | | ENSMUSG00000002900 | ENSMUSG00000038729 |
| | | ENSMUSG00000049734 | ENSMUSG00000067338 |
| | | ENSMUSG00000074896 | ENSMUSG00000067702 |
| | | ENSMUSG00000029373 | ENSMUSG00000057530 |
| | | ENSMUSG00000051510 | ENSMUSG00000039047 |
| | | ENSMUSG00000061130 | ENSMUSG00000018916 |
| | | ENSMUSG00000022505 | ENSMUSG00000037742 |
| | | ENSMUSG00000016382 | ENSMUSG00000027963 |
| | | ENSMUSG00000023088 | ENSMUSG00000020427 |
| | | ENSMUSG00000016559 | ENSMUSG00000054404 |
| | | ENSMUSG00000079509 | ENSMUSG00000024896 |
| | | ENSMUSG00000029672 | ENSMUSG00000055067 |
| | | ENSMUSG00000039384 | ENSMUSG00000026536 |
| | | ENSMUSG00000001082 | ENSMUSG00000054203 |
| | | ENSMUSG00000021266 | ENSMUSG00000002129 |
| | | ENSMUSG00000053644 | ENSMUSG00000014599 |
| | | ENSMUSG00000071054 | ENSMUSG00000040483 |
| | | ENSMUSG00000032612 | ENSMUSG00000021288 |
| | | ENSMUSG00000020009 | ENSMUSG00000021832 |
| | | ENSMUSG00000033964 | ENSMUSG00000020694 |
| | | ENSMUSG00000027882 | ENSMUSG00000070730 |
| | | ENSMUSG00000022565 | ENSMUSG00000000326 |
| | | ENSMUSG00000022971 | ENSMUSG00000038642 |
| | | ENSMUSG00000005107 | ENSMUSG00000030978 |
| | | ENSMUSG00000031813 | ENSMUSG00000001156 |
| | | ENSMUSG00000021250 | ENSMUSG00000002147 |
| | | ENSMUSG00000027611 | ENSMUSG00000024014 |
| | | ENSMUSG00000045934 | ENSMUSG00000048416 |
| | | ENSMUSG00000041278 | ENSMUSG00000022329 |
| | | ENSMUSG00000018899 | ENSMUSG00000028954 |

TABLE 4-continued

| | |
|---|---|
| ENSMUSG00000015947 | ENSMUSG00000018379 |
| ENSMUSG00000026135 | ENSMUSG00000060519 |
| ENSMUSG00000025591 | ENSMUSG00000029162 |
| ENSMUSG00000027678 | ENSMUSG00000056201 |
| ENSMUSG00000029156 | ENSMUSG00000022674 |
| ENSMUSG00000026986 | ENSMUSG00000022951 |
| ENSMUSG00000046711 | ENSMUSG00000020900 |
| ENSMUSG00000078249 | ENSMUSG00000068874 |
| ENSMUSG00000021048 | ENSMUSG00000026687 |
| ENSMUSG00000001674 | ENSMUSG00000020653 |
| ENSMUSG00000017466 | ENSMUSG00000036775 |
| ENSMUSG00000029467 | ENSMUSG00000060591 |
| ENSMUSG00000006589 | ENSMUSG00000022564 |
| ENSMUSG00000026104 | ENSMUSG00000049775. |

TABLE 5

| Gene | Fold change | P value |
|---|---|---|
| Irf7 | 4.5 | 0.0001 |
| Stat1 | 4.2 | 0.007 |
| Irf9 | 1.6 | 0.001 |
| Stat2 | 1.4 | 0.057 |

Suppression of Irf7 in Bone Metastases is Accompanied by Decreased Expression of the ISGF3 Complex.

Fold change represents decreased expression (as measured by Affymetrix microarray signal) in tumor cells purified from bone metastases compared to matched primary tumors (n=4).

TABLE 6

| | Normal Breast | Primary Tumor | Distant Metastases |
|---|---|---|---|
| IRF7 positive | 7 | 9 | 3 |
| IRF7 negative | 3 | 7 | 15 |
| Total | 10 | 16 | 18 |

IRF7 Expression in Normal Human Breast, Primary Tumors and Distant Metastases.

Archived, paraffin embedded sections of normal breast, primary breast tumors and matched metastases (including 7 bone metastases) were evaluated for IRF7 expression using immunohistochemistry. There was a significant reduction in IRF7 expression in metastases compared to the primary tumor (Fisher's exact test, p<0.04).

BIBLIOGRAPHY

Adeegbe et al., *Cell Transplant* 20:941-954 (2011)
Alon et al., *Proc. Natl. Acad. Sci. USA:* 96, 6745-6750, June 1999
Bunin B A, et al. (1994) *Proc. Natl. Acad. Sci. USA,* 91:4708-4712
Cimino et al., *Breast Cancer Res Treat* 123:701-708 (2010)
Culhane et al., *Nucleic Acids Research* 38:D716-D725 (2010)
DeRisi, et al., *Nature Genetics* 14:457-460 (1996)
DeWitt S H, et al. (1993) *Proc. Natl. Acad. Sci. USA,* 90:6909-6913
Dunn et al., *Nat Immunol* 6:722-729 (2005)
DuPre and Hunter, *Exp Mol Pathol* 82:12-24 (2007)
Eckhardt et al., *Mol Cancer Res* 3:1-13 (2005)
Fix (1996) *Pharm Res.* 13:1760-1764
Frith et al., *Nucleic Acids Res* 32: 1372-1381 (2004)
Germer et al., *Genome Res.* 10:258-266 (2000)
Guo et al., *Nucleic Acids Res.* 22:5456-5465 (1994)
Haibe-Kains et al., *J Natl Cancer Inst* 104:311-325 (2012)
Harrell et al. *Breast Cancer Res Treat* 132:523-535 (2012)
Hayakawa and Smyth, *J Immunol* 176:1517-1524 (2006)
Heid et al., *Genome Res.* 6:986-994 (1996)
Hervas-Stubbs et al., *Clin Cancer Res* 17:2619-2627 (2011)
Honda et al., *Nature* 434:772-777 (2005)
Hwang et al., *Proc Natl Acad Sci USA* 92:11284-11288 (1995)
Lelekakis et al., *Clin Exp Metastasis* 17:163-170 (1999)
Lu et al., *J Biol Chem* 275:31805-31812 (2000)
Maskos and Southern, *Nuc. Acids Res.* 20: 1679-84, 1992
Matys et al., *Nucleic Acids Res* 34:D108-110 (2006)
Mikeska et al., *Methods Mol. Biol.* 791:33-53 (2011)
Minn et al. *Nature* 436:518-524 (2005)
Nielsen (1999) *Curr. Opin. Biotechnol.* 10:71-75
Nielsen et al. (1991) *Science* 254: 1497-1500
Parker et al., *Cancer Res* 64:7857-7866 (2004)
Parker et al., *J Pathol* 214:337-346 (2008)
Patton (1998) *Biotechniques* 16:141-143
Pease et al., *Proc. Natl. Acad. Sci. USA* 91(11):5022-5026 (1994)
Pevzner et al., *J. Biomol. Struc. & Dyn.* 9:399-410, 1991
Putney (1998) *Nat. Biotechnol.* 16:153-157
Ribechini et al., *Med Microbiol Immunol* 3:273-281 (2010)
Samanen (1996) *J. Pharm. Pharmacol.* 48:119-135
Savitsky et al., *Cancer Immunol Immunother* 59:489-510 (2010)
Schena, et al. *Science* 270:467-470 (1995)
Sheehan et al., *J Interferon Cytokine Res* 26:804-819 (2006)
Smith et al., *Science* 258:1122-1126 (1992) St Croix et al., *Science (New York, N.Y.)* 289:1197-1202 (2000)
T. Sano and C. R. Cantor, *Bio/Technology* 9:1378-81 (1991)
Urdea et al., *Nucleic Acids Symp. Ser.,* 24:197-200 (1991)
Waight et al., *PLoS One* 6:e27690 (2011)
Wojdacz and Dobrovic, *Nucleic Acids Res* 35:e41 (2007)
Wu et al., *Appl Immunohistochem Mol Morphol* 10:269-274 (2002)
Wu et al., *Clin Cancer Res* 14:1938-1946 (2008)
Yang et al., *Cancer Cell* 13:23-35 (2008)
Youn et al., *J Immunol* 181:5791-5802 (2008)

The invention claimed is:

1. A method of diagnosing and treating metastatic breast tumour in an individual, said method comprising:
  (i) obtaining a biological sample of a primary breast tumour from said individual;
  (ii) detecting the expression level of interferon regulatory factor 7 (IRF7) and interferon regulatory factor 9 (IRF9) in said tumour;
  (iii) diagnosing a metastatic phenotype of said tumour when the expression level of said IRF7 and IRF9 is decreased in comparison to a non-metastatic breast tumour;
  (iv) administering an effective amount of an agent to the diagnosed individual, wherein the agent is a Toll-like receptor (TLR) agonist selected from the group consisting of interferon alpha (IFN α), poly I:C and imiquimod, and wherein the agent increases the level of Type I interferon (IFN) in the diagnosed individual.

2. The method of claim 1 wherein the metastatic breast tumour metastases are present in the bone.

3. The method of claim 1 wherein the expression level is assessed by detecting RNA transcripts, cDNA transcribed from the RNA transcripts or a protein expression product from the RNA transcripts.

4. The method of claim 1 wherein the individual is a human.

5. The method of claim 1, wherein step (ii) further comprises detecting the expression level of signal transducer and activator of transcription 1 (STAT1) in said tumour.

6. The method according to claim 5, wherein step (ii) further comprises detecting the expression level of one or more of DEXH-Box Helicase 58 (DHX58), Bone Marrow Stromal Cell Antigen 2 (BST2), Interferon Induced Protein 44 (IFI44), Interferon Induced Protein With Tetratricopeptide Repeats 3 (IFIT3), Desmoplakin (DSP) and Ubiquitin Specific Peptidase 18 (USP18) in said tumour.

7. A method of assessing the metastatic status of a primary breast tumour from an individual, said method comprising:

(i) obtaining a biological sample of the primary breast tumour from said individual;
(ii) detecting the expression level of interferon regulatory factor 7 (IRF7) and interferon regulatory factor 9 (IRF9) in said tumour;
(iii) diagnosing a metastatic phenotype of said tumour when the expression level of said IRF7 and IRF9 is decreased in a comparison to a non-metastatic breast tumour;
(iv) administering an effective amount of an agent to the diagnosed individual, wherein the agent is a TLR agonist selected from the group consisting of interferon alpha (IFN α), poly I:C and imiquimod, and wherein the agent increases the level of Type I interferon (IFN) in the diagnosed individual.

8. The method of claim 7 wherein the expression level is assessed by detecting RNA transcripts, cDNA transcribed from the RNA transcripts or a protein expression product from the RNA transcripts.

9. The method of claim 7 wherein the individual is a human.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
tcccactctt ccaccttcga                                                20

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
gtccaccacc ctgttgctgt a                                              21

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
ccacaccccc atcttcga                                                  18

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
cctccgagcc cgaaactc                                                  18

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
gctctagcca tagccaagag aatc                                           24

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
tccagtaaat gtcgggcaaa g                                              21

<210> SEQ ID NO 7
<211> LENGTH: 24
<212> TYPE: DNA
<213> ORGANISM: Artificial

```
<220> FEATURE:
<223> OTHER INFORMATION: primer

<400> SEQUENCE: 7
cgcgcatgca actggcatat aact                                              24

<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
aagctcgaac cactgtgaca tcct                                              24

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
aggtacgaaa tggccaggac a                                                 21

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
tggcagcaga tggaaaacct ag                                                22

<210> SEQ ID NO 11
<211> LENGTH: 31
<212> TYPE: DNA
<213> ORGANISM: Artificial
<220> FEATURE:
<223> OTHER INFORMATION: primer

<400> SEQUENCE: 11
gagtggttta agagttttat atatttggta t                                      31

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
accacaccct acctaaactc ta                                                22

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
agatagcggg aagttagtag ttat                                              24
```

```
<210> SEQ ID NO 14
<211> LENGTH: 29
<212> TYPE: DNA
<213> ORGANISM: Artificial
<220> FEATURE:
<223> OTHER INFORMATION: primer

<400> SEQUENCE: 14
ctaaataaac tatcacaaac taaacccta                                29

<210> SEQ ID NO 15
<211> LENGTH: 28
<212> TYPE: DNA
<213> ORGANISM: Artificial
<220> FEATURE:
<223> OTHER INFORMATION: primer

<400> SEQUENCE: 15
ggtttagttt gtgatagttt atttaggt                                 28

<210> SEQ ID NO 16
<211> LENGTH: 31
<212> TYPE: DNA
<213> ORGANISM: Artificial
<220> FEATURE:
<223> OTHER INFORMATION: primer

<400> SEQUENCE: 16
ctcaatataa attcctctac caaaataact a                             31

<210> SEQ ID NO 17
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (5)..(5)
<223> OTHER INFORMATION: n is a, c, g, or t

<400> SEQUENCE: 17
ggtgngttga tggaatagt                                           19

<210> SEQ ID NO 18
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (2)..(2)
<223> OTHER INFORMATION: n is a, c, g, or t

<400> SEQUENCE: 18
cnaaaatctc caaaaaactt taacaa                                   26
```